(12) United States Patent
Roggendorf et al.

(10) Patent No.: US 8,889,137 B2
(45) Date of Patent: Nov. 18, 2014

(54) ANTI-HSV ANTIBODY

(75) Inventors: Michael Roggendorf, Essen (DE);
Anna-Maria Eis-Hübinger, Alfter
(DE); Jürgen Krauss, Wilhelmsfeld
(DE); Karl Eduard Schneweis, Bonn
(DE); Edelgard Schneweis, legal
representative, Bonn (DE); **Michaela
Arndt, Wilhelmsfeld (DE); Adalbert
Krawczyk, Mülheim (DE); Evelyn
Exner, Nuβloch (DE); Martin P.
Däumer**, Kaiserslautern (DE)

(73) Assignees: Universität Duisberg Essen, Essen
(DE); **Rheinische Friedrich Wilhelms
—Universität Bonn**, Bonn (DE)

(*) Notice: Subject to any disclaimer, the term of this patent is extended or adjusted under 35 U.S.C. 154(b) by 0 days.

(21) Appl. No.: 13/499,429

(22) PCT Filed: Oct. 1, 2010

(86) PCT No.: PCT/EP2010/006020
§ 371 (c)(1),
(2), (4) Date: Oct. 19, 2012

(87) PCT Pub. No.: WO2011/038933
PCT Pub. Date: Apr. 7, 2011

(65) Prior Publication Data
US 2013/0058952 A1 Mar. 7, 2013

(30) Foreign Application Priority Data
Oct. 1, 2009 (EP) ..................................... 09012454

(51) Int. Cl.
*A61K 39/245* (2006.01)
*C07K 16/08* (2006.01)
*A61K 39/00* (2006.01)

(52) U.S. Cl.
CPC ........... *C07K 16/087* (2013.01); *C07K 2317/92* (2013.01); *C07K 2317/34* (2013.01); *C07K 2317/567* (2013.01); *C07K 2316/96* (2013.01); *A61K 2039/505* (2013.01); *C07K 2317/565* (2013.01); *C07K 2317/55* (2013.01); *C07K 2317/54* (2013.01); *C07K 2317/24* (2013.01)
USPC ................... 424/159.1; 530/391.3; 530/389.4

(58) Field of Classification Search
None
See application file for complete search history.

(56) References Cited

U.S. PATENT DOCUMENTS

| 4,950,595 A | 8/1990 | Masuho et al. |
| 6,180,370 B1 | 1/2001 | Queen et al. |
| 2004/0058414 A1 | 3/2004 | Queen et al. |

FOREIGN PATENT DOCUMENTS

| DK | 187286 A | 4/1986 |
| WO | WO-97/26329 A1 | 7/1997 |
| WO | WO-03/105782 A2 | 12/2003 |

OTHER PUBLICATIONS

Eis-Hubinger et al. Anti-glycoprotein B monoclonal antibody protects T cell-depleted mice against herpes simplex virus infection by inhibition of virus replication at the inoculated mucous membranes. Journal of General Virology (1993), 74, 379-385.*
GenBank: AAD53863.1. immunoglobulin heavy chain variable region [*Homo sapiens*]. May 8, 2001.*
PIR: S40321. Ig kappa chain—human. Jan. 21, 2000.*
Carter et al. Humanization of an anti-p185HER2 antibody for human cancer therapy. Proc Natl Acad Sci U S A. May 15, 1992;89(10):4285-9.*
Li et al. Monoclonal antibody-based therapeutics for leukemia. Expert Opin Biol Ther. Mar. 2007;7(3):319-30.*
Almagro et al., "Humanization of Antibodies," *Front Biosci.* 13:1619-1633 (2008).
Bender et al., "Antigenic and mutational analyses of herpes simplex virus glycoprotein B reveal four functional regions," *J Virol.* 81(8):3827-3841 (2007).
Bystrická et al., "Monoclonal antibodies to the distinct antigenic sites on glycoproteins C and B and their protective abilities in herpes simplex virus infection," *Acta Virol.* 41:5-12 (1997).
Charles et al., "Prevention of human rhinovirus infection by multivalent Fab molecules directed against ICAM-1," *Antimicrob Agents Chemother.* 47(5):1503-1508 (2003).
Chothia et al., "Conformations of immunoglobulin hypervariable regions," *Nature* 342:877-883 (1989).
Co et al., "Humanized antibodies for antiviral therapy," *Proc Natl Acad Sci USA* 88:2869-2873 (1991).
Eis-Hübinger et al., "Anti-glycoprotein B monoclonal antibody protects T cell-depleted mice against herpes simplex virus infection by inhibition of virus replication at the inoculated mucous membranes," *J Gen Virol.* 74:379-385 (1993).

(Continued)

*Primary Examiner* — Nicole Kinsey White
*Assistant Examiner* — Nick Zou
(74) *Attorney, Agent, or Firm* — Kristina Bieker-Brady; Clark & Elbing LLP

(57) ABSTRACT

The invention relates to an anti-HSV antibody as defined in the claims, a pharmaceutical composition comprising of an effective amount of the said antibody, an expression vector comprising of a nucleotide sequence which encodes the said antibody, a host cell comprising of the said nucleotide sequence, a hybridoma cell capable of producing the said antibody and the use of the said antibody as a drug, in particular to use for the manufacture of a drug for the prophylactical or therapeutical treatment of HSV-associated diseases in a subject; as defined in the claims.

32 Claims, 25 Drawing Sheets

(56) References Cited

OTHER PUBLICATIONS

Eis-Hübinger et al., "Different mechanisms of protection by monoclonal and polyclonal antibodies during the course of herpes simplex virus infection," *Intervirology* 32:351-360 (1991).

Heldwein et al., "Crystal structure of glycoprotein B from herpes simplex virus 1," *Science* 313:217-220 (2006).

Highlander et al., "Identification of *mar* mutations in herpes simplex virus type 1 glycoprotein B which alter antigenic structure and function in virus penetration," *J Virol.* 63:730-738 (1989).

Highlander et al., "Monoclonal antibodies define a domain on herpes simplex virus glycoprotein B involved in virus penetration," *J Virol.* 62(6):1881-1888 (1988).

Koga et al., "Studies on herpes simplex virus type 1 glycoproteins using monoclonal antibodies," *Virology* 151:385-389 (1986).

Kousoulas et al., "Antibody-resistant mutations in cross-reactive and type-specific epitopes of herpes simplex virus 1 glycoprotein B map in separate domains," *Virology* 166:423-431 (1988).

Kousoulas et al., "Mutations affecting conformation or sequence of neutralizing epitopes identified by reactivity of vi

Fig. 4

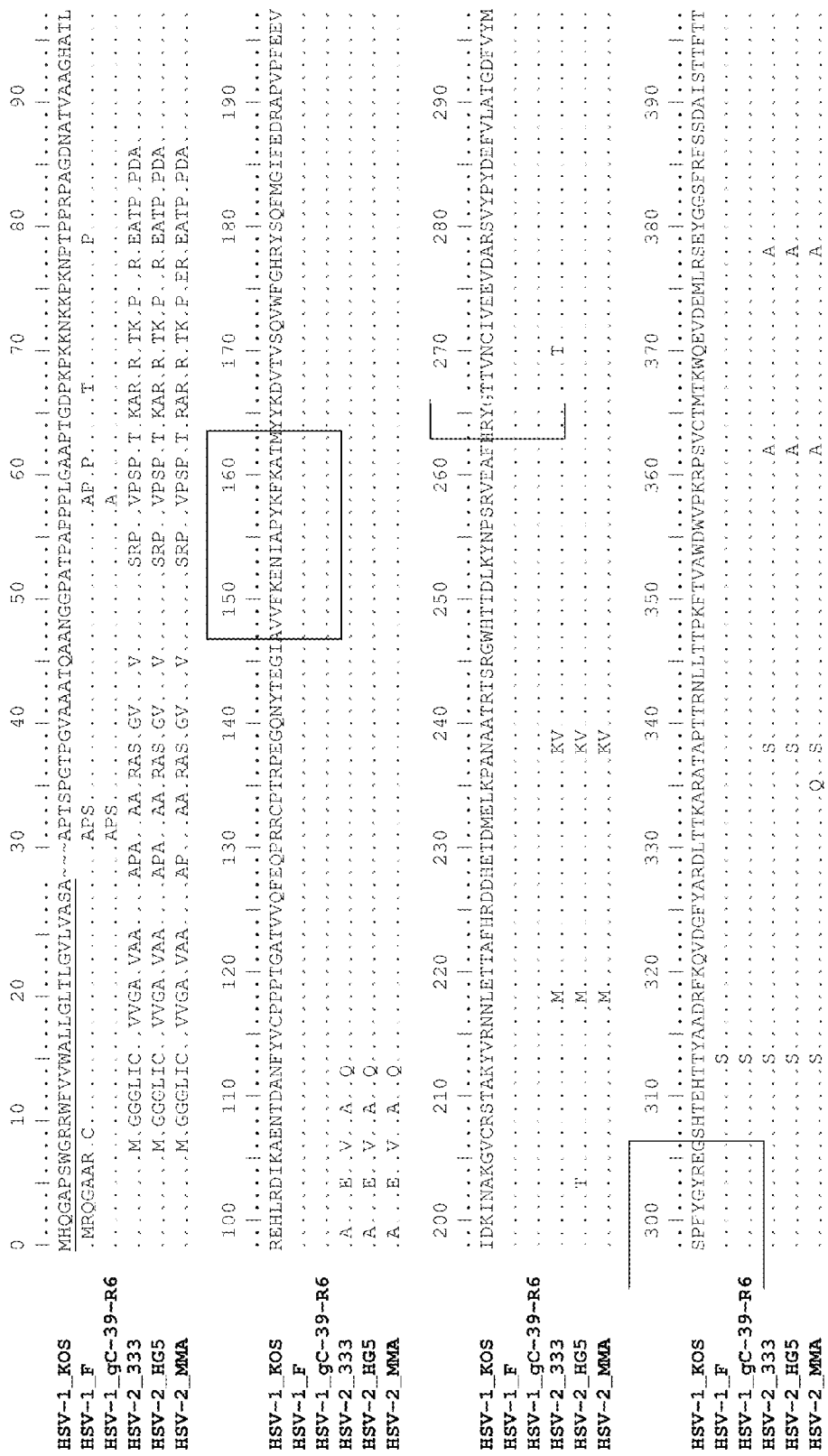

Fig. 13A continued

[Figure: Multiple sequence alignment of HSV-1 and HSV-2 glycoprotein sequences (HSV-1_KOS, HSV-1_F, HSV-1_gC-39-R6, HSV-2_333, HSV-2_HG5, HSV-2_MMA) spanning residues 400–790.]

Fig. 13A continued

```
             800       810       820       830       840       850       860       870       880       890
             ....|....|....|....|....|....|....|....|....|....|....|....|....|....|....|....|....|....|....|....|
HSV-1_KOS    RYVMRLQSNPMKALYPLTTKELKNPTNPDASGEGEE...GGDFDEAKLAEAREMIRYMALVSAMERTEHKAKKKGTSALLSAKVTDMVMKRRNTNYTQV
HSV-1_F      ..................................................................................................
HSV-1_gC-39-R6 ................................................................................................
HSV-2_333    .........................TSDPGGVG.....GAE..G................................R.........S...N.L...NKAR.SPL
HSV-2_HG5    .........................TSDPGGVG.....GAE..G................................R.........S...N.L...NKAR.SPL
HSV-2_MMA    .........................TSDPGGVG.....GAE..G................................R.........S...N.L...NKAR.SPL

900
             ....|....|
HSV-1_KOS    PNKDGDADEDDL   (SEQ ID NO:12)
HSV-1_F      ...........    (SEQ ID NO:11)
HSV-1_gC-39-R6 .........    (SEQ ID NO:13)
HSV-2_333    H.E.EAG...E.   (SEQ ID NO:15)
HSV-2_HG5    H.E.EAG...E.   (SEQ ID NO:14)
HSV-2_MMA    H.E.EAG...E.   (SEQ ID NO:16)
```

48: $_{172}$QVWFGHRYSQFMG$_{184}$  (SEQ ID NO:18)
49: ...$_{175}$FGHRYSQFMGIFE$_{187}$  (SEQ ID NO:57)
50: ......$_{178}$RYSQFMGIFEDRA$_{190}$  (SEQ ID NO:58)
51: .........$_{181}$QFMGIFEDRAPVP$_{193}$  (SEQ ID NO:59)
52: ............$_{184}$GIFEDRAPVPFEE$_{196}$  (SEQ ID NO:60)

89: $_{295}$VYMSPFYGYREGS$_{307}$  (SEQ ID NO:61)
90: ...$_{298}$SPFYGYREGSHTE$_{310}$  (SEQ ID NO:62)
91: ......$_{301}$YGYREGSHTEHTS$_{313}$  (SEQ ID NO:63)

Complete neutralization of HSV-1(100 $TCID_{50}$)

49: $_{175}$FGHRYSQFMGIFEDR$_{188}$ (SEQ ID NO:78)  90: $_{298}$SPFYGYREGSHTEHT$_{312}$ (SEQ ID NO:80)
50: $_{176}$RYSQFMGIFEDRAPV$_{192}$ (SEQ ID NO:43)  91: $_{301}$YGYREGSHTEHTSYA$_{315}$ (SEQ ID NO:81)
51: $_{181}$QFMGIFEDRAPVPFE$_{195}$ (SEQ ID NO:79)

Fig. 23

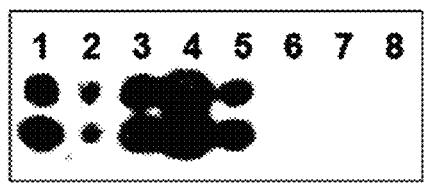

1: ₁₉₆YMSPFYGYREGSH (SEQ ID NO:82)
2: MSPFYGYREGSHT (SEQ ID NO:83)
3: SPFYGYREGSHTE (SEQ ID NO:84)
4: PFYGYREGSHTEH (SEQ ID NO:85)
5: FYGYREGSHTEHT (SEQ ID NO:86)
6: YGYREGSHTEHTS (SEQ ID NO:87)
7: GYREGSHTEHTSY (SEQ ID NO:88)
8: YREGSHTEHTSYA₃₁₅ (SEQ ID NO:89)

Fig. 24

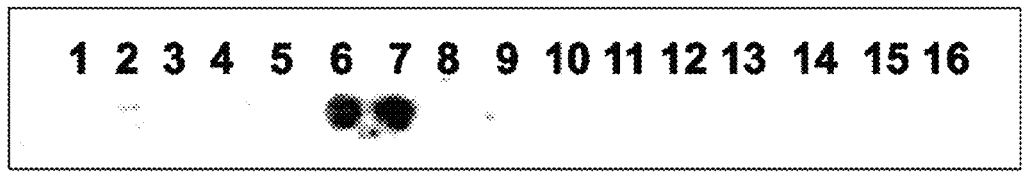

1: ₂₉₅VYMSPF (SEQ ID NO:90)
2: YMSPFY (SEQ ID NO:91)
3: MSPFYG (SEQ ID NO:92)
4: SPFYGY (SEQ ID NO:93)
5: ₂₉₉PFYGYR (SEQ ID NO:94)
6: FYGYRE (SEQ ID NO:95)
7: YGYREG (SEQ ID NO:96)
8: GYREGS (SEQ ID NO:97)

9: ₃₀₃YREGSH (SEQ ID NO:98)
10: REGSHT (SEQ ID NO:99)
11: EGSHTE (SEQ ID NO:100)
12: GSHTEH (SEQ ID NO:101)
13: ₃₀₇SHTEHT (SEQ ID NO:102)
14: HTEHTS (SEQ ID NO:103)
15: TEHTSY (SEQ ID NO:104)
16: EHTSYA₃₁₅ (SEQ ID NO:105)

ered and also
iatrogenic immune deficiency, to some extent severe progres-
ANTI-HSV ANTIBODY

CROSS-REFERENCE TO RELATED APPLICATIONS

This application is the National Stage of International Application No. PCT/EP2010/006020, filed Oct. 1, 2010, which claims the benefit of European Patent Application No. 09012454.6, filed Oct. 1, 2009.

BACKGROUND OF THE INVENTION

The invention relates to an anti-HSV antibody as defined in the claims, a pharmaceutical composition comprising of an effective amount of the said antibody, an expression vector comprising of a nucleotide sequence which encodes the said antibody, a host cell comprising of the said nucleotide sequence, a hybridoma cell capable of producing the said antibody and the use of the said antibody as a drug, in particular to use for the manufacture of a drug for the prophylactical or therapeutical treatment of HSV-associated diseases in a subject; as defined in the claims.

The human pathogenic Herpes simplex virus (HSV) is a dermatotropic and neutrotropic DNA virus, whose clinical manifestations primarily originate from the skin and the nearby mucosa, and secondarily lead to neurological complications such as neuritis, meningitis, encephalitis, myelitis, polyradiculitis amongst others. At innate, acquired and also iatrogenic immune deficiency, to some extent severe progressions with a high lethality are reported. Due to the high infection rates of the population with HSV type 1 (HSV-1, 95%; *H. labialis, H. cornea*, eczema herpeticatum) and HSV type 2 (HSV-2, 10-30%; *H. genitalis, H. neonatorum*) and due to the often reactivation of the virus, latently persisting lifelong in the sensory and autonomic neural ganglions, HSV is of particular clinical relevance. Independent from the type of virus, the symptomatic therapeutic aims of primary or recidivating HSV infection are the inhibition of virus replication, shortening of the time of suffering, and prevention of the systemic complications influencing the frequency of recrudescence.

At early recognition and correct dosage, virustatic agents are successfully employed for antiviral therapy. The most common virustatic agents (e.g. acyclovir, penciclovir, foscarnet, idoxuridin) are nucleoside or pyrophosphate analogues, whose common active principle is based on the inhibition of DNA synthesis in virus-infected cells.

One of the most important therapeutic agents for the treatment of HSV infections is the purine nucleoside analogue acyclovir. It is phosphorylated by the viral thymidine kinase and then interferes with the viral DNA polymerase. In contrast, the human DNA polymerase is less susceptible against acyclovir by factor 30-50, for which reason merely marginal side effects are observed.

However, despite the development of selectively acting virustatic agents, chemotherapeutic treatment of viral diseases still represents a serious problem. In particular, the development of resistant strains against common chemotherapeutic agents observed during long-lasting prophylactic and therapeutic treatment of immunosuppressed patient is problematic. As a result, in more than 10% of the cases, due to the lack of effective virustatic agents, a fast progressing generalised infection with lethal progression is observed.

Presently, the pyrophosphate analogue foscarnet is particularly employed in immunosuppressed patients against acyclovir-resistant herpes virus. This agent causes a direct inhibition of the viral DNA polymerase and has no influence on the thymidine kinase. However, the use of foscarnet leads to severe undesirable side effects such as renal failure, cardiac problems, has toxicity on the bone marrow, and may also cause cutaneous ulceration. Because of its teratogenic effects, foscarnet may also not be administered during pregnancy. Further, the formation of cross-resistant strains is observed, which makes the development of alternative therapeutic agents highly necessary. A passive immunoprophylaxis is currently not available. A couple of experimental vaccine for active immunisation against HSV1 and HSV2 showed no verifiable success.

Antibodies hold great promise for the treatment of cancer, autoimmune disorders, and viral infections. JP 6135854 describes a therapeutic agent for herpes simplex virus infection in which a human monoclonal antibody against HSV and an antiviral nucleic acid analog such as acyclovir (ACV) are simultaneously or successively administered in the form of injection by intravenous drip infusion. DK 187286 discloses antibodies which exhibit multispecific immunoreactivities with regard to glycoprotein D (gD) from HSV-1 and HSV-2 (HSV gD-1 and gD-2). WO 1997/26329 describes human monoclonal antibodies useful for the diagnosis and treatment of HSV-1 and HSV-2. The latter antibody competes with the HSV 863 monoclonal antibody for binding to the glycoprotein D antigen of HSV-1 and HSV-2. U.S. Pat. No. 4,950,595 discloses a mouse-human hybridoma which produces an anti-virus-human antibody, a process for preparation thereof, and an antivirus-human monoclonal antibody.

Furthermore, the humanization of another murine monoclonal antibody (Fd79) (Kogae et al., 1986) specific for HSV1/2 is described (Co, M. S. et al., 1991; Zeitlin L. et al., 1998). This antibody recognizes a shared epitope of glycoprotein B (gB) of HSV1 and HSV2. Moreover, humanized Fd79 has been produced in both transgenic plants and in the eukaryotic cell line SP2/0 and subsequently characterised, showing an affinity of 53 nM. Monoclonal murine antibody H1815 recognizes a similar but not identical epitope in the region of amino acids 263-283 of glycoprotein B (gB) (Navarro et al., 1992). However, H1815 is not capable of viral neutralization or inhibition of "cell-to-cell spread". Finally, U.S. Pat. No. 6,180,370 describes humanized immunoglobulins and methods of making the same. Moreover, WO 2003/105782 pertains to specificity grafting of a murine antibody onto a human framework.

Thus, chemotherapeutic agents have undesired side effects and an increasing number of resistant strains is observed.

It is therefore an object of the invention to provide a (humanized) anti-HSV antibody which is capable of neutralising HSV infection and inhibiting cell-to-cell spread. Moreover, it is an object of the invention to provide a prophylactic and/or therapeutic agent for the treatment of HSV associated diseases which overcomes the above-mentioned disadvantages of conventionally applied chemotherapeutic agents.

Surprisingly, it was found that an antibody according to the invention solves this object. Accordingly, the present invention provides a promising alternative to the therapeutic agents known in the art for the treatment of HSV-infection on the basis of recombinantly produced antibodies, which may be humanized. These antibodies are capable of blocking both viral mechanisms to spread within a host. They effectively neutralize cell-free virus particles and inhibit the direct cell-to-cell spread of the virus. Since the antibodies specifically bind to a highly conserved epitope of the surface glycoprotein B (gB) of the HSV1 and HSV2 envelope, which is essential for the viral replication cycle, development of drug resistance is most unlikely.

Even though the effect of the murine antibody of the invention has in part already been described, c.f. Eis-Hübinger et al., Intervirology (1991); 32:351-360 and Eis-Hübinger et al., Journal of General Virology (1993); 74: 379-385, the antibody itself or the sequence of the complementarity determining regions (CDR) of the antibody of the invention as well as the epitope with which it binds to has never been published or made available to the public. In summary, the (humanized) antibody provides one or more of the following advantages:

The efficacy of the murine monoclonal antibody of the invention has already been proven (c.f. Eis-Hübinger et al., 1991; Eis-Hübinger et al., 1993). Moreover, the inventors show in the Examples section that the humanized antibody of the invention is also able to neutralize in vitro HSV1 and HSV2 viral infection and to inhibit viral spreading by inhibiting the "cell-to-cell spread" mechanism. In the context of infection progression in humans, the human immune system is not capable to generate antibody specificities for efficiently preventing HSV1/2 typical cell-to-cell spread.

The often and long-lasting prophylactic as well as therapeutic application of conservative chemotherapeutic agents such as acyclovir and foscarnet leads to an increase of the formation of resistant viral strains. This problem of resistance may be overcome by the (humanized) anti-HSV antibody described herein, administered alone or in combination with a virustatic agent such a acyclovir and/or foscarnet, since it relies on a different mechanism of action.

The antibody described herein specifically binds an epitope of the HSV gB protein. Development of HSV-resistance against the antibody of the invention is not to be expected, since mutations in the gB-protein lead to loss of viral infectivity.

Patients in which the systemic administration of conventional virustatic agents is contraindicated profit particularly from the (humanized) antibody described herein.

SUMMARY OF THE INVENTION

Accordingly, an antibody, comprising the complementarity determining regions shown in SEQ ID NO: 1, SEQ ID NO: 2, SEQ ID NO: 3, SEQ ID NO: 4, SEQ ID NO: 5, and SEQ ID NO: 6 is provided. Additionally, an antibody is provided, which recognizes the same epitope as the antibody comprising the complementarity determining regions shown in SEQ ID NOs: 1-6.

Furthermore, a pharmaceutical composition comprising of an effective amount of the antibody described herein and at least one pharmaceutically acceptable excipient is also provided.

Moreover, an expression vector, comprising a nucleotide sequence which encodes the antibody as defined in the claims, a cell comprising of the said nucleotide sequence, and a hybridoma cell capable of producing the said antibody is provided.

Finally, the antibody as defined in the claims for use in medicine, and the use of the antibody as defined in the claims for the manufacture of a medicament for the prophylactical or therapeutical treatment of HSV-associated diseases in a subject are as well provided herein.

The various aspects of the invention as defined in the independent claims and the preferred embodiments contained in the dependent claims are herewith incorporated by reference.

DETAILED DESCRIPTION OF THE INVENTION

Accordingly, in a first aspect, the invention relates to an antibody, comprising the complementarity determining regions shown in SEQ ID NO: 1 (TSGMSVG), SEQ ID NO: 2 (HIWWNNDKYYKPALKS), SEQ ID NO: 3 (IYYGYRPYAMDY), SEQ ID NO: 4 (RSSQSIVHSNGNTYLE), SEQ ID NO: 5 (KVSNRFS), and SEQ ID NO: 6 (FQGSHVPWS).

Antibodies or immunoglobulins are gamma globulin proteins consisting in their natural form of two large heavy chains and two small light chains linked by disulfide bonds (c.f. FIG. 3). There are five types of mammalian Ig heavy chain: α, δ, ε, γ, and μ. The type of heavy chain present defines the class (isotype) of the antibody; these are IgA, IgD, IgE, IgG, and IgM antibodies, respectively. Each heavy chain has two regions, the constant region and the variable region. The constant region is nearly identical in all naturally occurring antibodies of the same isotype of the same species. A light chain also consists of one constant domain and one variable domain. In mammals there are two types of immunoglobulin light chain, lambda (λ) and kappa (κ).

Although the general structure of all antibodies is very similar, the unique property of a given antibody is determined by the variable (V) regions. More specifically, variable loops, three each on the light ($V_L$) and three on the heavy ($V_H$) chains, are responsible for binding to the antigen, i.e. for its antigen specificity. These loops are referred to as the Complementarity Determining Regions (CDRs). Because CDRs from both $V_H$ and $V_L$ domains contribute to the antigen-binding site, it is the combination of the heavy and the light chains, and not either alone, that determines the final antigen specificity.

The term "antibody", as used herein, means any polypeptide which is capable of binding to an antigen, wherein the binding specificity is determined by the CDRs shown in SEQ ID NOs: 1 to 6. Hence, "antibody" is intended to relate to any polypeptide which comprises of at least one antigen binding fragment. Antigen binding fragments consist of at least the variable domain of the heavy chain and the variable domain of the light chain, arranged in a manner that both domains together are able to bind to the specific antigen. An "antibody" includes a complete antibody, or antibody fragments, e.g. Fab-, $F(ab)_2$- or scFv-fragments (c.f. also FIG. 3).

With regard to the term "complete antibody", any antibody is meant that has a typical overall domain structure of a naturally occurring antibody (i.e. comprising a heavy chain of three or four constant domains and a light chain of one constant domain as well as the respective variable domains), even though each domain may comprise of further modifications, such as mutations, deletions, or insertions, which do not change the overall domain structure.

An "antibody fragment" also contains at least one antigen binding fragment as defined above, and exhibits the same function and specificity as the complete antibody from which the fragment is derived. Fab fragments may be generated by using the enzyme papain to cleave an immunoglobulin. The enzyme pepsin cleaves below the hinge region and, thus, below the disulfide bonds, so that an $F(ab)_2$ fragment is formed. Moreover, the variable regions of the heavy and light chains can be fused together to form a single chain variable fragment (scFv).

In addition, the term "antibody" is intended to comprise of all above-mentioned immunoglobulin isotypes, i.e. the antibody may be an IgA, IgD, IgE, IgG, or IgM antibody, including any subclass of these isotypes. Preferably, the antibody is an IgG antibody, more preferably an IgG1 or IgG2 antibody. Since the antibody may be expressed and produced recombinantly, the antibody may also comprise of two different constant regions of heavy chains, e.g. one IgG1 and one IgG2 heavy chain, or heavy chains from different species. However, the heavy chains are preferably from the same species. Moreover, the antibody may comprise of either a lambda or a kappa light chain.

As shown in Example 2, the valency of the antibody has a big influence on the efficacy to mediate viral neutralization and inhibit cell-to-cell spread, and the best results have been shown with bivalent antibodies, i.e. with an antibody having two antigen binding regions. Examples for bivalent antibodies are complete antibodies or bivalent antibody fragments, such as an F(ab)$_2$-fragment. Therefore, in a preferred embodiment, the antibody is a bivalent antibody, preferably wherein the antibody is a complete antibody or an antibody fragment, in particular wherein the antibody fragment is an F(ab)$_2$ fragment. In an alternatively preferred embodiment, the antibody is a multivalent antibody, i.e. an antibody having more than two binding-sites, including recombinant antibodies or fragments thereof, preferably a triabody or a tetrabody, or whole immunoglobulins such as an IgM pentamer or linked immunoglobulins. These antibody formats are known in the art.

In another preferred embodiment, the antibody is a monoclonal antibody, preferably wherein the antibody is a murine antibody, a chimeric antibody or a humanized antibody, more preferably wherein the humanized antibody is derived from a human germline sequence, as discussed below. A chimeric antibody is an antibody in which at least one region of an immunoglobulin of one species is fused to another region of an immunoglobulin of another species by genetic engineering in order to reduce its immunogenecity. An example for a chimeric antibody is shown in FIG. 3A, which depicts murine $V_L$ and $V_H$ regions fused to the remaining part of a human immunoglobulin. A particular type of chimeric antibodies are humanized antibodies. Humanized antibodies are produced by grafting the DNA that encodes the CDRs of a non-human antibody into human antibody framework coding DNA. The resulting DNA construct can then be used to express and produce antibodies that are usually not as immunogenic as the non-human parenteral antibody or as a chimeric antibody, since merely the CDRs are non-human.

In one preferred embodiment, the antibody is capable of inhibiting the spreading of HSV infection from an infected cell to an adjacent second non-infected cell (cell-to-cell spread). Cell-to-cell spread is the ability of the herpes virus to spread from one infected cell to an adjacent non-infected cell, without releasing cell-free particles. In order to examine whether an antibody is capable of inhibiting the spread of HSV from an infected cell to an adjacent second non-infected cell (cell-to-cell spread), the following assay can be used.

Vero cells grown to confluency on glass cover slips in 24-weel tissue culture plates are infected for 4 h at 37° C. with a constant virus amount of 400 TCID$_{50}$/well. One median tissue culture infective dose (1 TCID$_{50}$) is the amount of a cytopathogenic agent, such as a virus, that will produce a cytopathic effect in 50% of the cell cultures inoculated. The virus inoculum is subsequently removed, the cells washed twice with PBS and further incubated for 2 days at 37° C. in 1 ml DMEM, 2% FCS, Pen/Strep containing an excess of either different anti-HSV antibodies or polyclonal anti-HSV control serum in order to prevent viral spreading via the supernatant Viral antigens of HSV-infected cells are detected with a fluorescence labelled polyclonal goat-anti-HSV-serum (BETHYL Laboratories, Montgomery, Tex. USA, Catalog No. A190-136F, Lot No. A190-136F-2).

Preferably, an antibody is capable of inhibiting cell-to-cell spread if less than 20% of the adjacent cells are infected, preferably wherein less than 15%, less than 10%, less than 5%, more preferably less than 3% and most preferably less than 1% of the adjacent cells are infected in the above assay.

Still, in a further preferred embodiment, the antibody has a dissociation constant $K_D$ of at most 40 nM, preferably at most 30 nM, more preferably at most 20 nM, even more preferably at most 15 nM, such as at most 13 nM, at most 10 nM, and most preferably at most 7 nM. The $K_D$ represents the dissociation constant as a measure of the propensity of a complex to dissociate reversibly into its components (i.e. the affinity of the antibody for the antigen) and is the inverse of the association constant. The $K_D$ may be calculated from the Scatchard equation and methods for determining $K_D$ are well known in the art.

In an additional preferred embodiment, the antibody in a concentration of at most 20 nM, preferably of at most 16 nM, more preferably of at most 12 nM, such as of at most 10 nM, e.g. at most 8 nM or at most 6 nM, and most preferably of at most 4 nM is capable of neutralizing a defined amount of HSV of 100 TCID$_{50}$ to more than 80%, preferably by more than 90%, such as more than 95%, more preferably more than 96%, e.g. more than 97%, and most preferably more than 98%, e.g. more than 99% or even 100%. "Neutralizing" herein means that the antibody opsonizes the virus so that it cannot infect any further cell. An assay for testing whether an antibody in a concentration of at most 20 nM is capable of neutralizing a defined amount of HSV of 100 TCID$_{50}$ is provided in Eis-Hübinger et al., 1991, and Eis-Hübinger et al., 1993, and in Examples 1 and 2 below.

Moreover, in one preferred embodiment, the antibody comprises of an amino acid sequence with at least 70%, preferably at least 75%, at least 80%, more preferably at least 85%, at least 90%, even more preferably at least 95%, and most preferably 98% (overall) sequence identity in the framework regions compared to the amino acid residues shown in positions 1 to 30, 38 to 51, 68 to 99, and 112 to 122 (or positions 1 to 30, 36 to 49, 66 to 94, and 103 to 113 according to the numbering by Kabat, respectively) of SEQ ID NO: 9 and in positions 1 to 23, 40 to 54, 62 to 93, and 103 to 113 (or positions 1 to 23, 35 to 49, 57 to 88, and 98 to 108 according to the numbering by Kabat, respectively) of SEQ ID NO: 10, as illustrated in FIG. 4.

```
SEQ ID NO: 9:
QVTLKESGPG ILLPSQTLSL TCSFSGFSLS TSGMSVGWIR

QPSGKGLEWL GHIWWNNDKY YKPALKSRLT ISKDTSNKQV

FLKIASVVTA DTATYYCARI YYGYRPYAMD YWGQGTSVTV SS

SEQ ID NO: 10:
DVLMTQTPLS LPVSLGDQAS ISCRSSQSIV HSNGNTYLEW

YLQKPGQSPK LLIYKVSNRF SGVPDRFSGS GSGTDFTLKI

SRVEAEDLGV YYCFQGSHVP WSFGGGTKLE IKR
```

A polypeptide has "at least X % sequence identity" in the framework regions to SEQ ID NO: 9 or 10, if SEQ ID NO: 9 or 10 is aligned with the best matching sequence of a polypeptide of interest, and the amino acid identity between those two aligned sequences is at least X % over positions 1 to 30, 38 to 51, 68 to 99, and 112 to 122 (or positions 1 to 30, 36 to 49, 66 to 94, and 103 to 113 according to the numbering by Kabat, respectively) of SEQ ID NO: 9 and positions 1 to 23, 40 to 54, 62 to 93, and 103 to 113 (or positions 1 to 23, 35 to 49, 57 to 88, and 98 to 108 according to the numbering by Kabat, respectively) of SEQ ID NO: 10. Such an alignment of amino acid sequences can be performed using, for example, publicly available computer homology programs such as the "BLAST" program provided on the National Centre for Biotechnology Information (NCBI) homepage at http://www.ncbi.nlm.nih.gov/blast/blast.cgi, using the default settings provided therein. Further methods of calculating sequence identity percentages of sets of amino acid sequences or nucleic acid sequences are known in the art.

Alternatively, in another preferred embodiment, the antibody comprises of an amino acid sequence with at least 80%, preferably at least 85%, more preferably at least 90%, even more preferably at least 95%, such as 98%, and most preferably 100% (overall) sequence identity in the framework regions compared to the amino acid residues shown in positions 1 to 30, 38 to 51, 68 to 99, and 112 to 122 (or positions 1 to 30, 36 to 49, 66 to 94, and 103 to 113 according to the numbering by Kabat, respectively) of SEQ ID NOs: 7 and positions 1 to 23, 41 to 55, 63 to 94, and 104 to 114 (or positions 1 to 23, 35 to 49, 57 to 88, and 98 to 108 according to the numbering of Kabat, respectively) of SEQ ID NO: 8, as illustrated in FIG. 4. A polypeptide has "at least X % sequence identity" in the framework regions to SEQ ID NO: 7 or 8, if SEQ ID NO: 7 or 8 is aligned with the best matching sequence of a polypeptide of interest, and the amino acid identity between those two aligned sequences is at least X % over positions 1 to 30, 38 to 51, 68 to 99, and 112 to 122 (or positions 1 to 30, 36 to 49, 66 to 94, and 103 to 113 according to the numbering by Kabat, respectively) of SEQ ID NO: 7 and positions 1 to 23, 41 to 55, 63 to 94, and 104 to 114 (or positions 1 to 23, 35 to 49, 57 to 88, and 98 to 108 according to the numbering by Kabat, respectively) of SEQ ID NO: 8.

SEQ ID NO: 7 and 8 are derived from human germline sequences. Even though non-germline human immunoglobulin framework sequences are of human origin, it can generally not be excluded that they are not immunogenic. Therefore, the present inventors looked at germline sequences, since they are not hypermutated and, therefore, expected not to be immunogenic. Accordingly, the humanized antibody is preferably derived from a human germline sequence, e.g. from SEQ ID NO: 7 and/or 8. SEQ ID NO: 7 and 8 are as follows:

```
SEQ ID NO: 7:
QVTLKESGPA LVKPTQTLTL TCTFSGFSLS TSGMRVSWIR

QPPGKALEWL ARIDWDDDKF YSTSLKTRLT ISKDTSKNQV

VLTMTNMDPV DTATYYCARX XXXXXXXYFD YWGQGTLVTV SS

SEQ ID NO: 8:
DIVMTQTPLS LPVTPGEPAS ISCRSSQSLL DSDDGNTYLE

WYLQKPGQSP QLLIYTLSYR ASGVPDRFSG SGSGTDFTLK

ISRVEAEDVG VYYCMQRIEF PWTFGQGTKV EIKR
```

In the context of the present invention, it has been determined that by using SEQ ID NO:7 and 8 for the generation of the humanized antibody of the invention, no back mutations are required in order to achieve the same affinity as for the parent antibody, which may imply that the corresponding humanized antibody exhibits a very low immunogenicity. Consequently, in the context of the present invention preferably those antibodies are included, which show the same specificity than the antibody comprising SEQ ID NOs: 9 and 10 or SEQ ID NOs 7 and 8, respectively.

In a further preferred embodiment, the antibody is conjugated to an effector moiety, a therapeutic moiety, or a detectable moiety. In this context, the term "conjugated" refers to any method known in the art for functionally connecting protein domains, including without limitation recombinant fusion with or without intervening domains, intein-mediated fusion, non-covalent association, and covalent bonding, e.g., disulfide bonding peptide bonding, hydrogen bonding, electrostatic bonding, and conformational bonding, e.g., biotin-avidin associations. The conjugation to an effector moiety can be either by chemical or recombinant means. Chemical means refers to a reaction between the antibody and the effector moiety such that there is a covalent bond formed between the two molecules to form one molecule.

The term "effector moiety" means a compound intended to have an effect on a cell targeted by the antibody. The effector moiety may be, for example, a therapeutic moiety or a detectable moiety.

A "therapeutic moiety" is a compound intended to act as a therapeutic agent, such as a cytotoxic agent or drug. Examples of compounds are given below for the pharmaceutical composition.

A "detectable label" includes any compound or protein-tag detectable by spectroscopic, photochemical, biochemical, immunochemical, electrical, optical or chemical means, such as a fluorescent label.

The specificity of an antibody may be expressed either by the CDRs or by the epitope to which the antibody is bound. Accordingly, in a second aspect, the invention relates to an antibody which recognizes the same epitope as the antibody of the first aspect. As shown in the Examples section and as illustrated in FIGS. 13A and 13B, this epitope is a discontinuous or rather a pseudocontinuous epitope partially resistant to denaturation located at the amino acids 172-195 and 295-313 of glycoprotein B of HSV1 and HSV2.

In the context of the present application, the epitope of the mAb 2c antibody may be located within the first 487 amino-terminal residues of the gB protein. Preferably, the epitope may comprise at least one amino acid sequence located within the amino acid sequence between position 172 and 307 of the gB protein.

The epitope may comprise the consecutive amino acid sequence $_{301}$YGYRE$_{305}$ of the gB protein, preferably the consecutive amino acid sequence $_{301}$YGYREG$_{306}$ or $_{300}$FYGYRE$_{305}$, more preferably the sequence may be further extended at the termini (i.e., $_{299}$PFYGYRE$_{305}$ or $_{300}$FYGYREGS$_{307}$). The epitope of the antibodies of the present invention may comprise the consecutive amino acid sequence 298-313 ($_{298}$SPFYGYREGSHTEHTS$_{313}$) of gB. Alternatively, the epitope may be located in the consecutive amino acid sequence $_{172}$QVWFGHRYSQFMGIFED$_{188}$. The epitope may comprise the consecutive amino acid sequence $_{172}$QVWFGHRYSQFMG$_{184}$.

Preferably, the epitope may be consisted of more than one consecutive amino acid sequences. The epitope may partly be a discontinuous epitope. More preferably, the epitope may comprise two consecutive amino acid sequences. Such an epitope consisting of two amino acid sequences may be designated as "duotope". The antibody may bind to both amino acid sequences.

More preferably, the amino acid sequences of the duotope may comprise the amino acid sequence $_{300}$FYGYRE$_{305}$ and an amino acid sequence located between amino acid position 172 and 188. Even more preferably, the epitope may comprise the amino acid sequence $_{300}$FYGYRE$_{305}$ and amino acid sequence $_{179}$YSQFMG$_{184}$ of the gB protein. Alternatively, the epitope or the duotope may be chemically synthesized. The epitope may be an chemically synthesized epitope having the sequence YSQFMG-βA-FYGYRE. The abbreviation βA as used herein refers to beta-alanine.

Most preferably, the epitope may comprise the amino acid sequence FYGYRE and amino acid sequence FED of the gB protein. The epitope may be a chemically synthesized epitope having the sequence FED-βA-βA-FYGYRE or PFYGYREGFEDF.

It may be understood by a person skilled in the art that the epitopes may be comprised in the gB protein, but may also be comprised in a degradation product thereof or may be a chemically synthesized peptide. The amino acid positions are only indicated to demonstrate the position of the corresponding amino acid sequence in the sequence of the gB protein. The invention encompasses all peptides comprising the epitope. The peptide may be a part of a polypeptide of more than 100 amino acids in length or may be a small peptide of less than 100, preferably less than 50, more preferably less than 25 amino acids, even more preferably less than 16 amino acids. The amino acids of such peptide may be natural amino acids or nonnatural amino acids (e.g., beta-amino acids, gamma-amino acids, D-amino acids) or a combination thereof. Further, the present invention may encompass the respective retro-inverso peptides of the epitopes. The peptide may be unbound or bound. It may be bound, e.g., to a small molecule (e.g., a drug or a fluorophor), to a high-molecular weight polymer (e.g., polyethylene glycol (PEG), polyethylene imine (PEI), hydroxypropylmethacrylate (HPMA), etc.) or to a protein, a fatty acid, a sugar moiety or may be inserted in a membrane.

In contrast to the antibody H126 known in the art, the epitope recognised by the mAb 2c antibody of the present invention is not essentially discontinuous. In contrast to H126, the antibody of the present invention can bind to a continuous epitope, thus a consecutive amino acid sequence or may bind to a discontinuous eptitope. Therefore, the properties of the antibody of the present invention are improved. For instance, the mAb 2c antibody can be used for methods in which the target protein is denatured (e.g., SDS page electrophoresis) or for the detection of small linear peptides.

In order to test whether an antibody in question and the antibody of the first aspect recognize the same epitope, the following competition study may be carried out: Vero cells infected with 3 moi (multiplicity of infection) are incubated after 20 h with varying concentrations of the antibody in question as the competitor for 1 hour. In a second incubation step, the antibody of the first aspect is applied in a constant concentration of 100 nM and its binding is flow-cytometrically detected using a fluorescence-labelled antibody directed against the constant domains of the antibody of the first aspect (see also the Examples section and FIG. 6). Binding that conducts anti-proportional to the concentration of the antibody in question is indicative for that both antibodies recognize the same epitope. However, many other assays are known in the art which may be used. The preferred embodiments of the second aspect are the same as for the first aspect, as described above.

In a third aspect, the invention relates to a pharmaceutical composition, comprising an effective amount of the antibody according to the first or second aspect and at least one pharmaceutically acceptable excipient. However, the term "pharmaceutical composition" may be used interchangeably herein with the term "drug".

The content of the antibody in the pharmaceutical composition is not limited as far as it is useful for treatment or prevention, but preferably contains 0.0000001-10% by weight per total composition. Further, the antibody described herein is preferably employed in a carrier. The choice of carrier may depend upon route of administration and concentration of the active agent(s) and the carrier may be in the form of a lyophilised composition or an aqueous solution. Generally, an appropriate amount of a pharmaceutically acceptable salt is used in the carrier to render the composition isotonic. Examples of the carrier include but are not limited to saline, Ringer's solution and dextrose solution. Preferably, acceptable excipients, carriers, or stabilisers are non-toxic at the dosages and concentrations employed, including buffers such as citrate, phosphate, and other organic acids; salt-forming counter-ions, e.g. sodium and potassium; low molecular weight (>10 amino acid residues) polypeptides; proteins, e.g. serum albumin, or gelatine; hydrophilic polymers, e.g. polyvinylpyrrolidone; amino acids such as histidine, glutamine, lysine, asparagine, arginine, or glycine; carbohydrates including glucose, mannose, or dextrins; monosaccharides; disaccharides; other sugars, e.g. sucrose, mannitol, trehalose or sorbitol; chelating agents, e.g. EDTA; non-ionic surfactants, e.g. Tween, Pluronics or polyethylene glycol; antioxidants including methionine, ascorbic acid and tocopherol; and/or preservatives, e.g. octadecyldimethylbenzyl ammonium chloride; hexamethonium chloride; benzalkonium chloride, benzethonium chloride; phenol, butyl or benzyl alcohol; alkyl parabens, e.g. methyl or propyl paraben; catechol; resorcinol; cyclohexanol; 3-pentanol; and m-cresol). Suitable carriers and their formulations are described in greater detail in Remington's Pharmaceutical Sciences, 17th ed., 1985, Mack Publishing Co.

The composition may also contain more than one active compound such as a chemotherapeutic agent or a virusstatic agent, including acyclovir, penciclovir, idoxuridin and foscarnet.

Acyclovir, also known as acycloguanosine (ACV) or 2-Amino-9-(2-hydroxyethoxymethyl)-3H-purin-6-on, is a guanosine analogue antiviral drug, marketed under trade names such as, ACERPES®, Acic®, Aciclobeta®, AcicloCT®, Aciclostad®, Aciclovir, Acic®, Ophtal®, Acivir®, AciVision, Acyclovir®, Aviral®, Cyclovir, Helvevir®, Herpex, Supraviran®, Virucaim®, Virupos® Virzin, Zoliparin®, Zovir, and Zovirax®. Penciclovir (2-amino-9-[4-hydroxy-3-(hydroxymethyl)butyl]-6,9-dihydro-3H-purin-6-on) is a guanine analogue antiviral drug, marketed under trade names such as Denavir and Fenistil. Famciclovir (2-[(acetyloxy) methyl]-4-(2-amino-9H-purin-9-yl)butyl acetate) is a prodrug of penciclovir with improved oral bioavailability. Idoxuridin (2'-Desoxy-5-ioduridin) is a biochemical analogue of the nucleoside uridine and marketed under trade names such as Virunguent® and Zostrum®. Foscarnet is the conjugate base of the chemical compound with the formula $HO_2CPO_3H_2$ and is marketed under the trade names Foscavir® and Triapten®.

Preferably, the antibody and/or the active compound are included in an effective amount. The term "effective amount" refers to an amount sufficient to induce a detectable therapeutic response in the subject to which the pharmaceutical composition is to be administered.

In a fourth aspect, the invention provides an expression vector, comprising a nucleic acid sequence which encodes the antibody of the invention. Generally, expression vectors are plasmids which are used to introduce a gene in question into a target cell, resulting in the transcription and translation of the protein encoded by the gene, i.e. the antibody. Thus, the expression vector contains regulatory sequences such as promoter and enhancer regions, as well as a polyadenylation signal site in order to direct efficient transcription of the gene carried on the expression vector. The expression vector may also comprise further necessary or useful regions, e.g. a selectable marker for selection in eukaryotic or prokaryotic cells, an origin of replication, etc.

Consequently, in a fifth aspect the invention relates to a host cell, comprising a nucleotide sequence which encodes the antibody of the invention. The host cell may be any cell suitable for expressing the antibody of the invention and includes mammalian cells, yeast cells, and insect cells, preferably mammalian cells, more preferably immortal cell lines such as myeloma cell lines. Suitable cell lines are available at the American Tissue Culture Collection, ATCC.

Moreover, in a sixth aspect, a hybridoma cell, capable of producing the antibody of the first and/or second aspect is provided. Hybridoma cells are engineered cells capable of multiplying rapidly and indefinitely, producing a desired antibody in large amounts. Hybridoma cells are prepared by removing antibody producing B-cells from the spleen of an animal that has been challenged with the relevant antigen, which are then fused with immortal myeloma tumor cells.

In a very important seventh aspect, the invention relates to an antibody according to the invention for use as a drug. More particularly, the invention relates to a use of the antibody of the invention for the manufacture of a drug for the prophylactic or therapeutic treatment of HSV-associated diseases in a subject. Equally, the invention relates to the antibody of the invention for use in the prophylactic or therapeutic treatment of HSV-associated diseases in a subject. Furthermore, the present invention relates to a method of the prophylactic or therapeutic treatment of HSV-associated diseases in a subject, wherein the antibody of the invention is administered to a subject in a therapeutically effective amount. HSV infection may cause several distinct diseases. Common infection of the skin or mucosa may affect the face and mouth (orofacial herpes), genitalia (genital herpes), or hands (herpes whitlow). More serious disorders occur when the virus infects and damages the eye (herpes keratitis), or invades the central nervous system, damaging the brain (herpes encephalitis). Patients with immature or suppressed immune systems, such as newborns, transplant recipients, or AIDS patients are prone to severe complications from HSV infections. HSV-associated diseases also include herpes gladiatorum, Mollaret's meningitis, possibly Bell's palsy, disorders being associated with cognitive deficits of bipolar disorder, also known as manic depression, manic depressive disorder or bipolar affective disorder, and Alzheimer's disease. With regard to Alzheimer's disease, recent scientific publications demonstrated a striking localization of herpes simplex virus type 1 DNA within the beta-amyloid plaques, suggesting that this virus may be a cause of the plaques. Finally, the use of the antibody according to the invention is useful if the development of resistant strains against common chemotherapeutic virustatic agents is observed, e.g. during long-lasting prophylactical and therapeutical treatment of immunosuppressed patient.

Thus, in a preferred embodiment, the HSV-associated disease is accompanied with one or more of the following features: presence of an oral recidive, presence of a genital recidive, eczema herpeticatum, herpes neonatorum, immune deficiency (immunocompromized patients), immunosuppression, encephalitis, meningitis, meningoencephalitis, eye infections, generalised HSV infections and/or resistance against a virusstatic agent.

In an alternative preferred embodiment, the HSV-associated disease is accompanied with intolerance towards a chemotherapeutic virustatic agent.

In a further preferred embodiment, the drug comprises at least one further active agent, preferably wherein the further active agent is a chemotherapeutic agent or a virusstatic agent, more preferably wherein the further active agent is selected from the group consisting of acyclovir, penciclovir, idoxuridin and foscarnet, as described above.

In a final preferred embodiment the subject is a mammal such as a dog, cat, pig, cow, sheep, horse, rodent, e.g. rat, mouse, and guinea pig, or a primate, e.g. gorilla, chimpanzee, and human, preferably the subject is a human.

DESCRIPTION OF THE FIGURES

FIG. 4 shows a sequence alignment of the variable heavy and light chain domain ($V_H$ and $V_L$). The antigen binding site is defined according to Chothia (Chothia and Lesk, 1987; Chothia et al., 1989) (dotted line) and Kabat (Kabat and Wu, 1991) (dashed line). The Human germline sequences DP28 and DPK13 were taken from the V-Base database (http://vbase.mrc-cpe.cam.ac.uk/) and served as acceptor sequences for the CDRs of the murine mAb 2c. (A) "invariant residues" (Kabat and Wu, 1991); (B) "key residues" (Chothia et al., 1989) and (C) residues at the $V_H/V_L$ interface (Chothia et al., 1985) are marked with (+) for matching or (−) for non-matching residues between murine and human sequence, respectively. (D) Residues at core sites as defined by Chothia (Chothia et al., 1998) as invariant (i) residue sites; similar (r) residue sites; surface (s) residues R,K,E,D,Q,N; neutral (n) residues P,H,Y,G,A,S,T; and buried (b) residues C,V,L,I,M, F,W respectively; buried neutral residues are marked by x; surface neutral residues are marked by y; non-matching residue sites between murine and human sequence are marked in bold letters; VHhum2c and VLhum2c, specificity grafted sequences with murine CDR residues shown in bold letters. All residues are shown in the single letter code and numbered according to Kabat (Kabat et al., 1991).

FIG. 23 shows the peptide scanning on the HSV-1 gB sequence from amino acid 296 to 315. Cellulose membrane-bound 13-mer peptides, each peptide shifting along the sequence by one amino acid (13/12 scan) and synthesised in duplicate, were incubated with MAb 2c followed by chemiluminescence western blotting detection. Binding of MAb 2c was observed to a series of five peptides. The sequence common to the five reactive peptides is $_{300}$FYGYREGSH$_{308}$.

FIG. 24 shows the key motif scan on the gB sequence from residue 295 to 315. The HSV-1 gB sequence from amino acid 295 to 315 was dissected into hexameric peptides, each shifting along the sequence by one amino acid, resulting in a total of 16 peptides. The gB-derived sequence was framed by four randomized residues at each, N- and C-terminus. Two consecutive peptides representing gB sequence $_{300}$FYGYRE$_{305}$ and $_{301}$YGYREG$_{306}$ were identified to bind MAb 2c. The sequence common to these peptides is highlighted in bold letters (peptide 6 & 7).

EXAMPLES

The present invention is further described by the following examples which should not be construed as limiting the scope of the invention.

Example 1

Preparation of a Murine Monoclonal Antibody (mAb) 2c with Specificity for Glycoprotein B (gB) of Herpes Simplex Virus Type 1 and Type 2 (HSV1, HSV2)

For the generation of an anti-HSV specific mAb, BALB/c mice have been immunized with the UV-inactivated HSV1-strain 342 hv. Subsequently murine splenocytes were immortalized by somatic fusion to the myeloma cell line X63-Ag8.653 and a hybridoma cell line secreting the anti-HSV-specific mAb 2c (IgG2a) was isolated by screening the supernatants of single cell clones using enzyme immunoassays, immunofluorescence assays as well as HSV-neutralization assays. Binding studies revealed that mAb 2c recognizes a shared, discontinuous epitope of glycoprotein gB of HSV1 and HSV2. Glycoprotein B is about 904 amino acids long and is integrated as a trimer in the viral membrane and in the membrane of HSV1/2 infected cells. It is of particular relevance that mAb 2c not only neutralizes the spreading of extracellular viral particles, but also effectively inhibits the direct pathway of infection from the initially infected cell to adjacent non-infected cells (cell-to-cell spread), which is characteristic for HSV. The latter process is usually not to be inhibited by the naturally occurring HSV-specific antibody repertoire in humans.

Figure 1:
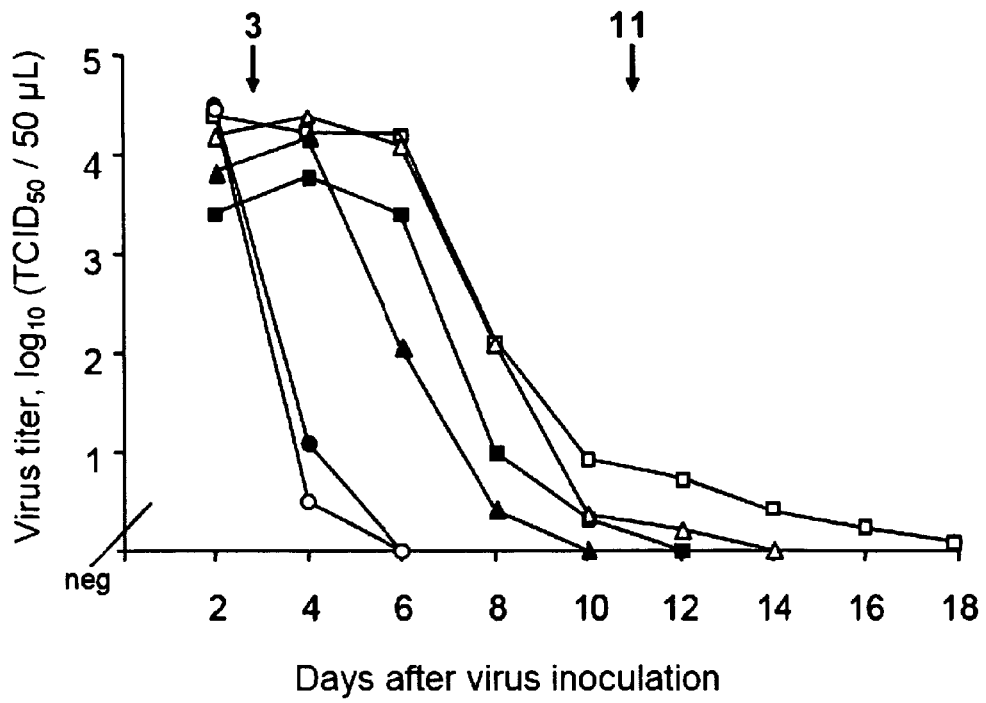
FIG. 1 shows the reduction of HSV replication in vivo by administration of the monoclonal antibody (mAb) 2c after established infection in the vaginal mucous membrane. Immunocompetent (filled symbols) and $CD4^+$ depleted (open symbols) mice were treated on day 3 and 11 post infection (arrows) by intraperitoneal injection (i.p.) with polyclonal HSV immune serum (triangles), with the mAb 2c (circles), or control culture medium (squares).

In order to examine the in vivo efficacy of the mAb 2c, a pathway of infection in the mouse model has been chosen, which closely resembles the natural infection relations in human. Therefore, C57BL/6J mice were infected by application of the HSV1 strain 342 hv on the intact vaginal mucosa membrane. For inhibition of HSV replication in vivo, mAb 2c was intraperitoneally (i.p.) administered to mice at different time points post infection. In both immunocompetent and CD4+ T cell depleted animals, mAb 2c is capable of inhibiting the viral propagation in the vaginal mucosa membrane and the formation of inflammatory lesions within a short period of time (FIG. 1).

Figure 2A:
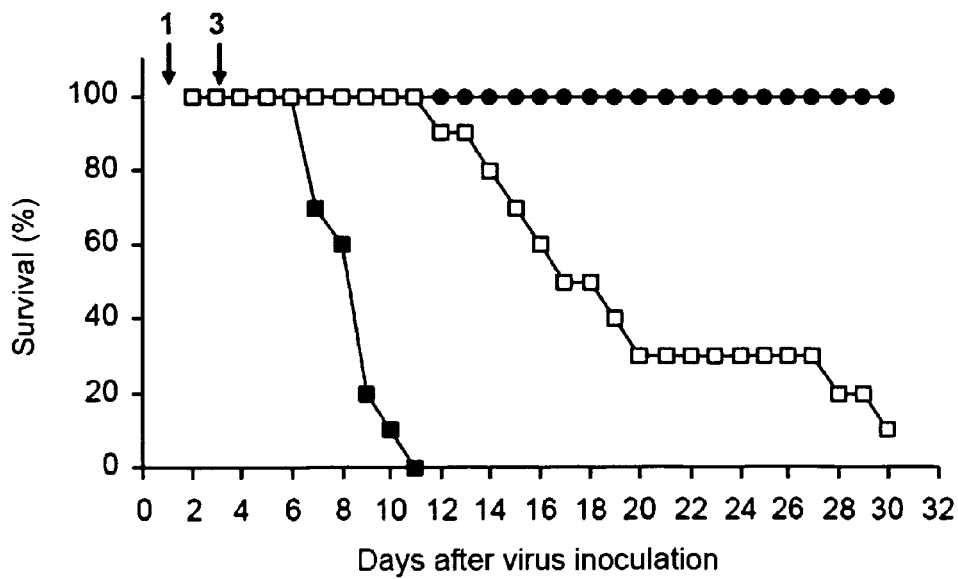
FIG. 2 shows the effect of mAb 2c on the progression of HSV infection in immunosuppressed ($CD4^-/CD8^-$) mice. At day 1 and 3 post infection (indicated by arrows), the animals were administered i.p. either control medium (filled squares), polyclonal HSV immune serum (open squares), or mAb 2c (filled circles). (A) shows the survival rate and (B) the viral replication in the vaginal mucous membrane.
Figure 2B:
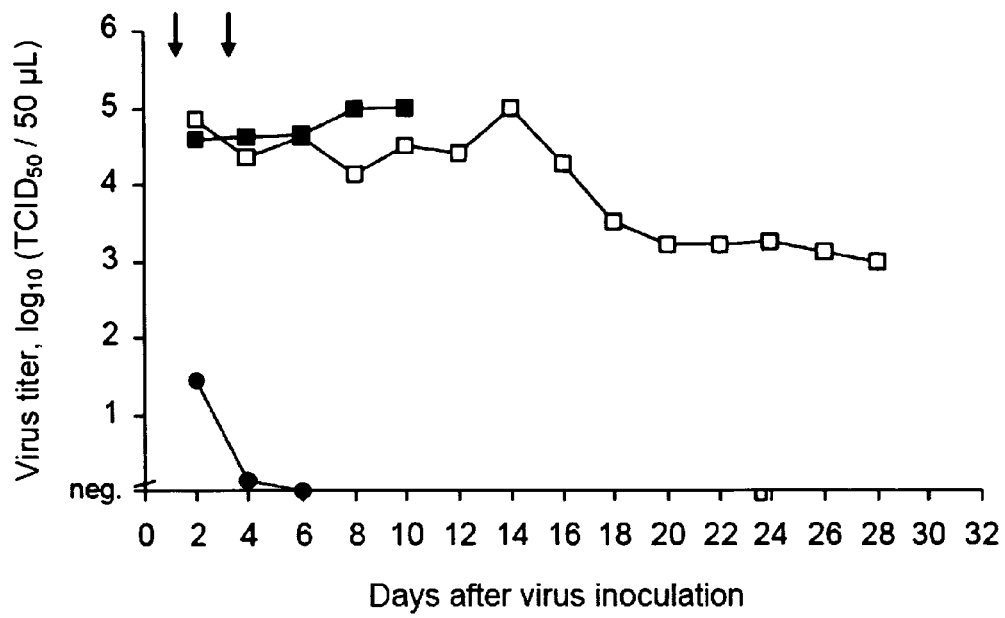

In contrast to polyclonal HSV serum, mAb 2c was capable to inhibit viral replication as well as to prevent a generalized, lethal progressing disease with a high efficiency in immunosuppressed animals with completely depleted T cells (CD4+ and CD8+) (FIG. 2). Administration of mAb 2c 24h prior to viral inoculation efficiently protected the animals against infection (Eis-Hübinger et al., 1993).

In order to examine the influence of the number of antigen binding sites (valency) and the Fc-part on the neutralizing properties, Fab- and F(ab')$_2$-fragments of the mAb 2c were generated by conventional protease digestion as well as a recombinant "single chain Fv" (scFv) of mAb 2c was cloned, produced and purified (FIG. 3) using methods well known in the art.

The affinity constants ($K_D$) were determined flow cytometrically using HSV-infected Vero cells expressing the gB-protein as membrane associated glycoprotein on the cell surface during the natural HSV replication cycle, as a method well known in the art. The results are shown in Table 1 below.

TABLE 1

Affinity constants ($K_D$) of the murine mAb 2c and of the generated 2c antibody fragments

| | Strain: | | | |
|---|---|---|---|---|
| | HSV-1 F | | | HSV-2 G |
| | Valency: | | | |
| | bivalent | monovalent | | bivalent |
| | 2c IgG | 2c-F(ab')$_2$ | 2c-Fab | 2c-scFv | 2c IgG |
| $K_D$ [nM] | 10 | 7 | 17 | 19 | 10 |

In comparison to the parenteral mAb 2c, the F(ab')$_2$-fragment exhibits a slightly increased affinity. The Fab- and scFv-fragments have an almost identical affinity, which is, however, due to their monovalency about 1.7- to 1.9-fold weaker than the affinity of the parenteral mAb.

Neutralizing activity of antibodies were determined by a standard end-point dilution assay using Vero cells grown as monolayers in microtiter plates. Briefly, 100 TCID$_{50}$ of HSV were pre-incubated in 100 μl cell culture medium for 1 h at 37° C. with serial dilutions of antibodies (2c-IgG and F(ab)$_2$: 0.98 nM-125 nM; Fab: 23 nM-3000 nM) before inoculation of Vero cells. After 72 h incubation at 37° C. the antibody concentration required to prevent the formation of virus-induced CPE to 100% was determined as complete neutralization titer. In addition, virus neutralization capacity of monovalent 2c-Fab fragments were determined in the presence of cross-linking antibodies.

TABLE 2

Complete neutralization of a defined virus amount of 100 TCID$_{50}$

| | Strain: | | | | | |
|---|---|---|---|---|---|---|
| | HSV-1 F | | | HSV-2 G | | |
| | Valency: | | | | | |
| | bivalent | | monovalent | bivalent | | monovalent |
| | 2c IgG | 2c-F(ab')$_2$ | 2c-Fab | 2c IgG | 2c-F(ab')$_2$ | 2c-Fab |
| Concentration [nM] | 8 | 4 | 3000 | 31 | 16 | 3000 |

It could be demonstrated that the parenteral mAb 2c and its F(ab')$_2$- and Fab-fragments are capable of complete neutralization of HSV1 and HSV2. However, the monovalent antibody fragments show a significantly reduced neutralization efficiency for HSV1/2 in comparison to mAb 2c. A 375-fold and 97-fold higher concentration of the Fab-fragment is necessary for 100% neutralization of HSV1 and HSV2, respectively. The scFv showed a plaque reductive effect but was not able to fully inhibit CPE at the highest tested concentration of 3000 nM (data not shown). The viral neutralization capacity of the monovalent 2c Fab-fragment could be enhanced two-fold by adding an excess of an anti-Fab specific IgG (Jackson ImmunoResearch, Newmarket, England) to the pre-incubation step (not shown). In contrast, the bivalent F(ab')$_2$-fragment exhibits a virtually two times more efficient neutralization activity for both HSV1 and HSV2 in comparison to the parenteral mAb 2c. In conclusion, the antibody valency plays an important role for its neutralization properties. The higher antibody concentrations required for complete neutralization of HSV-2 can be explained a greater quantity of non-infectious particles produced by HSV-2 compared to HSV-1, as confirmed by RT-PCR determining the DNA copy numbers for HSV-1 and HSV-2 (data not shown).

Further details for the properties of mAb 2c and its production are provided in Eis-Hübinger et al., 1991, and Eis-Hübinger et al., 1993.

Example 2

Chimerization and Humanization of mAb 2c

Figure 3:
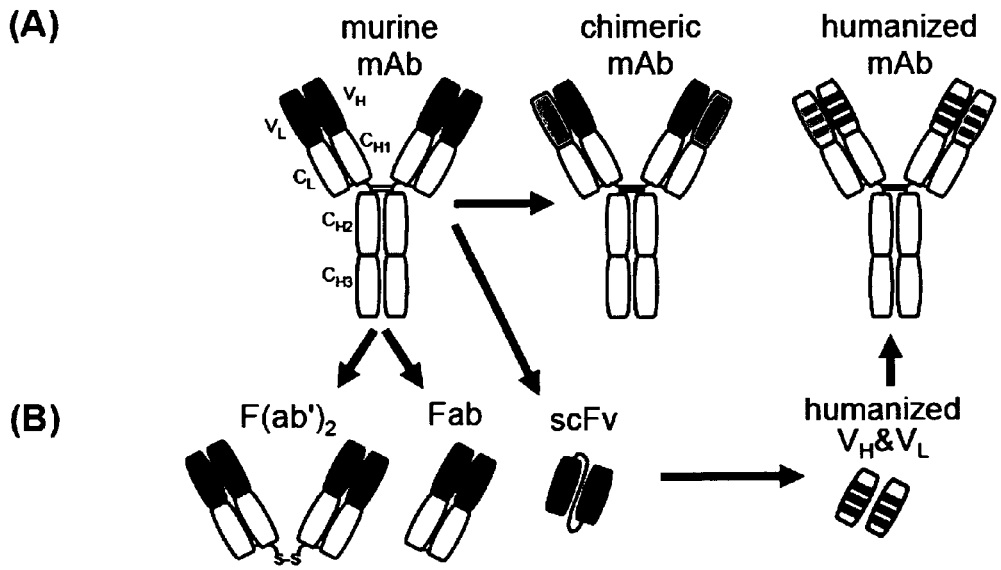
FIG. 3 is a schematic presentation of the mAb 2c derived antibodies and antibody fragments. (A) Complete antibodies: Genetic fusion of murine variable regions ($V_L$, $V_H$; left) to human constant domains ($C_L$, $C_{H1}$, $C_{H2}$, $C_{H3}$; middle) results in a chimeric antibody. In a humanized IgG antibody (right), the hypervariable regios of a murine monoclonal antibody are grafted onto the framework of a human antibody. (B) Antibody fragments: Monovalent Fab fragments (Fab), consisting of the light chain ($V_L+C_L$) and the two N-terminal domains of the heavy chain ($V_H+C_{H1}$), or bivalent $F(ab')_2$ fragments, which are covalently linked by two unpaired C-terminal cysteine residues, can be produced by way of conventional protease digestion. For the generation of the murine scFv antibody ("single chain fragment variable"), the genes coding for the variable domains $V_H$ and $V_L$ were isolated from the 2c hybridoma cell line and linked by a gene segment coding for a flexible linking peptide ("linker").

In order to utilize the murine monoclonal antibody 2c as a therapeutic agent, the antibody was modified using methods of genetic engineering with the aim to reduce or eliminate its immunogenicity during administration to humans, while fully retaining the specificity of the parental antibody. Accordingly, a chimeric and a humanized monoclonal antibody having the same specificity of the mAb 2c were generated (FIG. 3).

First, the authentic genes of the variable heavy and light chain ($V_H$, $V_L$) of the mAb 2c were isolated and amplified from the hybridoma cell line using 5'-RACE (Rapid Amplification of cDNA Ends)-PCR. A chimeric IgG1-antibody (ch2c) was generated by cloning the amplified $V_H$- and $V_L$- genes in expression vectors constructed by our cooperation partner Dr. Grosse-Hovest (Universität Tübingen), which contains the constant regions of the light chain and heavy chain of a human IgG1 isotype. The antibody was finally secreted into cell culture supernatants of stably transfected Sp2/0 murine myeloma cells.

In order to further reduce the immunogenicity, a humanized antibody was constructed. Therefore, the six complementarity determining regions (CDRs) coding gene segments of the mAb 2c (2c $V_L$-CDR1/2/3 and 2c $V_H$-CDR1/2/3) were cloned into suitable human framework immunoglobulin acceptor scaffolds of the human $V_H$ and $V_L$ germline genes, respectively (CDR grafting). Suitable human germline acceptor scaffolds for cloning the CDR-regions of the light chain and the heavy chain of the mAb 2c were determined by sequence alignment with the corresponding human framework regions of the V-Base database (http://vbase.mrc-cpe.cam.ac.uk/). DP28 showed the highest framework sequence identity to the corresponding murine mAb 2v heavy chain $V_H$ sequence (88.5% sequence identity); DPK13 showed the highest framework sequence identity to the corresponding murine mAb 2c light chain $V_L$ sequence (88.9% sequence identity). Thus, the CDR coding gene segments of the murine donor-antibody 2c (i.e. 2c $V_L$-CDR1/2/3 and 2c $V_H$-CDR1/2/3) were cloned into acceptor frameworks coding for DP28 and DPK13, respectively.

Figure 4:
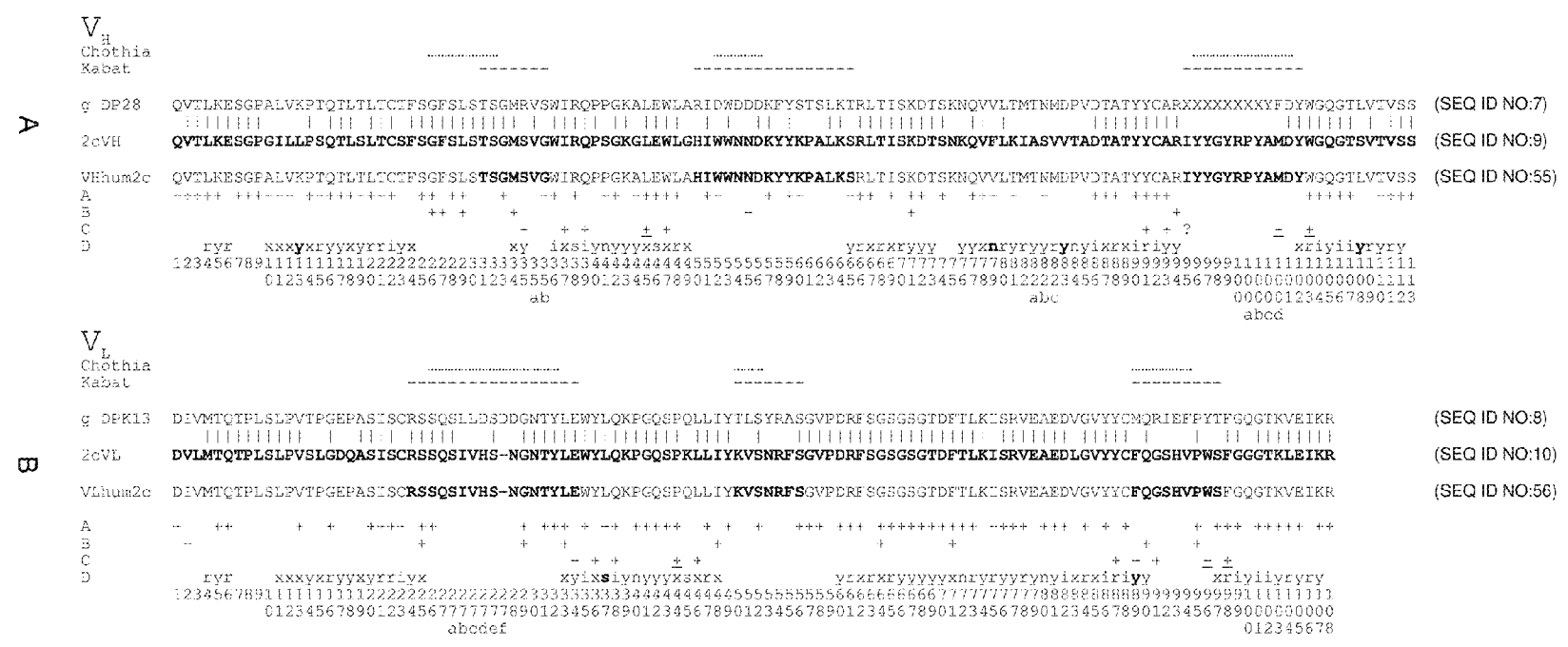

In the context of humanizing monoclonal antibodies, it is necessary to identify those amino acids in the human framework regions, which might be detrimental to the structural integrity of the introduced murine CDRs and thus to the antigen binding properties. Normally, such amino acids are identified using computer-generated homology models, and positions that appear to be sterically crucial are mutated to the corresponding murine sequence, in order to retain the antigen binding properties of the murine donor-mAb (c.f. Queen et al., 1989). However, potentially crucial amino acids may also be identified using antibody-repertoire databases and evaluating their critical significance on the basis of reference antibodies with a known three-dimensional structure (c.f. Krauss et al., 2003). Accordingly, several potentially crucial amino acids in the $V_H$- and $V_L$-framework region were determined (FIG. 4) and four humanized mAb 2c variants in which these potentially crucial amino acids were successively backmutated to their corresponding murine residue were generated by overlap extension PCR (see Table 3 below).

TABLE 3

Humanized mAb 2c variants with backmutations in framework regions to murine donor sequence

| Humanized mAb variant | 2c CDR grafting | | Backmutation to the murine 2c framework donor-sequence | |
|---|---|---|---|---|
| | $V_L$ | $V_H$ | $V_L$ | $V_H$ |
| h2c-V1 | CDR1/2/3 | CDR1/2/3 | — | — |
| h2c-V2 | CDR1/2/3 | CDR1/2/3 | — | N76K |
| h2c-V3 | CDR1/2/3 | CDR1/2/3 | — | N76K, V79F |
| h2c-V4 | CDR1/2/3 | CDR1/2/3 | I2V | N76K, V79F |

The humanized antibody variants h2c-V1-4 were constructed by cloning the humanized $V_H$- and $V_L$-genes in the aforementioned expression vector constructed by our cooperation partner Dr. Grosse-Hovest (Universität Tübingen). The antibody was finally expressed after stable transfection of the murine myeloma cell line Sp2/0. After selection of clones with high specific production rates, the antibodies were quantitatively produced and purified from the cell culture supernatant for further characterization.

Characterization of the Chimeric and Humanized anti-HSV IgG1 Antibody

Figure 5:
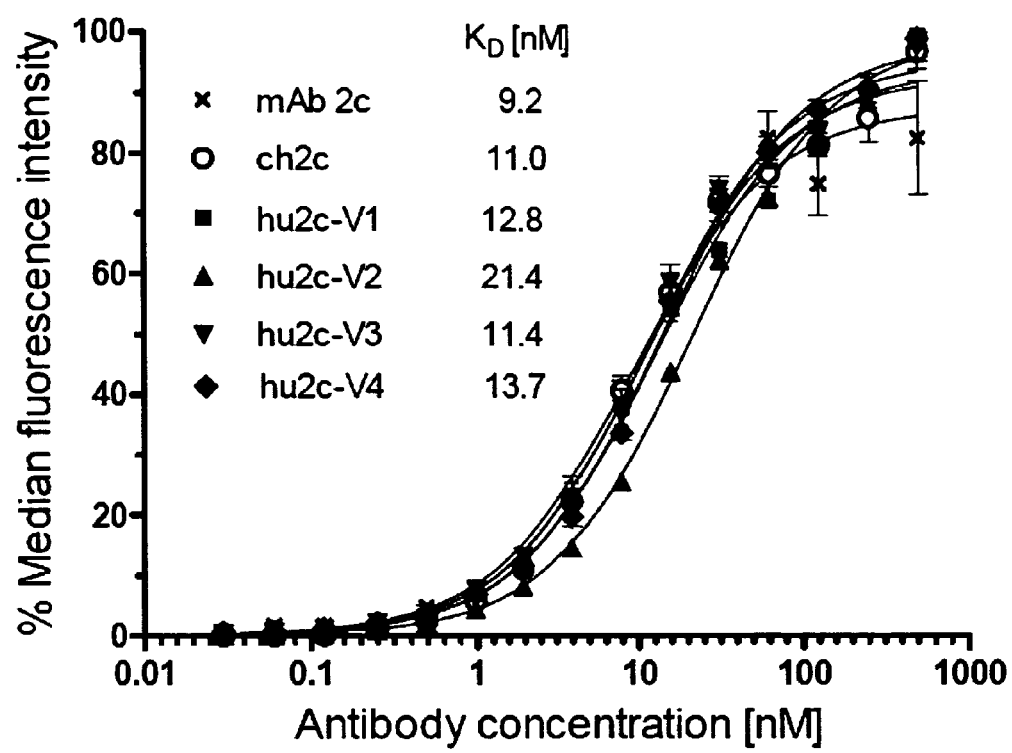
FIG. 5 shows the equilibrium-binding curves of monoclonal antibodies 2c, ch2c and humanized variants hu2c-V1-V4. Specific binding to glycoprotein B on surface of HSV-1 F infected Vero cells was determined by flow cytometry. Binding activity at indicated concentrations is given as median fluorescence intensity (MFI) minus background fluorescence. Measurements were performed in triplicates; standard deviations are shown as bars. Binding affinity constants $K_D$ were determined by fitting the antigen binding data to the nonlinear regression model according to the Levenberg-Marquard method.

The affinity constant ($K_D$) was determined similarily by flow cytometry as described for the parental mAb 2c and the 2c-antibody fragments (c.f. Example 1), using HSV-infected Vero cells. The results are shown in FIG. 5. The chimeric antibody ch2c retained the affinity of the parental antibody mAb 2c. In the case of the humanized variants sole CDR grafting as for variant h2c-V1 was sufficient enough to preserve an affinity comparable to the murine mAb 2c. Therefore further successive backmutations of human framework residues to the respective murine sequence was not necessary to improve the structural integrity of the antigen binding site. Variant h2c-V2 even exhibits a two-fold lower affinity in comparison to mAb 2c.

Figure 6:
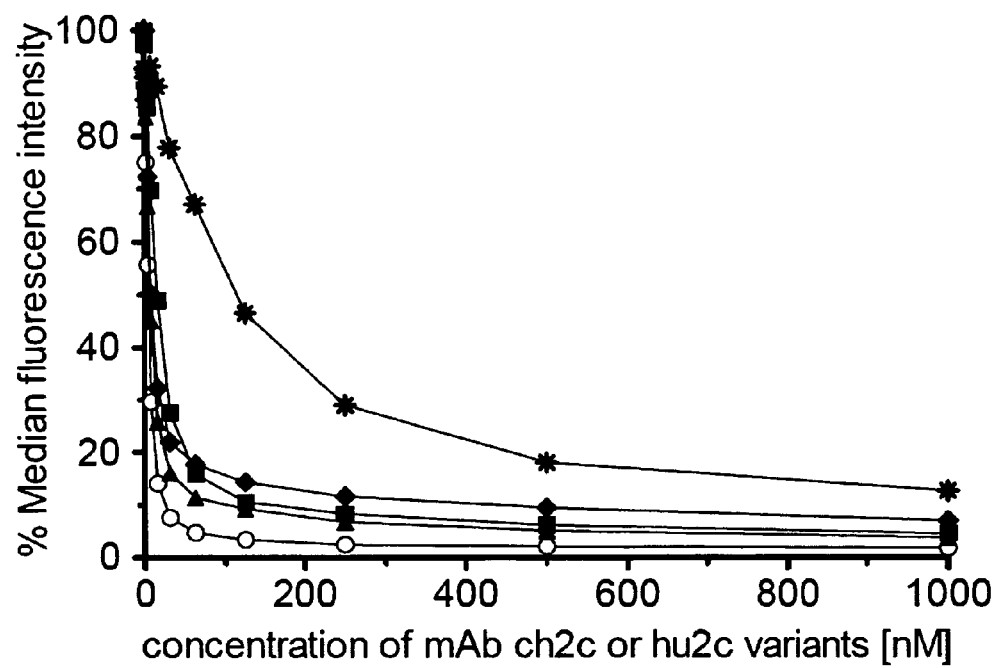
FIG. 6 shows a competition study which demonstrates the same epitope specificity of the chimeric and humanized antibodies as the parental murine mAb 2c. The chimeric mAb ch2c (open circle) and humanized mAb variants hu2c-V1 (square), -V2 (triangle), -V3 (asterisk), -V4 (diamond) compete with the parental mAb 2c for binding to gB present on the surface of HSV-1 infected Vero cells. Infected Vero cells were incubated first with increasing concentrations of either mAb ch2c or humanized mAbs hu2c-V1-V4, followed by incubation with 100 nM of mAb 2c as competitor. The median fluorescence intensity (MFI) shows the binding of the applied competitor.

In order to demonstrate that the chimeric mAb 2c and the humanized antibody variants mAb h2c 1-4 recognize the same epitope than the parental mAb 2c, competition studies were carried out. HSV-1 infected (3 moi, 20 h) Vero cells were incubated first for 1 hour with increasing concentrations of the chimeric mAb ch2c or the humanized mAbs hu2c V1-V4, respectively. In a second incubation step 100 nM of the parental mAb 2c was added and its binding was detected flow-cytometrically using a fluorescence labelled antibody directed against the murine constant domains (FIG. 6).

The competition study shows that the fluorescence signal representing the binding of the competitor is inversely proportional to the concentration of unlabeled antibodies applied in the first incubation step. This proves that the chimeric mAb and the humanized mAb variants compete with mAb 2c for the same specific binding site and hence recognize the same epitope.

The ability of viral neutralization of mAb ch2c and the four humanized variants h2c was examined with purified antibody preparations as described above. The results are shown in Table 4 below. The respective concentrations necessary for 50% and complete HSV neutralization of a defined viral amount of 100 $TCID_{50}$ are indicated.

TABLE 4

Antibody concentrations required for 50% or complete neutralization of a defined viral amount of 100 $TCID_{50}$

| concentration [nM] required for | mAb | | | | | |
|---|---|---|---|---|---|---|
| | 2c | ch2c | h2c-V1 | h2c-V2 | h2c-V3 | h2c-V4 |
| 50% neutralization | 4.3 | 3.5 | 3.7 | 5.1 | 3.3 | 3.7 |
| 100% neutralization | 7.8 | 7.8 | 7.8 | 15.6 | 7.8 | 7.8 |

The chimeric mAb ch2c and all humanized mAbs h2c with the exception of mA h2c-V2 neutralize HSV with the same efficiency than the parenteral mAb 2c. The two-fold reduced neutralization efficiency of mAb h2c-V2 correlates with the lower affinity of this variant. For further experimental characterization and pre-clinical evaluation mAb h2c-V1 was chosen, as this variant possess the same affinity and virus-neutralizing properties as the parental antibody mAb 2c. In addition mAb h2c-V1 has in the framework regions no back-mutations to the murine donor sequence and is therefore expected to possess a low immunogenic potential in humans.

Figure 7:
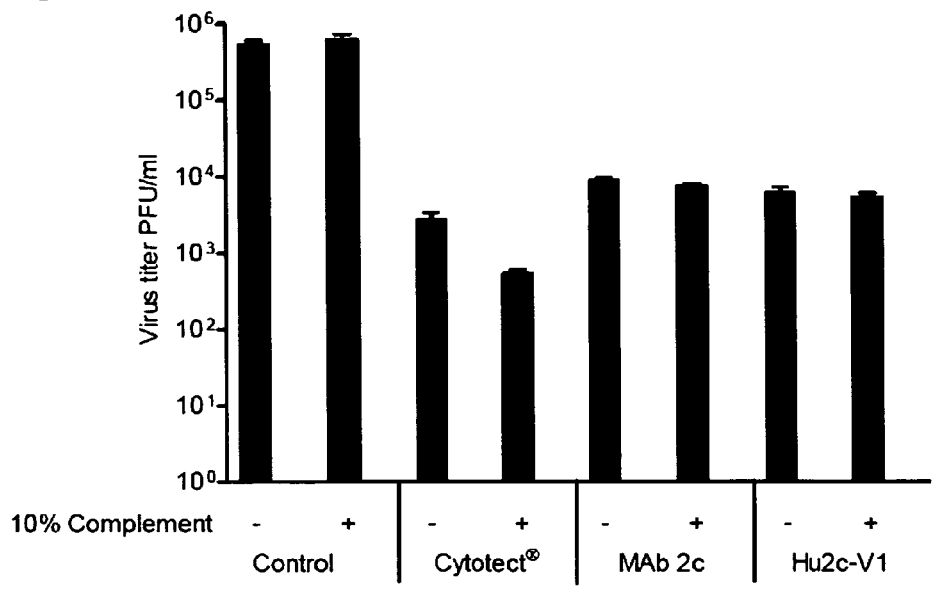
FIG. 7 shows that the HSV neutralization activity of the parental mAb 2c and the humanized mAb hu2c-V1 is complement independent. HSV-1 is pre-incubated with medium (control), polyclonal IgG Cytotect® (120 µg/ml), mAb 2c (2 µg/ml), or mAb hu2c-V1 (2 µg/ml) in the presence or absence of 10% human complement before applying onto Vero cells. Plaque development was scored 2 days later.
Figure 8:
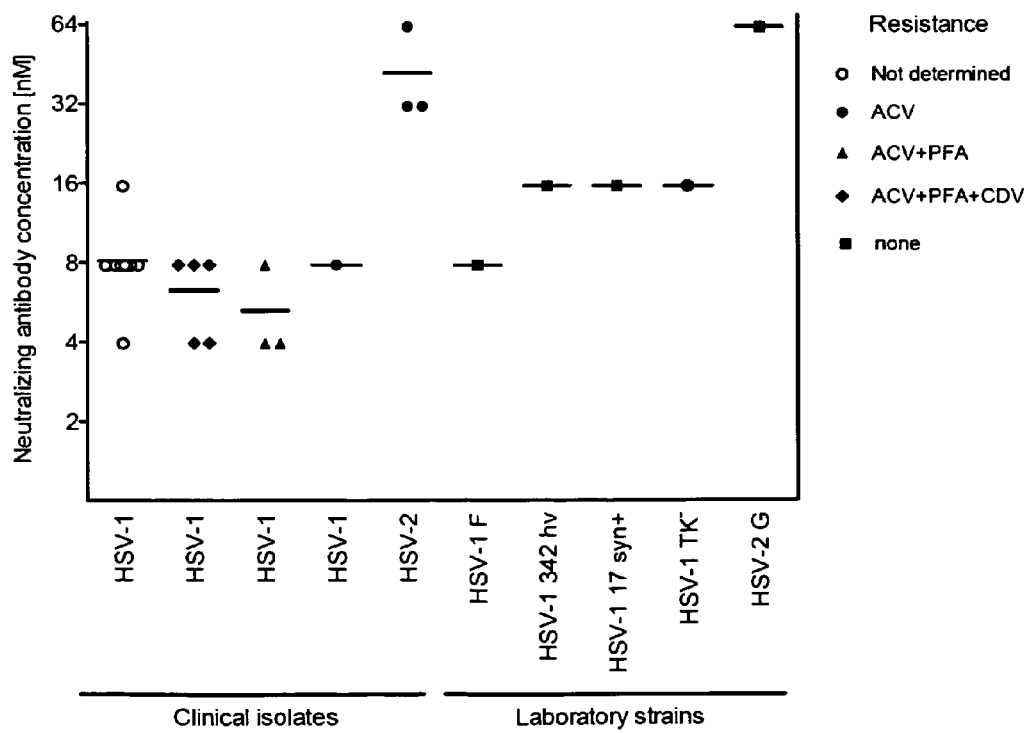
FIG. 8 shows the efficiency of the humanized mAb h2c-V1 to neutralize HSV-1 and HSV-2 derived from patient isolates clinically resistant to acyclovir (ACV), ACV and Foscarnet (PFA), or ACV, PFA and Cidovir (CDV) in comparison to non-resistant laboratory strains (HSV-1 F, HSv-1 324hv, HSV-1 17 syn⁺, HSV-2 G), ACV resistant laboratory strain HSV-1 TK⁻ and clinical isolates where resistance has not been investigated. To determine the titer of mAb h2c-V 1 for complete virus neutralization several antibody concentrations were incubated for 1 h at 37° C. with 100 $TCID_{50}$ of HSV-1 or HSV-2 isolates and incubated for 3 days with Vero cells. MAb hu2c-V1 neutralizes HSV-1 laboratory strains HSV-1 F, HSV-1 324 hv, HSV-1 17 syn⁺, HSV-1 TK⁻ completely at concentrations of 7.8-15.6 nM. HSV-1 clinical isolates are neutralized by mAb h2c-V1 similarly irrespective of their resistance profile. Furthermore, the same neutralization efficiency of mAb hu2c-V1 was shown for strain HSV-2 G and ACV-resistant HSV-2 isolates at concentrations of 31.3-62.5 nM.

The influence of complement on the neutralization activity of the humanized mAb h2c-V1 and the murine mAb 2c was investigated using the plaque-reduction assay. In contrast to human hyperimmune globulin serum (Cytotect®, Biotest AG) the parental mAb 2c and the humanized variant mAb h2c-V 1 neutralize HSV complement-independent (FIG. 7). Complement-independent neutralizing antibodies to HSV-1 gB have been described in the literature to neutralize 50% of the viral input with titers between 0.8-160 µg/ml (Navarro et al, 1992, Virology 186). Titers required to neutralize HSV-1 (F) by 50% using the end-point dilution assay of the murine mAb 2c, the chimeric mAb ch2c and the humanized mAb variants are 3.3-5.1 nM, which corresponds to 0.49-0.78 µg/ml (see Tab. 4). Neutralization assays of clinical isolates of HSV-1 and HSV-2 demonstrate the same susceptibilities to inactivation by the humanized mAb variant h2c-V1 compared to laboratory strains of HSV-1 and HSV-2. Furthermore, mAb h2c-V1 neutralizes HSV from patient isolates clinically resistant to acyclovir (ACV), ACV and Foscarnet (PFA), or ACV, PFA and Cidovir (CDV) with the same efficiency as non-resistant laboratory strains or clinical isolates with unknown resistance (FIG. 8). Hence, the humanized mAb h2c-V1 represents a new potent antiviral agent which overcomes limitations by conventional antiherpetic drugs inducing resistant HSV strains.

Figure 9:
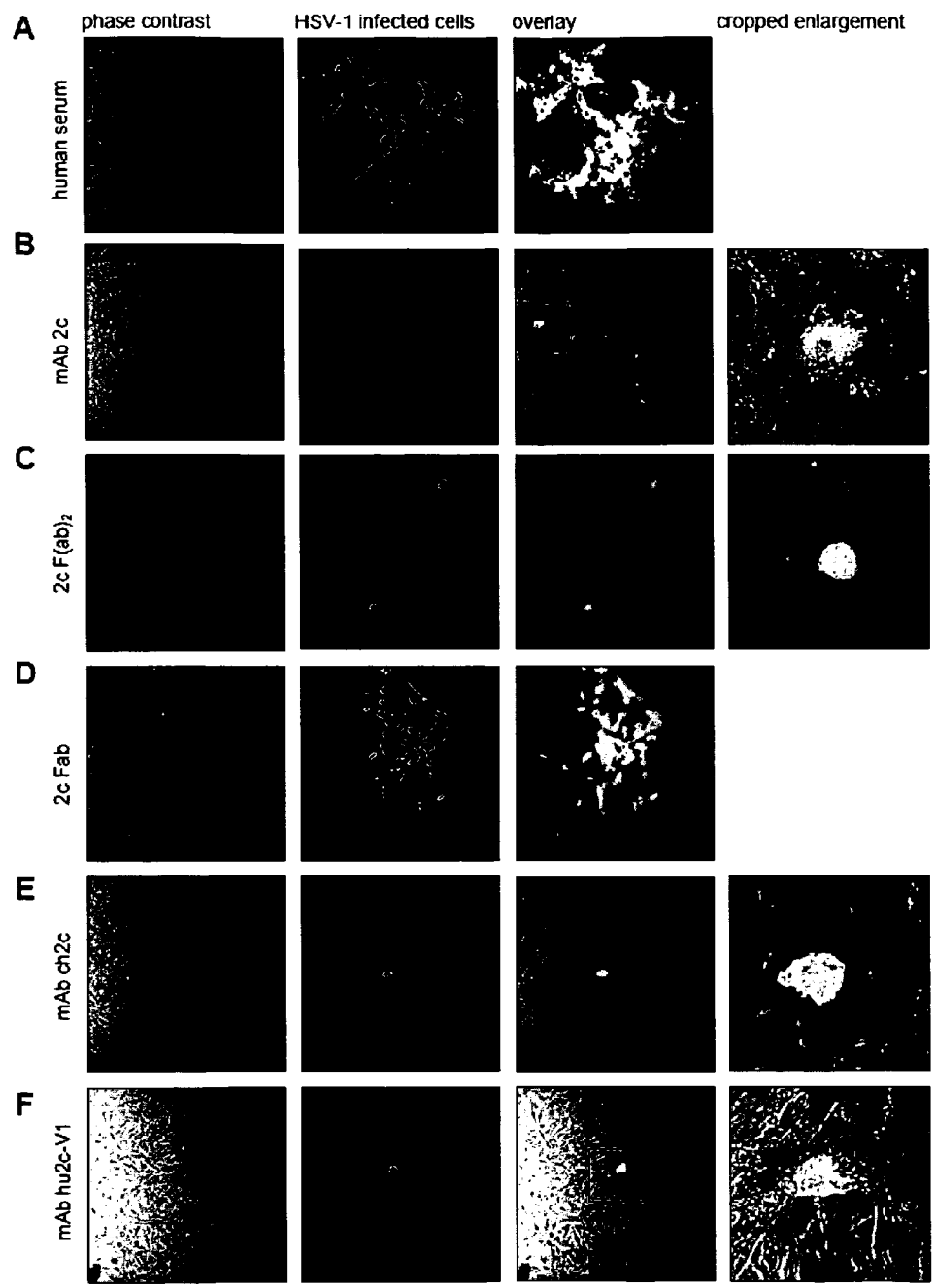
FIG. 9 shows the inhibition of the viral cell-to-cell spread by the anti-HSV antibody of the invention. Vero cells infected with HSV-1 F for 4 h were washed twice and incubated with medium containing an excess of either human polyclonal anti-HSV control serum (1:20), the murine mAb 2c (500 nM), 2c-derived antibody fragments F(ab')$_2$ (500 nM) or Fab (3000 nM) prepared by enzymatic digestion, the chimeric mAb ch2c (500 nM), or with the humanized mAb variant 1, hu2c-V1 (500 nM), respectively. Two days after infection spreading of the virus was detected with fluorescence labeled polyclonal goat-anti-HSV serum using a Leica DM IRE2 confocal microscope at 40-fold magnification. Neutralization titre of the human polyclonal anti-HSV was previously determined 1:160 using 100 $TCID_{50}$ in a volume of 100 µl. The anti-HSV serum at a dilution of 1:20 cannot prevent the spreading of virus to adjacent cells. Cell-to-cell spread could be successfully inhibited by 500 nM of either the murine mAb 2c, the 2c-F(ab')$_2$-antibody fragment, the chimeric and the humanized mAb. The monovalent 2c-Fab-fragment at the highest tested concentration of 3.000 nM was not able to completely inhibit the cell-to-cell spread.

For spreading within a host HSV uses two mechanisms: release of cell-free particles and direct, cell-to-cell spread. Cell-cell spread of HSV may confer advantages over cell-free spread, such as more rapid viral replication and dissemination, and resistance to elements of the humoral immune response. In order to examine the cell-to-cell spread by the anti-HSV antibodies, Vero cells were seeded on glass coverslips in a twenty-four-well tissue culture plate, grown to confluency, and inoculated with HSV-1 F at 400 $TCID_{50}$ per well for 4 h at 37° C. Virus inoculum was aspirated, Vero cells washed twice with PBS and further cultured for 48 h at 37° C. in 1 ml DMEM containing 2% FBS, antibiotics, and either an excess of neutralizing antibodies, human polyclonal anti-HSV-serum or no neutralizing antibodies for control purposes. After 48 h culture medium was removed, Vero cell monolayers washed twice with HEPES buffered saline, and fixed in 4% paraformaldehyde in PBS for 15 min at room temperature. Cell monolayers were rinsed twice with PBS and incubated for 15 min in 500 µl blocking buffer containing 0.05% Tween 20 in HEPES buffered saline. Viral antigens were detected by staining of HSV-1 infected cell monolayers with FITC-conjugated polyclonal goat-anti-HSV serum (BETHYL, Montgomery, Tex, USA) diluted 1:100 in blocking buffer. Cell monolayers were washed three times with PBS and mounted with Mowiol (Calbiochem, San Diego, Calif., USA). Immunofluorescence-positive cells were acquired with a Leica DM IRE2 confocal microscope at a 40-fold magnification (FIG. 9).

Human polyclonal anti-HSV-serum (1:20) has no inhibitory effect on the HSV cell-to-cell spread (FIG. 9A). The parenteral mAb 2c and its $F(ab)_2$-fragment inhibit at a concentration of 500 nM the cell-to-cell spread completely and only single HSV-infected cells are detectable (FIGS. 9B&C). The Fab-fragment, which was applied in a six-fold higher concentration of the parenteral mAb 2c reduces in comparison to the human polyclonal anti-HSV serum the cell-to-cell spread slightly, but is not able to inhibit the cell-to-cell spread completely (FIG. 9D). As already shown in the neutralization assay, these results confirm that the bivalence of neutralizing antibodies plays a key role for their ability to inhibit HSV-spreading. The chimeric mAb ch2c and the humanized variant mAb h2c-V1 inhibit the HSV cell-to-cell spread at a concentration of 500 nM as efficient as the parenteral mAb 2c (FIGS. 9E&F).A conventional plaque inhibition assay (Highlander et al., 1988) which was additionally carried out confirmed the results obtained by evaluation with the confocal microscope.

Figure 10:
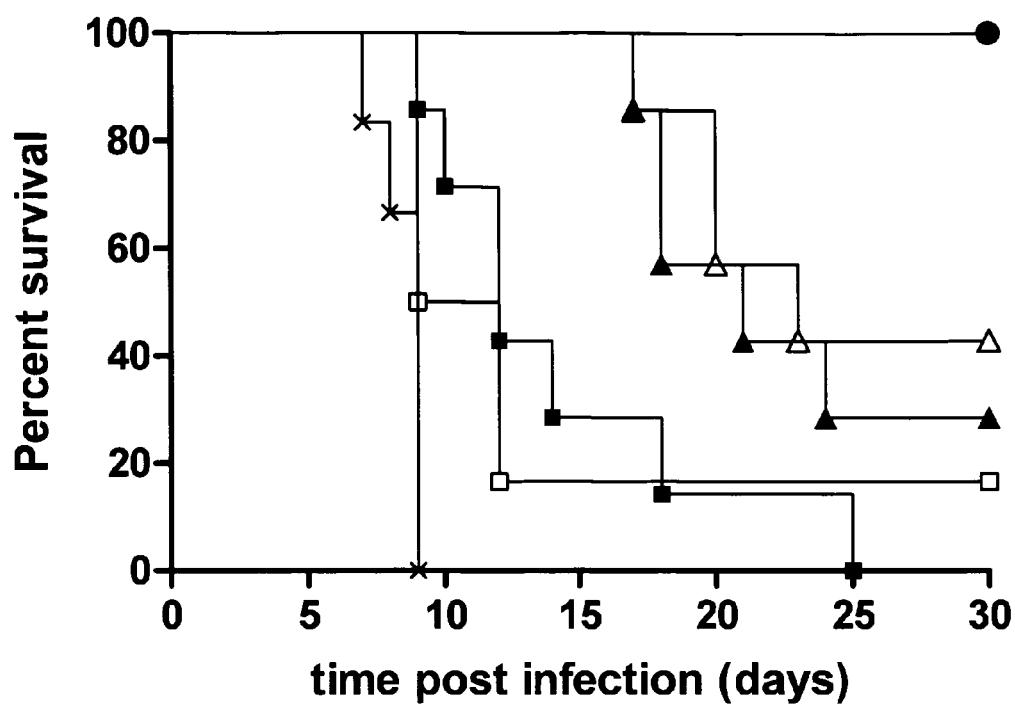
FIG. 10 shows the survival of NOD/SCID mice intravaginally infected with HSV-1 after passive immunization with anti-HSV mAbs. Mice received 24 h prior to infection intravenously PBS (cross), 2.5 mg/kg (squares), 5 mg/kg (triangles), or 15 mg/kg (circles) of either the parental mAb 2c (open symbols) or the humanized mAb hu2c-V1 (closed symbols). Mice were infected intravaginally with 1×10⁶ TCID50/20 µl of the neurovirulent HSV-1 strain F. Infected mice with symptoms of weight loss, vulvitis/vaginitis or neurological diseases were killed, and their organs examined for infectious virus by titration on Vero cell monolayers as described previously. Non-infected mice were killed at day 30. Animals per group n=7.
Figure 11:
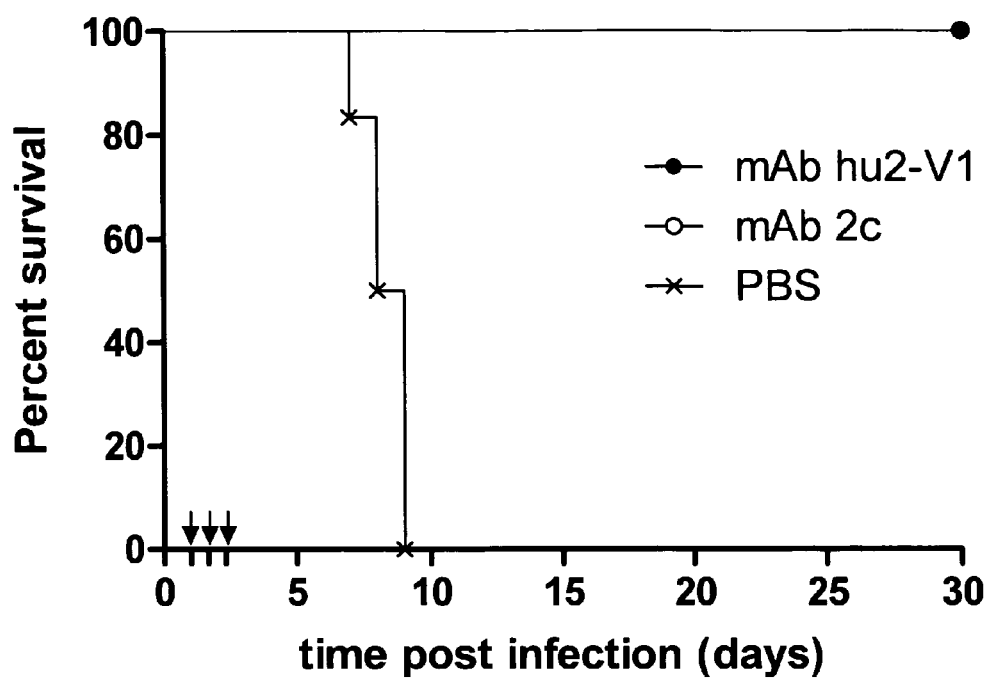
FIG. 11 shows the protection of NOD/SCID mice by systemically applied antibodies against HSV-1 dissemination. Starting 24 h post-infection mice received either 15 mg/kg mAb 2c or humanized mAb hu2c-V1 three times intravenously at time points indicated by arrows (24 h, 40 h, 56 h). Infected animals per group n=7.
Figure 12:
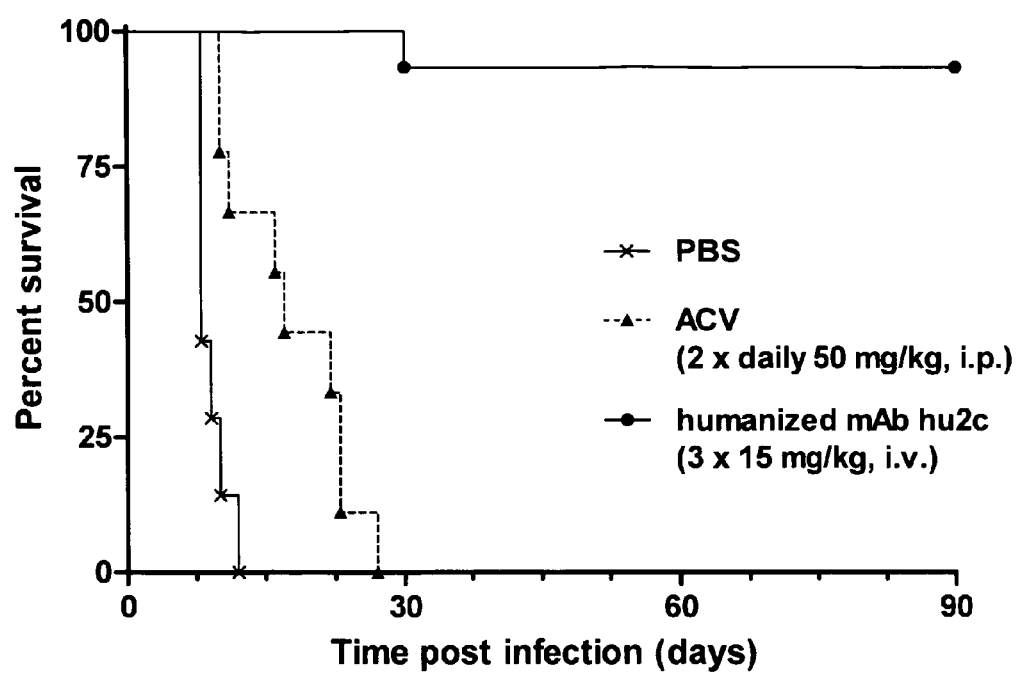
FIG. 12 shows that NOD/SCID mice infected intravaginally with a patient derived HSV-1 isolate resistant towards Acyclovir, Foscarnet and Cidovovir were significantly protected against lethal encephalitis upon treatment intravenously at 24 h, 40 h, and 56 h post infection with 15 mg/kg humanized mAb hu2c-V1. Mice receiving twice daily standard treatment with Acyclovir all died within 28 days.

Initial in vivo HSV protection experiments show that a single i.v. dose of 5 mg/kg of the humanized mAb h2c-V1 similarly to the parental mAb 2c prolongs the survival of intravaginally HSV-1 F infected severely immunocompromized mice (NOD-SCID) significantly (FIG. 10). Mice receiving 15 mg/kg of either the humanized mAb h2c-V1 or the parental mAb 2c are fully protected against lethal encephalitis (FIG. 10). Furthermore, the humanized mAb 2c-V1 also confers protection from viral dissemination and lethal encephalitis in the presence of an established peripheral HSV infection. NOD/SCID mice with a high HSV-1 titer in vaginal irrigations at 24 h after viral challenge were completely protected from the lethal outcome of infection when repeatedly treated at 24 h, 40 h and 56 h intravenously with 15 mg/kg of humanized mAb 2c-V1 or mAb 2c (FIG. 11). Moreover, the humanized antibody mAb 2c-V1 also prevented leathel encephalitis in NOD/SCID with established infection of a multi-resistant HSV strain. In contrast, mice receiving Acyclovir all died (FIG. 12).

Epitope Mapping

Figure 13B:
FIG. 13 shows the epitope localization of mAb 2c to gB. (A) shows an amino acid sequence alignment of glycoprotein B (gB) of HSV 1 and HSV2. Shown is an alignment of the gB protein amino acid sequence of the following strains (corresponding NCBI accession number in brackets): HSV1 strains KOS(P06437), F (P06436), gC-39-R6 (ABM66850), and HSV2 strains 333 (ABU45423), HG52 (P08666), and MMA (AAB60547). The signal sequence of gB is underlined. The mature gB starts at position 31 with the amino acids AP. Numeration of amino acids is shown for gB including the signal peptide sequence. Epitope numerations are accordingly. MAb 2c binds to two separate regions within gB (boxed sequence regions) as shown by peptide microarrays. Amino acids $_{299}$PFYGYRE$_{305}$ has been shown to be essential for binding of mAb 2c. (B) Characterization of mAb 2c according to its reactivity with recombinant gB under different Westernblot conditions. Recombinant gB (730t) was resolved on a 8% SDS-PAGE under native (N) or denaturating (D) conditions, transferred to a nitrocellulose membrane and incubated for 1 h in TNT-blocking buffer containing 2% milk. The membranes were probed with gB specific monoclonal antibodies mAb H1817, mAb H126, or mAb 2c and binding to gB was detected by HRP-conjugated polyclonal goat-anti-mouse serum and chemiluminescence. For controls mAbs H1817 and H126, recognizing a continuous (Bender et al., 2007) and a discontinuous epitope (Kousoulas et al., 1988), respectively, were used. A typical staining pattern for a linear epitope was obtained in Western blot analysis with mAbH1817 showing detection of monomeric and trimeric forms of gB under non-reducing conditions and sole predominant staining of gB monomer under reducing conditions. As expected, mAbH126 reacted with gB only under native conditions. Recognition of solely the upper gB protein band >170 kDa indicates that mAb H126 binds specifically the trimeric gB. MAb2c reacted with native and denatured gB, however, reactivity under denaturing conditions was much weaker compared with mAb H1817 and indicates that mAb 2c binds to a discontinuous epitope that seems to be either resistant to denaturation or refold during SDS-PAGE electrophoresis and is therefore termed "pseudocontinuous" epitope (Bender et al., 2007). Molecular mass (kDa) is indicated on the left and migration of gB trimer and monomer on the right.
Figure 22:
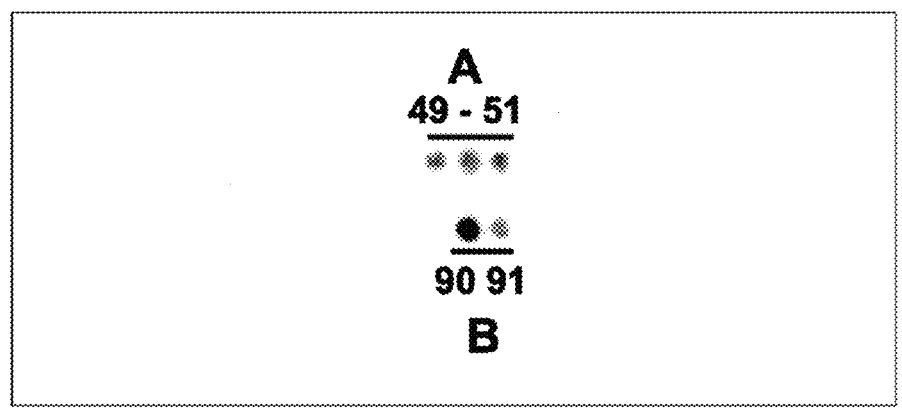
FIG. 22 shows the peptide scanning on the HSV-1 gB sequence from amino acid 31 to 505. Cellulose membrane-bound 15-mer peptides with an overlap of 12 amino acids (15/12 scan) resulting in a total of 155 different peptide spots were incubated with MAb 2c. Peptide-bound MAb 2c was detected using a peroxidase-labeled anti-mouse IgG Fab fragment and a luminol-like chemiluminescence substrate. MAb 2c was found to bind to a triplet (peptides 49-51) and a doublet (peptides 90-91) of consecutive gB peptides designated binding sites A and B. The gB sequence common to the peptides from each site is highlighted in bold letters (below) and represents the gB sequence from residues 181 to 189 and residues 301 to 312.

Binding studies using COS-1 cells transfected with expression plasmids coding for either full-length gB (31-904) or gB mutants with C-terminal truncations at positions 720, 630, 503, 487, and 470 located the epitope recognized by the parental murine mAb 2c within the first 487 amino acids of gB. Further investigations using solid phase bound synthetic 15 amino acid (aa) long peptides with 12 aa overlaps between sequential peptides showed, that mAb 2c maps to a conformational epitope. MAb 2c binds to three consecutive peptides representing the glycoprotein B sequence from aa 175 to 195 (region A). In addition, mAb 2c binds strongly to a peptide representing amino acids 298-312 ($_{298}$SPFYGYREGSH-TEHT$_{312}$) (SEQ ID NO: 17) and binds moderately to the subsequent peptide representing amino acids 301-315. (FIG. 13A & FIG. 22). Characterization of mAb 2c according to its reactivity on Western blots with recombinant gB (gB(730)t, kindly provided by Florent Bender, University of Pennsylvania, Philadelphia, USA), which was separated under native or denaturating SDS-PAGE conditions, confirms that mAb 2c recognizes a discontinuous epitope that is either partially resistant to denaturation or that reformed during Western blot conditions, and is therefore termed "pseudocontinuous" epitope (Ref Bender, F et al. J. Virol. 2007, 81 p 3872-3841) (FIG. 13B)

In order to identify epitopes in HSV-1 gB protein relevant for the virus-neutralizing activity of mAb2c, monoclonal antibody resistant (mar) HSV-1 mutants with single amino acid (aa) exchanges in their glycoprotein have been studied (Table 5).

TABLE 5

Neutralization and binding activity of mAb 2c towards monoclonal antibody resistant (mar) HSV-1 mutants

| Mar mutant | amino acid exchange within gB protein of mar mutant[a] | neutralization % | binding |
|---|---|---|---|
| R126[1;2] | Y->N$_{303}$ | 0 | − |
| R1375[3] | R->Q$_{304}$ | 0 | − |
| B4.1[4] | E->K$_{305}$ | 0 | − |
| R1435[3] | H->Y$_{308}$ | 100 | +++ |
| R233[1] | R->H$_{328}$ | 100 | +++ |

[a]numbering according to the mature glycoprotein B including signal sequence (FIG. 13A)
[1]Kousoulas et al., 1984
[2]Pellett et la., 1985
[3]Kousoulas et al., 1988
[4]Highlander et al., 1989

Mab 2c did not neutralize mar mutants R126, R1375, and B4.1, but completely neutralized the infectivity of mutants R1435 and R233, respectively. Furthermore, immunofluorescence assays confirmed that mAb 2c does not bind to Vero cells infected with mar mutants R126, R1375, and B4.1. These results indicate that amino acids Y$_{303}$, R$_{304}$ and E$_{305}$ are essential for the neutralization activity of mAb2c. A strong fluorescence signal was obtained using Vero cells infected with mar mutants R$_{1435}$ and R$_{233}$.

In particular, the recognition and binding of mAb 2c to amino acids 303-305 of gB was found to be essential for its function (viral neutralization, inhibition of cell-to-cell spread). As this region of gB is highly conserved among HSV-1 and HSV-2 strains, it is assumed that these amino acids belong tho the core fusion machinery of gB and are essential for virus entry. Therefore, occurrence of natural gB-mutants, to which mAb 2c does not bind, is even under high selection pressure unlikely.

Example 3

Determination of Antibody Affinity

Monolayers of Vero cells were infected at 80-90% confluence with HSV-1 or HSV-2 at MOI 3 and harvested the next day by trypsinization followed by washing in PBS. Cell surface binding measurements of 2c antibodies were carried out as described previously (1). Briefly, purified mAb 2c or derived antibody fragments 2c-F(ab')$_2$, 2c-Fab, and 2c-scFv were incubated in triplicate at concentrations from 0.03 nM-500 nM with 5×10$^5$ Vero cells in 100 µl FACS buffer (PBS, 2% FBS, 0.1% sodium azide) for 1 h at room temperature. Cells were washed twice with 200 µl FACS buffer and incubated with FITC-labeled Fab-specific goat-anti-mouse IgG, (15 µg/ml, Jackson ImmunoResearch, Newmarket, Suffolk, England) for detection of bound mAb 2c, 2c-F(ab')$_2$, and 2c-Fab. Bound scFv was detected by first incubating with saturating concentrations of the anti-c-myc mAb 9E10 (10 µg/ml; Roche, Indianapolis, Ind., USA), followed by two washes and incubation with Fcγ-specific FITC-labeled goat-anti-mouse IgG (15 µg/ml; Jackson ImmunoResearch). Cells were washed twice and resuspended in FACS buffer. Fluorescence was measured on a FACScalibur (BD Bioscience, San Jose, Calif., USA), and median fluorescence intensity (MFI) was calculated using the CellQuest™ software (BD Biosciences). Background fluorescence was subtracted and equilibrium binding constants were determined by using the Marquardt and Levenberg method for nonlinear regression with the GraphPad Prism version 4.0 (GraphPad Software, La Jolla, Calif.).

Epitope Characterization.

Immunoreactivity of mAb 2c with native or denatured truncated glycoprotein B, gB(730)t (4), kindly provided by Roselyn J. Eisenberg and Gary H. Cohen (University of Pennsylvania, Philadelphia, USA) was performed essentially as described (4): Purified gB(730)t (0.75 µg) was resolved on 8% SDS-PAGE under either non-reducing (sample buffer containing 0.2% SDS) or denaturating (sample buffer containing 2% SDS and 155 mM β-Mercaptoethanol, 2 min at 95° C.) conditions and transferred onto nitrocellulose membrane. Membrane strips were blocked with 2% milk in TNT buffer (0.1 M Tris.HCl, pH 7.5, 0.15 M NaCl, 0.05% Tween-20) for 1 hour followed by incubation with 5 µg/ml of glycoprotein B specific antibodies mAb 2c, H126 (Novus Biologicals, Littleton, Colo., USA) and H1817 (Novus) in 2% milk/TNT-buffer for 2 hours at room temperature. Bound antibodies were detected with horseradish peroxidase conjugated polyclonal goat-anti-mouse antibody (1:20,000 QED Bioscience Inc. San Diego, Calif., USA) and chemiluminescence (Thermo Scientific,) using the LAS 3000 Luminescent Image Analyzer (Fujifilm, Tokyo, Japan).

COS-1 cells were transiently transfected by the DEAE-dextran method with plasmids coding either for the full length HSV-1 gB (31-904, pRB9221) or C-terminal deletion mutants truncated at positions 720 (pTS690), 630 (pPS600), 503 (pRB9510), 487 (pRB9509), and 470 (pRB9508). The plasmids were kindly provided by L. Pereira (52, 55) Immunofluorescence assays with transfected cells using mAb2c or control antibodies were carried out as described elsewhere (53).

Peptide Mapping.

Cellulose-bound overlapping 13meric peptides and duotopes were automatically prepared according to standard SPOT-Synthesis protocols as described (20, 34) (JPT Peptide Technologies, Berlin, Germany). In addition, peptides coupled with a reactivity tag and a linker were immobilized chemoselectively on a modified glass surface in three identical subarrays and purified by removal of truncated and acetylated sequences by subsequent washing steps. Peptide microarrays were blocked with TBS containing blocking buffer (Pierce International) for 2 h, and incubated with 10 µg/ml mAb 2c in blocking buffer for 2 h. Peptide microarrays were washed with TBS-buffer containing 0.1% Tween (T-TBS) and peptide-bound antibody on the peptide membrane was transferred onto a PVDF membrane. Anti-mouse IgG either peroxidase-labelled (Sigma) or fluorescently-labelled (Pierce) was used as secondary antibody at a final concentration of 1 µg/ml in blocking buffer. After 2 h incubation and final washing with T-TBS PVDF membranes were analyzed using chemiluminescence substrate (Roche Diagnostics). Glass slide peptide microarrays were washed thoroughly with T-TBS and 3 mM SSC-buffer (JPT Peptide Technologies), dried under nitrogen and scanned using a high resolution fluorescence scanner (Axon GenePix 4200 AL). Fluorescence signal intensities (Light Units, LU) were analyzed using spot-recognition software (GenePix 6.0) and corrected for background intensities from control incubations with secondary anti-mouse IgG.

Virus Neutralization Assay.

Neutralizing activity of antibodies was determined by endpoint dilution assay as described previously (16). Briefly, serial dilutions of antibodies were incubated with 100 $TCID_{50}$ of HSV-1 or HSV-2 for 1 h at 37° C. in cell culture medium. The antibody virus inoculum was applied to Vero cell monolayers grown in microtiter plates and cytopathic effect (CPE) was scored after 72 h incubation at 37° C. The antibody concentration required for reducing virus-induced CPE by 100% was determined as complete neutralization titer. In addition, virus neutralization capacity of monovalent 2c-Fab fragments was investigated in the presence of cross-linking antibodies, by adding an excess of anti-murine Fab IgGs (2600 nM, Jackson ImmunoResearch, Newmarket, Suffolk, England) to the pre-incubation step. For control purposes virus without antibody and antibody alone was used to induce maximal CPE or no CPE, respectively. Virus neutralization assays were repeated at least twice with similar results.

Post-Attachment Neutralization Assay.

Prechilled Vero cell monolayers (4° C. for 15 min) were infected with 100 $TCID_{50}$ HSV-1 F at 4° C. for 1 h to allow virus absorbtion before serial dilutions of either mAb 2c or a polyvalent IgG preparation from human plasma (Intratect®, Biotest AG, Dreieich, Germany, were added (post-attachment neutralization). To compare pre-attachment versus post-attachment neutralization efficacy of mAb 2c under identical experimental conditions, 100 $TCID_{50}$ HSV-1 F were incubated for 1 h at 4° C. with the same antibody dilutions before adding to prechilled Vero cell monolayers. Inoculated Vero cells from both assays were incubated for another 1 h at 4° C. before transferred to 37° C. Neutralization titers were determined after 72 h as described in the standard neutralization assay above.

Cell-to-Cell Spread Assay.

Vero cells grown on glass coverslips to confluency were inoculated with HSV-1 F at 400 $TCID_{50}$ per well in 500 µl for 4 h at 37° C. Virus inoculum was aspirated, Vero cells washed twice with PBS and further cultured for 48 h at 37° C. in the presence or absence of an excess of neutralizing antibodies in 1 ml growth medium with 2% FBS. Pooled human sera derived from immunized donors with high titers of anti-HSV-1 immunoglobulins were used as control at an dilution of 1:20, concentrations of bivalent antibodies mAb 2c and 2c-F(ab')$_2$ were 500 nM and of the monovalent 2c-Fab 3000 nM. After 48 h culture medium was removed, Vero cell monolayers washed twice with HEPES buffered saline, and fixed with 4% paraformaldehyde in PBS for 15 min at room temperature. To visualize the viral spread cells were rinsed twice with PBS, incubated for 15 min in 500 µl HEPES buffered saline with 0.05 Tween 20 and stained with FITC-conjugated polyclonal goat-anti-HSV serum (1:100, BETHYL, Montgomery, Tex., USA). Stained cells washed three times with PBS were mounted in mounting medium containing 0.2 g/ml Mowiol 4-88 (Calbiochem, San Diego, Calif., USA). Immunofluorescence images were acquired with a Leica DM IRE2 confocal microscope at a 40-fold magnification. Cell-to-cell spread inhibition was tested in addition by postadsorption virus neutralization assay. Vero cells grown to confluency in six-well plates were incubated for 4 h at 37° C. with 200 $TCID_{50}$ of HSV-1 F in 3 ml DMEM containing 2% FBS, and antibiotics. Cell monolayers were washed twice with PBS and overlaid with warm plaquing medium (DMEM, 5% (w/v) agarose, 10% FBS, antibiotics) containing an excess of neutralizing antibodies or polyclonal human HSV-1 neutralizing sera. Plaque formation was analyzed by light microscopy after 48 h incubation at 37° C.

DNA-Quantification.

HSV-1 and HSV-2 genomes were quantified performing real-time (RT) PCR. DNA was purified from samples containing equivalent amount of infectious particles of HSV-1 and HSV-2 using the automated nucleic acid extraction system MagNA Pure LC System (Roche) according to manufacturer instructions. Viral DNA was then quantified performing RT-PCR (Lightcycler, Roche) using the RealArt HSV-1/HSV-2 quantification kit (Qiagen).

Mouse Protection Experiments.

Anesthetized female nonobese diabetic/severe combined immunodeficient (NOD-SCID) mice (NOD.CB17-Prkdc$^{scid}$/J, Charles River Laboratories, Research Models and Services, Sulzfeld, Germany), 6-8 weeks of age, were challenged intravaginally with 20 µl inoculum of 1×10$^6$ $TCID_{50}$ HSV-1 F per mouse. Skin glue (Epiglu, Meyer-Haake Medical Innovations, Wehrheim, Germany) was applied onto the vulva to prevent dircharge of the virus inoculum. The delivered inoculum induced infection rates >94% as assessed by culture of vaginal lavage. Mice were examined daily after viral inoculation for loss of weight, vulvitis/vaginitis (redness, mucopurulent discharge and signs of inflammation) and neurological disease. Mice displaying any of theses symptoms were sacrificed immediately. Mice were passively immunized by intravenous (i.v.) injection of purified mAb 2c either 24 h prior to viral inoculation for immune prophylaxis or 24 h, 40 h, and 56 h after viral infection for therapeutic treatment. Mice were assessed for infection by determination of virus titers from vaginal irrigations obtained on days 1, 2, 4, 6 and 8 after infection and at the time of death using the endpoint dilution assay on Vero cells. Viral loads in organs (spleen, adrenal gland, lung heart, liver, kidney, spinal cord, and brain) of sacrificed mice were determined after homogenization of organs by titration on Vero cell monolayers as described elsewhere (41). Each test and control group contained 9-10 animals with detectable HSV-1 infection.

Results

Mapping and Analysis of the gB Epitope Recognized by mAb 2c.

The recently determined crystal structure of the ectodomain of gB from HSV type 1 (HSV-1) revealed a multi-domain trimer with five distinct structural domains: domain I (base), domain II (middle), domain III (core), domain IV (crown), and domain V (arm) (24). To characterize the neutralizing epitope of mAb 2c, we tested its reactivity with recombinant gB(730t)(4) in Western blot analysis either under reducing or non-reducing conditions. As controls we used mAb H1817, recognizing a linear epitope (4) and mAb H126 recognizing a discontinuous epitope (33). A typical staining pattern for a linear epitope was obtained in Western blot analysis with mAb H1817 showing detection of monomeric and trimeric forms of gB under non-reducing conditions and sole predominant staining of gB monomer under reducing conditions (FIG. 13B). As expected, mAb H126 reacted with gB only under native conditions. Surprisingly, recognition of solely the upper gB protein band >170 kDa suggests that mAb H126 is trimer specific (FIG. 13B). MAb 2c reacted with native and denatured gB, however, reactivity under denaturing conditions was much weaker compared with mAb H1817 (FIG. 13B). Weak reactivity with gB monomers under denaturing conditions has been previously reported for a set of other neutralizing antibodies binding to discontinuous epitopes that seem to be either resistant to denaturation or refold during SDS-PAGE electrophoresis and therefore termed "pseudocontinuous" epitopes (4).

Figure 14A:
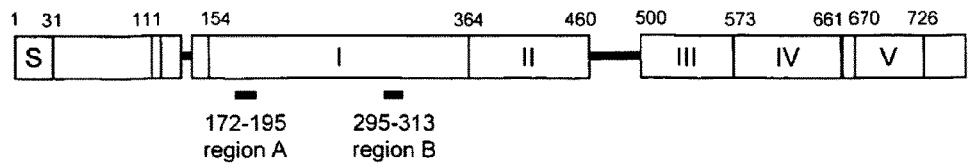
FIG. 14 shows the peptidemapping of mAb 2c to gB. (A) Schematic localization of binding regions A and B identified on a peptide-library spanning the extracellular domain of gB from amino acids 31 to 505. The 13meric peptides were synthesized on a continuous cellulose membrane with an offset of 3 amino acids and bound mAb 2c was detected with a peroxidase-conjugated secondary antibody by chemiluminescence. Functional domains I-V corresponds to the crystal structure of gB by Heldwein et al. and regions not solved in the crystal structure are shown in grey (24), S, signal sequence. (B) Fluorescence signal intensities from high resolution laser scans with 13meric peptides immobilized on glass slides via a flexible linker.
Figure 14B:
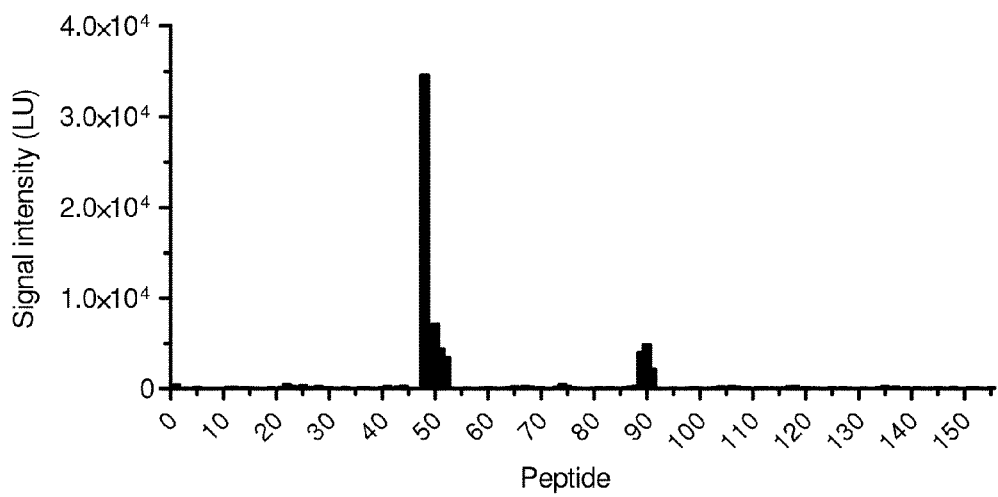

To identify the specific epitope involved in binding of mAb 2c we used gB derived peptides displayed on peptide microarrays. First, the gB sequence displaying amino acids 31 to 505 was prepared by Spot-Synthesis as overlapping 13meric peptides bound with uncharged acetylated amino terminal ends to a continuous cellulose membrane with an offset of 3 amino acids. To avoid shifting of the binding equilibrium for the non-complexed antibody, mAb 2c peptide scans were immobilized on a PVDF membrane prior to detection by chemiluminescence. As shown in the schematic representation of the full length gB with indicated functional domains (FIG. 14A), mAb 2c reactivity was restricted to peptides spanning two separate regions within domain I, three consecutive peptides comprising residues 175 to 193 (binding region A) and two overlapping peptides comprising residues 295 to 310 (binding region B). To validate both identified binding regions, we used an additional set of purified 13meric peptides immobilized on glass slides via a flexible linker. Compared to the cellulose screen the read-out of this microarray scanning via fluorescence confirmed the same epitope binding regions (FIG. 14B). Due to the application of purified peptides and a high resolution microarray scanning system additional consecutive peptides at both binding sites were recognized by mAb2c in this peptide microarray (FIG. 14B).

Figure 15:
FIG. 15 shows the localization of neutralizing mAb 2c epitopes on the gB crystal structure (PDB-ID 2GUM). The ribbon diagram of the gB trimer is shown. Asterisks indicate the fusion loops of two protomers, fusion loops of the third protomer are not visible. The mapped residues of the discontinuous mAb 2c epitope, $F_{175}$ to $A_{190}$ and $F_{300}$ to $E_{305}$, are indicated in surface representation by dark grey for one protomer and by light grey for both other protomers.

We mapped the identified binding sites for mAb 2c to the solved gB structure (24). Interestingly, the peptide $_{172}$QVWFGHRYSQFMG$_{184}$ (SEQ ID NO: 18) showing the strongest reactivity with mAb 2c overlapped with one of the two putative fusion loops (fusion loop 1 $_{173}$VWFGHRY$_{179}$) (SEQ ID NO: 19) located in a curving subdomain of domain I (22) (FIG. 15). However, localization of binding site A at the base of the gB trimer makes it inaccessible to mAb 2c in the available gB structure most likely representing the postfusion conformation (24). Residues of binding site B are exposed and located at the upper part of the domain I (FIG. 15).

Figure 16:
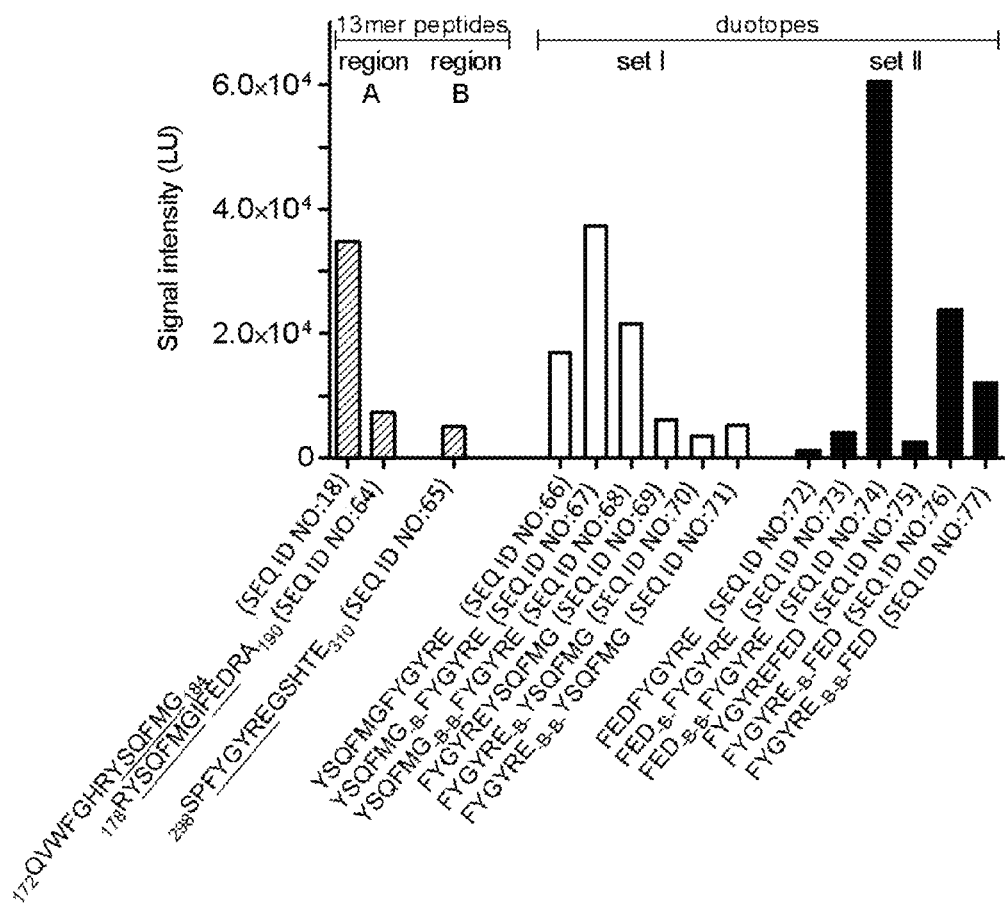
FIG. 16 shows the duotopescanning of mAb 2c. Consensus sequences (underlined) of mAb 2c binding regions A and B (dashed bars) were synthesized as duotopes (white and black bars) joined either directly or separated by one or two β-alanine spacers (B, B-B). Reactivity of mAb 2c with duotopes was recorded by fluorescence signal intensities from high resolution laser scans.

To further assess the conformation dependent epitope of mAb 2c, consensus sequences of both binding regions were connected in various combinations as duotopes either directly or separated by one or two β-alanine spacers (FIG. 16). It has recently been shown that linker insertions in close proximity to fusion loop 1 after residue E$_{187}$ result in fusion-deficient gB mutants (40,61), even though gB folds into a postfusion conformation (61). Therefore, we included in addition to the consensus motif $_{179}$YSQFMG$_{184}$ (SEQ ID NO: 20) of binding region A the $_{186}$FED$_{188}$ motif of binding region A into separate duotope scans. Compared to the peptide $_{172}$QVWFGHRYSQFMG$_{184}$ (SEQ ID NO: 18) displaying the strongest binding reactivity with mAb 2c in the 13meric peptide scans (FIG. 16), the combination of both binding site A motifs with the consensus peptide $_{300}$FYGYRE$_{305}$ (SEQ ID NO: 21) of binding site B resulted in two duotopes with enhanced signal intensities (FIG. 16, duotope sets I & II). Whereas binding strength of mAb 2c to duotope $_{179}$YSQFMG$_{184}$-βA-$_{300}$FYGYRE$_{305}$ (SEQ ID NO: 22) was only slightly increased, an almost saturation of the fluorescence signal intensity was obtained with duotope $_{186}$FED$_{188}$-βA-βA-$_{300}$FYGYRE$_{305}$ (SEQ ID NO: 23).

Thus, the results from the peptide microarrays correspond to the Western blotting results and demonstrate that mAb 2c recognizes a conformation dependent epitope. To prevent fusion of the virion envelope with the cell membrane mAb 2c should bind to the prefusion conformation of gB. However, the neutralizing epitope of mAb 2c maps only in part to the surface of the gB conformation present in the available gB crystal structure (24) and indicates that gB might adopt distinct conformations during entry.

Characterization of mAb 2c Derived Bivalent and Monovalent Antibodies.

Figure 17:
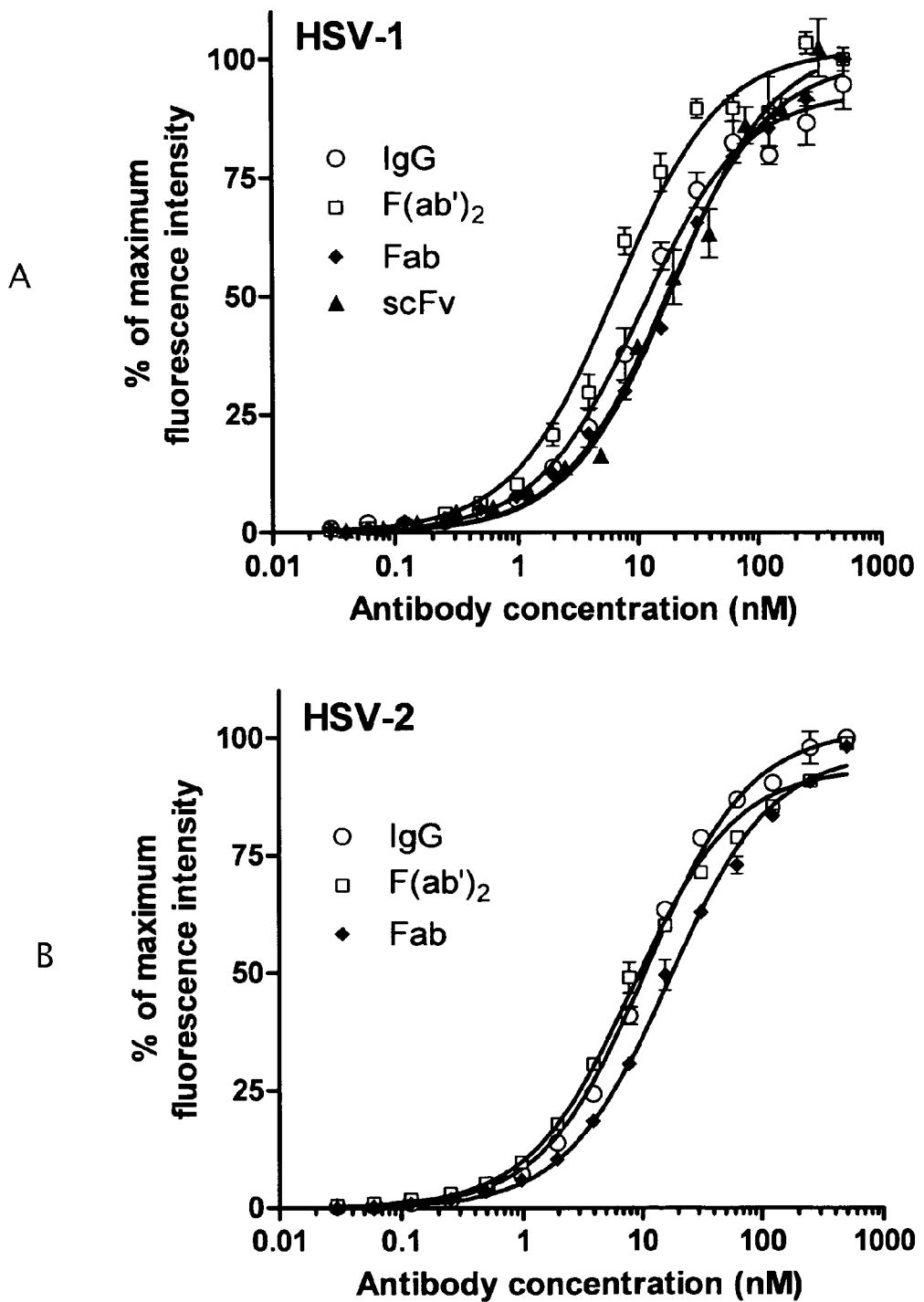
FIG. 17 shows the equilibrium-binding curves for mAb 2c, 2c-F(ab')2, 2c-Fab, and 2c-scFv as determined by flow cytometry. Binding activities to (A) HSV-1 F or (B) HSV-2 G infected Vero cells at indicated concentrations are shown as percent of maximum median fluorescence intensity. Experiments were twice performed in triplicate; bars represent standard deviations.

Monoclonal antibodies have been used by several investigators to identify regions on gB essential for its function in virus entry (4, 25, 39, 52). It has been suggested that neutralizing antibodies, which have been mapped to a unique functional region at the base of the gB trimer comprising residues of the C-terminal end of domain V and residues of domain I of a proximate protomer, interfere with the fusogenic activity of gB (4). We therefore hypothesized that monovalent antibody binding to the mAb 2c epitope within domain I close to the C terminus of domain V should sufficiently block cooperative conformational changes upon activation of gB. Since mAb 2c neutralizes HSV-1 without complement in vitro (16), we generated conventional F(ab')$_2$ and Fab fragments and a recombinant single chain fragment variable (scFv) as valuable tools for studying the hypothesized mechanism mediated by mAb 2c. The homogeneity of the generated antibody preparations was monitored by size exclusion chromatography (data not shown). Flow cytometry analysis using Vero cells either infected or not infected with HSV-1 or HSV-2, respectively, demonstrated specific binding of mAb 2c and mAb 2c derived antibody fragments (data not shown). We further used fluorescence cytometry to determine equilibrium binding curves of the antibodies to HSV-1 and HSV-2 infected Vero cells (FIG. 17). The results of these studies demonstrated higher apparent affinities for the whole IgG and the F(ab')$_2$ fragment than for the Fab and scFv, respectively (Table 6). The increment in functional affinity (avidity) for the bivalent antibodies relative to the determined affinities of the monovalent antibodies indicates that the bivalent antibodies were able to bind two gB epitopes on the cell surface simultaneously. Bivalent mAb 2c and 2c-F(ab')$_2$ showed an 1.7-2.8 fold higher apparent affinity compared to their monovalent counterparts. The slight increment in the apparent K$_D$ of the F(ab')$_2$ fragment versus the IgG might be due to the higher flexibility of the antigen binding sites within the F(ab')$_2$ construct. The similar apparent affinities for mAb 2c, 2c-F(ab')$_2$, and 2c-Fab to both, HSV-1 and HSV-2 infected Vero cells confirmed that the recognized gB-epitope does not structurally differ between both viruses (Table 6).

TABLE 6

Apparent equilibrium constants of mAb 2c and derived antibody fragments for binding to HSV-1 F or HSV-2 G infected Vero cells.

| $^{a}K_D$ (nM) | IgG | F(ab')$_2$ | Fab | scFv |
| --- | --- | --- | --- | --- |
|  | bivalent | | monovalent | |
| HSV-1 F | 10.2 | 6.9 | 17.3 | 19.2 |
| HSV-2 G | 10.7 | 8.8 | 17.7 | n.d. |

$^{a}K_D$ values for binding to gB on HSV-infected cells were determined by fitting the data from the equilibrium binding curves determined by flow cytometry (FIG. 17) to the Marquardt-Levenberg equation.

Neutralization Activity of Monovalent and Bivalent Antibodies In Vitro.

Figure 18A:
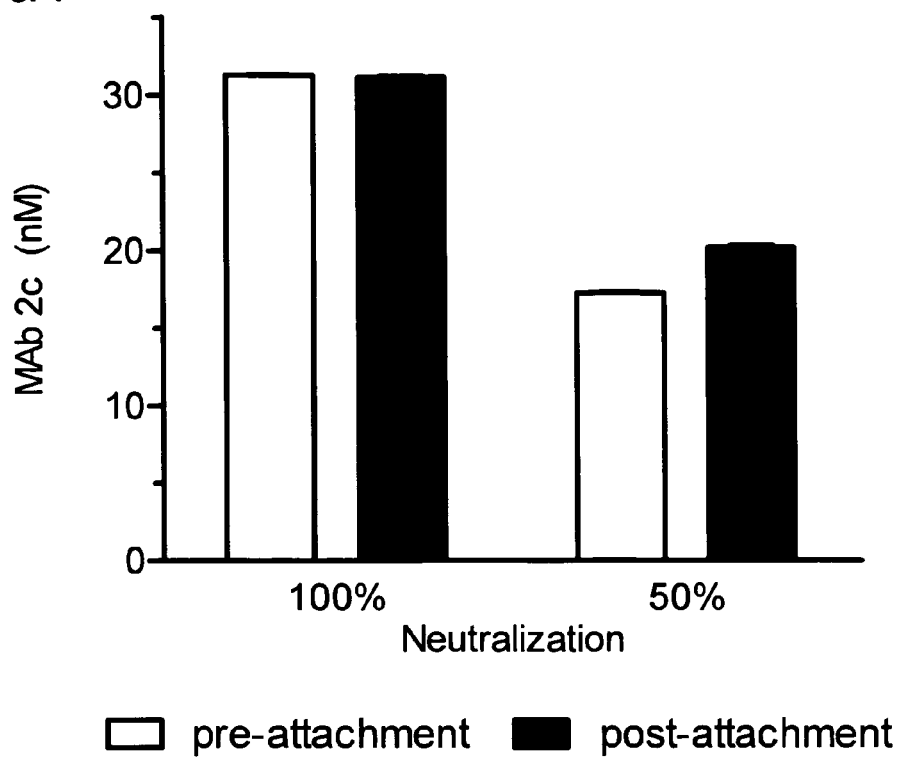
FIG. 18 shows the inhibition of HSV-1 virion attachment by mAb 2c to target cells. Serial dilutions of (A) mAb 2c (0.98-125 nM) or (B) polyvalent human gamma globulin) (Intratect®) (0.33-42 μM) were added to Vero cell monolayers in 96-well microtiter plates following pre-incubation with 100 $TCID_{50}$ HSV-1 (pre-attachment neutralization) or post-adsorbtion of 100 $TCID_{50}$ HSV-1 to target cells (post-attachment neutralization). The highest antibody and polyvalent human IgG titer, respectively, preventing virus induced cytopathic effect (CPE) in ten individual inoculated cell monolayers to 100% and 50% relative to controls were determined after 72 h incubation at 37° C. and being considered as the endpoint. Standard errors of the mean of three independent experiments were <0.1.
Figure 18B:
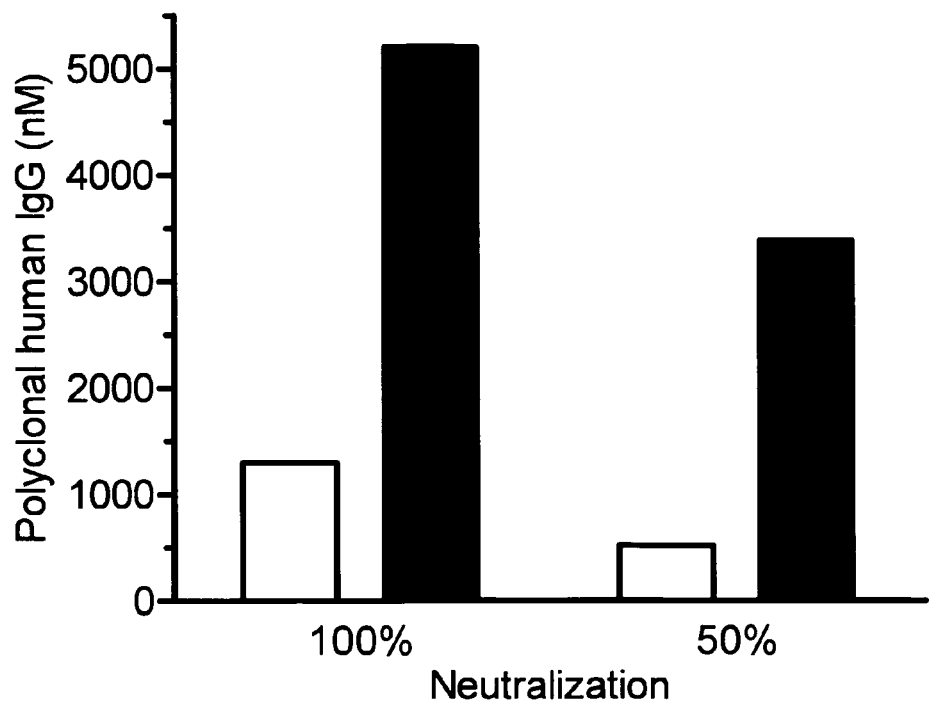
Figure 19A:
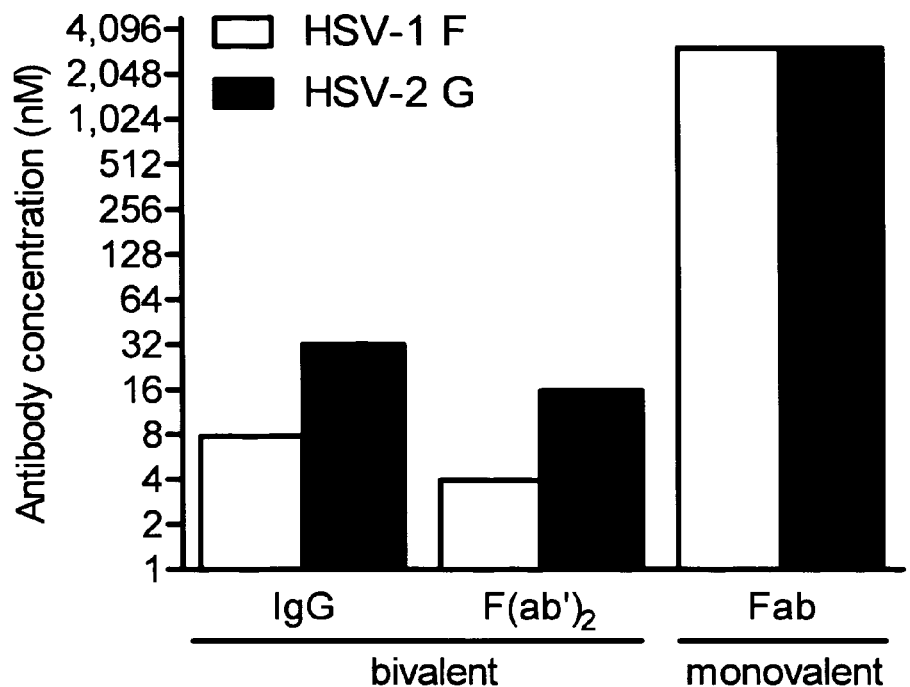
FIG. 19 shows the effect of valency of anti-gB antibodies on in vitro neutralization of HSV. (A) Dilutions of bivalent antibodies mAb 2c (IgG) and 2c-F(ab')$_2$, and monovalent 2c-Fab were incubated for 1 h with 100 $TCID_{50}$ HSV-1 F or HSV-2 G before inoculation onto Vero cells. CPE was scored 72 h later as described in FIG. 3. Shown are antibody concentrations required to neutralize 100% of the viral inoculum from one of three representative replicate experiments. (B) Antiviral activity of 2c-Fab fragments cross-linked with murine anti-Fab IgGs.

Equal neutralization efficacy of mAb 2c irrespective if the antibody was added before (preattachment) or after (postattachment) HSV-1 virions interacted with Vero cells (FIG. 18A) indicated that mAb 2c does not interfere with virus-binding to target cells. In contrast, the polyclonal human gamma globulin Intratect® clearly neutralized by inhibition of virion attachment to target cells (FIG. 18B). Neutralizing activities of mAb 2c derived fragments F(ab')$_2$, Fab and scFv were compared with their parental IgG counterpart in a standard neutralization assay on Vero cells. The parental mAb 2c reduced HSV-1 induced cytopathic effect (CPE) by 100% at a concentration of 8 nM. Interestingly, a 4-fold higher mAb 2c concentration was required to completely reduce HSV-2 induced CPE (FIG. 19A). The bivalent 2c-F(ab')$_2$ reduced both HSV-1 and HSV-2 induced CPE two times more efficiently than the parental mAb 2c. Surprisingly, we observed a fundamental difference in the ability of the monovalent 2c-antibody fragments for neutralizing HSV-1 and HSV-2. Compared to the parental mAb 2c, approx. 375-fold and 94-fold higher concentrations of 2c-Fab were necessary to reduce HSV-1 and HSV-2 induced CPE by 100%, respectively (FIG. 19A). The recombinant 2c-scFv showed a plaque reductive effect under the light microscope, but was not able to reduce HSV induced CPE by 100% even at the highest tested concentration of 3,000 nM (data not shown).

Since both bivalent antibodies mAb 2c and 2c-F(ab')$_2$ neutralized HSV-2 about four-times less effectively than HSV-1 (FIG. 19A) we analyzed the genome copy numbers of HSV-1 and HSV-2 preparations containing equal amounts of infectious particles by quantitative real-time PCR. Compared to HSV-1 a fourfold higher number of genome equivalents was found for HSV-2 (data not shown) correlating well with the higher antibody titer of mAb 2c and 2c-F(ab')$_2$ required for HSV-2 neutralization.

Figure 19B:
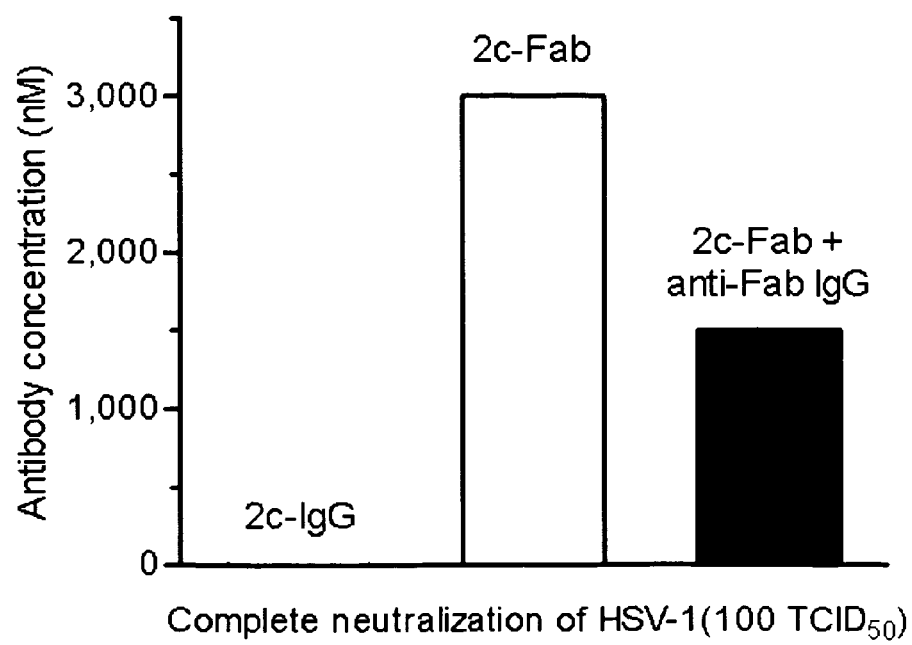

Neutralization assays as shown in FIG. 19A indicated a strong correlation between antibody valency and neutralization efficiency. Consequently, we investigated whether the ability of 2c-Fab fragments for clearing virus infection could be restored by cross linkage of the Fab to fragments. The virus neutralization assay was repeated for 2c-Fab in the absence or presence of IgGs reacting with murine Fab fragments. As shown in FIG. 19B, cross-linking of 2c-Fab dramatically increased neutralizing activity but could not restore it to the same efficacy as for the parental mAb 2c. Anti-murine Fab IgGs alone showed no effect on virus neutralization (data not shown).

Cell-to-Cell Spread Inhibition.

Although 2c-Fab fragments did not efficiently neutralize free virions, yet it was reported that small sized antibody fragments have more favourable diffusion properties (66), we investigated their activity for preventing HSV-1 from crossing cell junctions from infected to uninfected cells. Both bivalent antibodies, mAb 2c and 2c-F(ab')$_2$, completely abrogated HSV-1 spread in Vero cell monolayers and only single infected cells could be visualized by indirect immunofluorescence (FIG. 9). Despite the ability of the polyclonal human serum to neutralize free virions it completely failed to inhibit viral cell-to-cell spread. This is most likely the result of the heterogeneous population of neutralizing antibodies directed against numerous HSV epitopes. Compared with polyclonal human immune serum, the monovalent 2c-Fab fragment was capable to control the cell-to-cell spread to some extend. However, in contrast to its bivalent counterparts, the monovalent 2c-Fab fragment was not able to completely abrogate viral spread even tested at a 6-fold higher concentration (FIG. 9). Hence, antibody valency played a key role also in inhibiting spread of HSV-1 between adjacent cells.

Immunoprotection of Immunodeficient Mice Against Disseminated HSV Infection.

Figure 20:
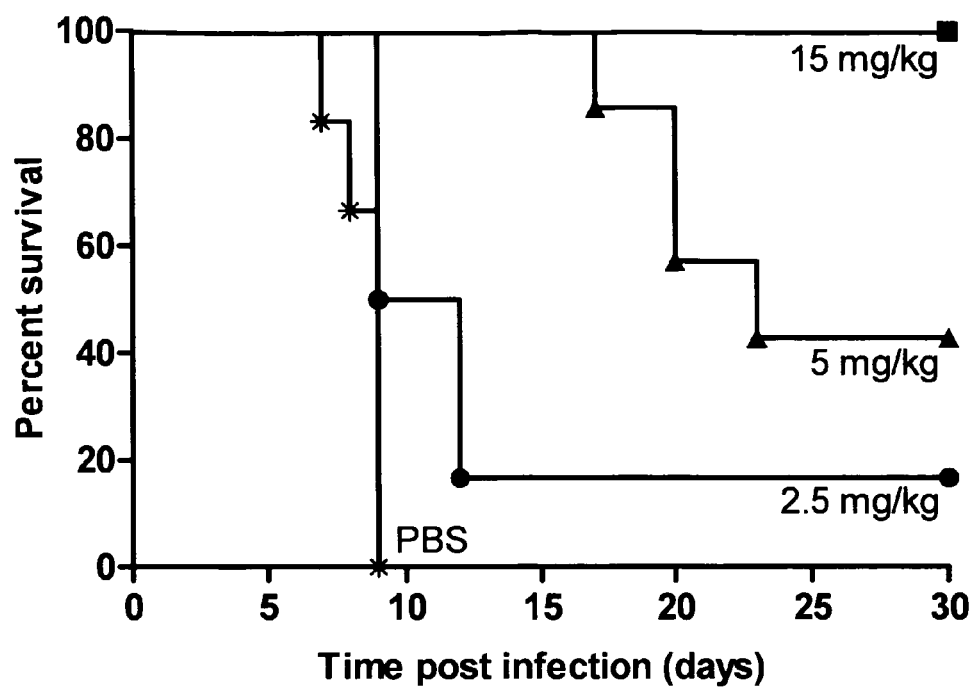
FIG. 20 shows the dose-dependent survival of mAb 2c treated immunodeficient mice. NOD/SCID mice received different single dosages of mAb 2c intravenously 24 h before intravaginal challenge with 1×10$^6$ $TCID_{50}$ HSV-1. Animals per group n=7 for PBS, n=9 all other groups.

We showed previously that mice depleted of both CD4$^+$ and CD8$^+$ T-cells were fully protected from lethal encephalitis by passive transfer of mAb 2c after intravaginally HSV-1 infection (17). Natural killer (NK) cells accumulating at the site of HSV-2 infection in humans (28) are the early source of interferon-γ (45), which plays an essential role for the control of HSV infection (2, 45, 62). More recently it has been demonstrated for the first time, that human NK cells mediate protection against primary genital HSV infection in humanized mice as an innate immune response (37). To investigate, if mAb 2c confers antiviral activity independently from an antibody-mediated immune response we employed a NOD/SCID mouse model, which in addition to the SCID T- and B-cell deficiency, lack NK cell and macrophage function and the ability to stimulate the complement pathway. Intravaginal HSV-1 infection (1×10$^6$ TCID$_{50}$) of NOD/SCID mice resulted in rapid progressive systemic disease with a median survival time of 9 days. HSV titers in organs were determined by an endpoint dilution assay showing high viral titers in spinal cord (2.3×10$^6$ TCID$_{50}$), brain (3.8×10$^5$ TCID$_{50}$), and vaginal mucosa (1.4×10$^6$ TCID$_{50}$), moderate titers in kidney (1.7×10$^4$ TCID$_{50}$) and adrenal glands (1.1×10$^4$ TCID$_{50}$) and low titers in lung (1.1×10$^3$ TCID$_{50}$) and heart (1.9×10$^2$ TCID$_{50}$) (data not shown). To assess the therapeutic efficiency of mAb 2c, NOD/SCID mice were treated intravenously with either 2.5 mg/kg, 5 mg/kg or 15 mg/kg antibody 24 h prior to intra-vaginal HSV-1 challenge (FIG. 20). Mice receiving the low antibody doses were not fully protected against lethal infection by HSV-1. Median survival times of mice treated with 5 mg/kg mAb 2c, however, were 2.6-fold prolonged when compared to control mice receiving PBS. The HSV-1 titres in the investigated organs from mice not protected against lethal encephalitis were comparable to the untreated control group. In contrast, full protection of animals was achieved at a dose of 15 mg/kg mAb 2c. Viral titres in organs of mice protected by the antibody were below the detection limit of 1×10$^2$ TCID$_{50}$.

Figure 21:
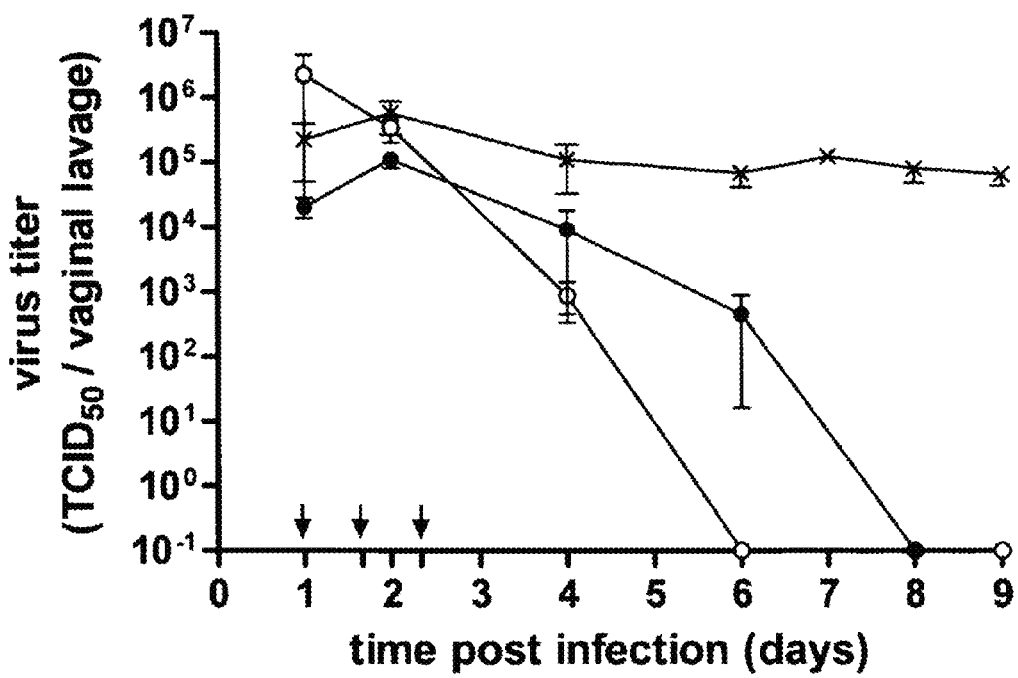
FIG. 21 shows the elimination of an established HSV-1 infections from genital mucous membranes in NOD/SCID mice by systemically applied mAb 2c or humanized mAb hu2c-V1 against HSV-1 dissemination. Starting 24 h post-infection mice received 15 mg/kg mAb 2c (open symbols) or humanized mAb hu2c-V1 (closed symbols) three times intraveniously at time points indicated by arrows (24 h, 40 h, 56 h). Vaginal virus titers of antibody or control treated mice were determined from vaginal irrigations cultured on Vero cell monolayers. Error bars indicate standard deviation.

We next evaluated if post-exposure immunization with mAb 2c also confers protection from viral dissemination and lethal encephalitis in the presence of an established peripheral HSV infection. NOD/SCID mice with a high HSV-1 titer in vaginal irrigations at 24 h after viral challenge were repeatedly treated at 24 h, 40 h and 56 h intravenously with 15 mg/kg of mAb 2c (FIG. 11 and FIG. 21). The PBS treated control group showed constant vaginally virus shedding until mice with neurological symptoms had to be sacrificed between day 7 and day 9. In contrast, mAb 2c cleared established HSV-1 infection by day 8 and completely prevented lethal outcome of infection (3×300 μg; P=0.0003 compared with PBS). Furthermore, no virions were detected in sensory neurons and respective organs of mAb 2c treated animals one month after infection (data not shown).

Discussion

Following the steps viruses take to enter target cells virus-neutralizing mAbs can inhibit entry by several mechanisms. The specific interaction of viral surface proteins with cellular proteins, lipids, or carbohydrates represents the initial stage of infection, which can be blocked by neutralizing antibodies. Antibodies inhibiting virus attachment either directly bind to the virion receptor-binding site, such as mAb F 105 reacting with the CD4-binding site of HIV-1 gp120 and Fab HC19 covering the receptor-binding site of influenza hemagglutinin (HA) (6, 19, 54), or sterically interfere with receptor engagement, such as Fab HC45 binding in 17 Å proximity to the HA receptor-binding site (18). In addition to the essential binding of HSV gD to one of its cellular receptors, gB plays a role in virion attachment to target cells. Recently, the existence of two heparan sulfate proteoglycan independent true cell surface receptors and/or attachment factors for HSV gB have been described (5, 23, 60). Paired immunoglobulin-like type 2 receptor (PILRα) has been characterized as one possible protein receptor of gB at least in certain cell types (60). For mAb 2c comparative pre-versus postattachment neutralization assays showed that the antibody may not inhibit binding of virus to the cell surface, but blocks viral entry. It has been shown previously that the interaction of gB with lipid membranes via key hydrophobic and hydrophilic residues of its fusion domain (22, 23) can be blocked by mAbs that recognize epitopes in close proximity to the fusion loops (4, 22). Because the conformational epitope of mAb 2c partially overlaps with fusion loop 1 we reasoned that binding of mAb 2c interferes most likely with transmission of the fusogenic signal and we further evaluated neutralization at the post-binding/pre-fusion stage as possible mode of action.

Triggered structural rearrangement is a key feature of viral fusogenic glycoproteins, resulting in distinct prefusion and postfusion conformations. Epitopes of different neutralizing mAbs have been mapped along the lateral domains of the spikes and to the tip of the crown of the gB crystal structure (4, 24). The epitope of mAb 2c maps to a unique functional region (FR1) at the base of the gB trimer consisting of residues within the C-terminal helix αF of domain V and residues within domain I of a proximate protomer (4). Our homology model shows that one part of the discontinuous epitope ($F_{300}$ to $E_{305}$) recognized by mAb 2c localizes to the upper section of domain I of gB, which has characteristics of a pleckstrin homology (PH) domain (7, 38). The other part of the epitope ($F_{175}$ to $A_{190}$) also located in domain I, however, is buried and would be inaccessible to mAb 2c binding unless gB undergoes a major conformational change. We therefore hypothesized that mAb 2c impedes transition of gB preferentially in the prefusion conformation. Based on the mAb 2c epitope localization and the assumption that conformational changes upon activation are cooperative, we reasoned that monovalent interaction of mAb 2c would be sufficient for blocking juxtaposition of the fusogenic domain of gB and the cellular membrane. Surprisingly, however, none of the generated monovalent antibody fragments (Fab and scFv) was capable to efficiently neutralize free virions or to inhibit viral cell-to-cell spread. In contrast, both bivalent molecules, mAb 2c and 2c-F(ab')$_2$, were highly effective for virus neutralization and cell-to-cell spread inhibition. Retention of specific and comparable binding activity of all mAb 2c derived antibodies in this study exclude functional differences of monovalent and bivalent antibodies due to impaired antigen recognition. Multivalent binding of immunoglobulins augments their functional affinity (26). The gain in functional affinity, however, inversely correlates with the intrinsic affinity of the antibody binding site (49). The only moderate increment in equilibrium constants between 1.7 and 2.8 for the bivalent 2c antibodies, IgG and F(ab')$_2$ when compared to their monovalent counterparts, scFv and Fab, is thus not unusual for antibodies with intrinsic affinities in the low nanomolar range. Thus the higher apparent affinity in fact indicates that multivalent (higher avidity) binding to the gB antigen does occur and suggests that the anti-viral activity of the mAb 2c and 2c-F (ab')$_2$ is a consequence of gB cross-linking. Inferior neutralization efficiency of monovalent versus bi- or multivalent antibodies with specificity for the gH antigen of varicella-zoster virus (VZV) has been discussed as a matter of steric hindrance due to the different sizes of these antibodies (15). Although we cannot completely exclude this possibility as a potential additional neutralization mechanism for the mAb 2c variants, this seems unlikely because a direct correlation between antibody size, neutralization efficiency, and cell-to-cell spread inhibition was not observed. Furthermore, our data show that the smaller 2c-F(ab')$_2$ had an even better virus neutralization activity than the larger 2c-IgG. Hence, the present observations indicate that gB cross-linking is the key mechanism for the antiviral activity of mAb 2c and suggest that stabilization of the gB prefusion conformation through immobilization of gB trimers inhibits activation of the fusogenic signal. A most recent study by Silverman et al. (61) proposed that a fusion-deficient phenotype of the HSV-1 gB ectodomain upon insertion of five amino acids after residue $E_{187}$ close to the fusion loop 1 may not result from interference with conformational changes of gB but rather from interference with other mechanistic gB functions. In our duotope scans mAb 2c reacted strongest with binding site A/B duotope $_{186}FED_{188}$-βA-βA-$_{300}FYGYRE_{305}$ (SEQ ID NO: 23) covering the particular insertion site $E_{187}$, which seems to be critical for gB function. It is therefore tempting to speculate that mAb 2c crosslinking impairs the ability of gB to interact with the other components of the HSV fusion machinery. However, future research is necessary, since our results do not allow to distinguish if cross-linking blocks the conformational change of gB itself or blocks the interaction between gB, gD and gH/gL, which occurs during cell fusion (3) and is essential for completing the fusion process (65). The HSV-1 gB conformation observed in the solved crystals (24) suggest to represent the postfusion form and a prefusion model of gB has not yet been characterized. Therefore, X-ray crystallographic studies of mAb 2c or its F(ab')$_2$ in complex with gB might provide insights in the native conformation of gB and a better understanding about transmission of the fusogenic signal.

Studies evaluating the protective efficacy of topically applied anti-gD and anti-gB antibodies for preventing vaginal transmission of HSV-2 infection in mice demonstrated the feasibility of engineered recombinant antibodies as new vaginal microbicides (67-69). Severe and even life-threatening HSV infections can occur in maternally infected newborns, in patients with recurrent ocular infections, or in severely immunocompromised patients. To investigate if systemic application of our anti-gB antibody confers protection also in a highly immunodeficient in vivo setting, we employed a NOD/SCID mouse model. We used intravaginal HSV-1 inoculation as an established route of ganglionic infection with axonal spread of the virus causing hindlimb paralysis and fatal herpetic encephalitis in immunocompetent as well as in T cell depleted mice (16, 17). Here we demonstrate, that mAb 2c not only fully protects NOD/SCID in the acute phase of primary HSV-1 infection but is also effective in completely preventing neurological disease and death even after peripheral virus spread has commenced. The HSV cell-to-cell spread is a very efficient way for viral transfer across neuronal synapses and tight junctions as well as to circumvent immunological barriers of the adaptive immune system. MAb 2c both decreases virus expression of infected vaginal tissues and inhibits axonal spread of HSV. Other reports showed that administration of anti-HSV IgGs after viral challenge can reduce the quantity of acute ganglionic infections in animals (16, 42). Consistently, intraperitoneally administered recombinant human anti-gD IgG to mice with corneal HSV-1 infection was shown to localize to HSV-infected nerve fibers and sensory neurons (59). Furthermore, passive immunization of immunocompetent animals with mAbs specific for HSV gD, gC or gB administered postexposure at appropriate times demonstrated protection against HSV induced neurological disease (13, 16). However, it has also been concluded from several animal studies that humoral immunity alone is ineffective in the control of HSV infections.

In vivo protective potency of our antibody is independent from immune effector functions It has also been concluded from several animal studies in the literature that humoral immunity alone is ineffective in the control of HSV infections. Consistent with this view, administration of anti-HSV-1 hyperimmune serum has been reported to be ineffective for protecting immunosupressed or immunodeficient mice (47, 48, 50, 51, 56). Systemic treatment of athymic nude mice 24 h post HSV-1 infection with a human anti-gD mAb prolonged survival compared to untreated controls but did not prevent death (58). Another study showed in an HSV-1 induced stromal keratitis mouse model, that an anti-gD mAb prevented death of mice depleted in either CD4$^+$ or CD8$^+$ T-cells but failed to prevent death when mice were depleted in both T-cell subsets simultaneously (64).

To our knowledge, we demonstrated for the first time protective efficacy of a systemically applied anti-gB cross-linking mAb that prevents neuronal HSV-1 spread completely independent from cellular effector mechanisms and complement. Specificity of mAb 2c for a type-common epitope of gB which is essential for HSV replication and its high protective efficiency without the requirement for recruiting additional immune effector functions indicates a great potential for this antibody as a novel immunotherapeutic.

Reference List For Example 3
1. Arndt, M. A., J. Krauss, R. Schwarzenbacher, B. K. Vu, S. Greene, and S. M. Rybak. 2003. Generation of a highly stable, internalizing anti-CD22 single-chain Fv fragment for targeting non-Hodgkin's lymphoma. Int J Cancer 107: 822-829.
2. Ashkar, A. A., and K. L. Rosenthal. 2003. Interleukin-15 and natural killer and NKT cells play a critical role in innate protection against genital herpes simplex virus type 2 infection. J Virol 77:10168-10171.
3. Atanasiu, D., J. C. Whitbeck, T. M. Cairns, B. Reilly, G. H. Cohen, and R. J. Eisenberg. 2007. Bimolecular complementation reveals that glycoproteins gB and gH/gL of herpes simplex virus interact with each other during cell fusion. Proc Natl Acad Sci USA 104:18718-18723.
4. Bender, F. C., M. Samanta, E. E. Heldwein, M. P. de Leon, E. Bilman, H. Lou, J. C. Whitbeck, R. J. Eisenberg, and G. H. Cohen. 2007. Antigenic and mutational analyses of herpes simplex virus glycoprotein B reveal four functional regions. J Virol 81:3827-3841.
5. Bender, F. C., J. C. Whitbeck, H. Lou, G. H. Cohen, and R. J. Eisenberg. 2005. Herpes simplex virus glycoprotein B binds to cell surfaces independently of heparan sulfate and blocks virus entry. J Virol 79:11588-11597.
6. Bizebard, T., B. Gigant, P. Rigolet, B. Rasmussen, O. Diat, P. Bosecke, S. A. Wharton, J. J. Skehel, and M. Knossow. 1995. Structure of influenza virus haemagglutinin complexed with a neutralizing antibody. Nature 376:92-94.
7. Blomberg, N., E. Baraldi, M. Nilges, and M. Saraste. 1999. The PH superfold: a structural scaffold for multiple functions. Trends Biochem Sci 24:441-445.
8. Brown, Z. A., J. Benedetti, R. Ashley, S. Burchett, S. Selke, S. Berry, L. A. Vontver, and L. Corey. 1991. Neonatal herpes simplex virus infection in relation to asymptomatic maternal infection at the time of labor. N Engl J Med 324:1247-1252.
9. Burbelo, P. D., Y. Hoshino, H. Leahy, T. Krogmann, R. L. Hornung, M. J. Iadarola, and J. I. Cohen. 2009. Serological diagnosis of human herpes simplex virus type 1 and 2 infections by luciferase immunoprecipitation system assay. Clin Vaccine Immunol 16:366-371.
10. Carter, C., S. Savic, J. Cole, and P. Wood. 2007. Natural killer cell receptor expression in patients with severe and recurrent Herpes simplex virus-1 (HSV-1) infections. Cell Immunol 246:65-74.
11. Cook, M. L., and J. G. Stevens. 1973. Pathogenesis of herpetic neuritis and ganglionitis in mice: evidence for intra-axonal transport of infection. Infect Immun 7:272-288.
12. Cunningham, A. L., R. R. Turner, A. C. Miller, M. F. Para, and T. C. Merigan. 1985. Evolution of recurrent herpes simplex lesions. An immunohistologic study. J Clin Invest 75:226-233.
13. Dix, R. D., L. Pereira, and J. R. Baringer. 1981. Use of monoclonal antibody directed against herpes simplex virus glycoproteins to protect mice against acute virus-induced neurological disease. Infect Immun 34:192-199.
14. Donaghy, H., L. Bosnjak, A. N. Harman, V. Marsden, S. K. Tyring, T. C. Meng, and A. L. Cunningham. 2009. Role for plasmacytoid dendritic cells in the immune control of recurrent human herpes simplex virus infection. J Virol 83:1952-1961.
15. Drew, P. D., M. T. Moss, T. J. Pasieka, C. Grose, W. J. Harris, and A. J. Porter. 2001. Multimeric humanized varicella-zoster virus antibody fragments to gH neutralize virus while monomeric fragments do not. J Gen Virol 82:1959-1963.
16. Eis-Hubinger, A. M., K. Mohr, and K. E. Schneweis. 1991. Different mechanisms of protection by monoclonal and polyclonal antibodies during the course of herpes simplex virus infection. Intervirology 32:351-360.
17. Eis-Hubinger, A. M., D. S. Schmidt, and K. E. Schneweis. 1993. Anti-glycoprotein B monoclonal antibody protects T cell-depleted mice against herpes simplex virus infection by inhibition of virus replication at the inoculated mucous membranes. J Gen Virol 74 (Pt 3):379-385.
18. Fleury, D., B. Barrere, T. Bizebard, R. S. Daniels, J. J. Skehel, and M. Knossow. 1999. A complex of influenza hemagglutinin with a neutralizing antibody that binds outside the virus receptor binding site. Nat Struct Biol 6:530-534.
19. Fleury, D., S. A. Wharton, J. J. Skehel, M. Knossow, and T. Bizebard. 1998. Antigen distortion allows influenza virus to escape neutralization. Nat Struct Biol 5:119-123.
20. Frank, R., and H. Overwin. 1996. SPOT synthesis. Epitope analysis with arrays of synthetic peptides prepared on cellulose membranes. Methods Mol Biol 66:149-169.
21. Grubor-Bauk, B., A. Simmons, G. Mayrhofer, and P. G. Speck. 2003. Impaired clearance of herpes simplex virus 21. type 1 from mice lacking CD1d or NKT cells expressing the semivariant V alpha 14-J alpha 281 TCR. J Immunol 170:1430-1434.
22. Hannah, B. P., T. M. Cairns, F. C. Bender, J. C. Whitbeck, H. Lou, R. J. Eisenberg, and G. H. Cohen. 2009. Herpes simplex virus glycoprotein B associates with target membranes via its fusion loops. J Virol 83:6825-6836.
23. Hannah, B. P., E. E. Heldwein, F. C. Bender, G. H. Cohen, and R. J. Eisenberg. 2007. Mutational evidence of internal fusion loops in herpes simplex virus glycoprotein B. Virol 81:4858-4865.
24. Heldwein, E. E., H. Lou, F. C. Bender, G. H. Cohen, R. J. Eisenberg, and S. C. Harrison. 2006. Crystal structure of glycoprotein B from herpes simplex virus 1. Science 313:217-220.
25. Highlander, S. L., W. H. Cai, S. Person, M. Levine, and J. C. Glorioso. 1988. Monoclonal antibodies define a domain on herpes simplex virus glycoprotein B involved in virus penetration. J Virol 62:1881-1888.
26. Kaufman, E. N., and R. K. Jain. 1992. Effect of bivalent interaction upon apparent antibody affinity: experimental confirmation of theory using fluorescence photobleaching and implications for antibody binding assays. Cancer Res 52:4157-4167.
27. Kipriyanov, S. M., O. A. Kupriyanova, M. Little, and G. Moldenhauer. 1996. Rapid detection of recombinant antibody fragments directed against cell- surface antigens by flow cytometry. J Immunol Methods 196:51-62.
28. Koelle, D. M., C. M. Posavad, G. R. Barnum, M. L. Johnson, J. M. Frank, and L. Corey. 1998. Clearance of HSV-2 from recurrent genital lesions correlates with infiltration of HSV-specific cytotoxic T lymphocytes. J Clin Invest 101:1500-1508.
29. Kohl, S. 1991. Role of antibody-dependent cellular cytotoxicity in defense against herpes simplex virus infections. Rev Infect Dis 13:108-114.
30. Kohl, S., D. L. Cahall, D. L. Walters, and V. E. Schaffner. 1979. Murine antibody-dependent cellular cytotoxicity to herpes simplex virus-infected target cells. J Immunol 123:25-30.
31. Kohl, S., N.C. Strynadka, R. S. Hodges, and L. Pereira. 1990. Analysis of the role of antibody-dependent cellular cytotoxic antibody activity in murine neonatal herpes simplex virus infection with antibodies to synthetic peptides of glycoprotein D and monoclonal antibodies to glycoprotein B. J Clin Invest 86:273-278.
32. Kohl, S., M. S. West, C. G. Prober, W. M. Sullender, L. S. Loo, and A. M. Arvin. 1989. Neonatal antibody-dependent cellular cytotoxic antibody levels are associated with the clinical presentation of neonatal herpes simplex virus infection. J Infect Dis 160:770-776.
33. Kousoulas, K. G., B. Huo, and L. Pereira. 1988. Antibody-resistant mutations in cross-reactive and type-specific epitopes of herpes simplex virus 1 glycoprotein B map in separate domains. Virology 166:423-431.
34. Kramer, A., and J. Schneider-Mergener. 1998. Synthesis and screening of peptide libraries on continuous cellulose membrane supports. Methods Mol Biol 87:25-39.
35. Krummenacher, C., V. M. Supekar, J. C. Whitbeck, E. Lazear, S. A. Connolly, R. J. Eisenberg, G. H. Cohen, D.C. Wiley, and A. Carfi. 2005. Structure of unliganded HSV gD reveals a mechanism for receptor-mediated activation of virus entry. EMBO J. 24:4144-4153.
36. Kuhn, J. E., G. Dunkler, K. Munk, and R. W. Braun. 1987. Analysis of the IgM and IgG antibody response against herpes simplex virus type 1 (HSV-1) structural and non-structural proteins. J Med Virol 23:135-150.
37. Kwant-Mitchell, A., A. A. Ashkar, and K. L. Rosenthal. 2009. Mucosal innate and adaptive immune responses against herpes simplex virus type 2 in a humanized mouse model. J Virol 83:10664-10676.
38. Lemmon, M. A., and K. M. Ferguson. 2000. Signal-dependent membrane targeting by pleckstrin homology (PH) domains. Biochem J 350 Pt 1:1-18.
39. Li, W., T. J. Minova-Foster, D. D. Norton, and M. I. Muggeridge. 2006. Identification of functional domains in herpes simplex virus 2 glycoprotein B. J Virol 80:3792-3800.
40. Lin, E., and P. G. Spear. 2007. Random linker-insertion mutagenesis to identify functional domains of herpes simplex virus type 1 glycoprotein B. Proc Natl Acad Sci USA 104:13140-13145.
41. Lingen, M., F. Hengerer, and D. Falke. 1997. Mixed vaginal infections of Balb/c mice with low virulent herpes simplex type 1 strains result in restoration of virulence properties: vaginitis/vulvitis and neuroinvasiveness. Med Microbiol Immunol 185:217-222.
42. McKendall, R. R., T. Klassen, and J. R. Baringer. 1979. Host defenses in herpes simplex infections of the nervous system: effect of antibody on disease and viral spread. Infect Immun 23:305-311.
43. Mester, J. C., J. C. Glorioso, and B. T. Rouse. 1991. Protection against zosteriform spread of herpes simplex virus by monoclonal antibodies. J Infect Dis 163:263-269.
44. Mikloska, Z., A. M. Kesson, M. E. Penfold, and A. L. Cunningham. 1996. Herpes simplex virus protein targets for CD4 and CD8 lymphocyte cytotoxicity in cultured epidermal keratinocytes treated with interferon-gamma. J Infect Dis 173:7-17.
45. Milligan, G. N., and D. I. Bernstein. 1997. Interferon-gamma enhances resolution of herpes simplex virus type 2 infection of the murine genital tract. Virology 229:259-268.
46. Milligan, G. N., D. I. Bernstein, and N. Bourne. 1998. T lymphocytes are required for protection of the vaginal mucosae and sensory ganglia of immune mice against reinfection with herpes simplex virus type 2. J Immunol 160:6093-6100.
47. Minagawa, H., S. Sakuma, S. Mohri, R. Mori, and T. Watanabe. 1988. Herpes simplex virus type 1 infection in mice with severe combined immunodeficiency (SCID). Arch Virol 103:73-82.
48. Nagafuchi, S., H. Oda, R. Mori, and T. Taniguchi. 1979. Mechanism of acquired resistance to herpes simplex virus infection as studied in nude mice. J Gen Virol 44:715-723.
49. Nielsen, U. B., G. P. Adams, L. M. Weiner, and J. D. Marks. 2000. Targeting of bivalent anti-ErbB2 diabody antibody fragments to tumor cells is independent of the intrinsic antibody affinity. Cancer Res 60:6434-6440.
50. Oakes, J. E. 1975. Invasion of the central nervous system by herpes simplex virus type 1 after subcutaneous inoculation of immunosuppressed mice. J Infect Dis 131:51-57.
51. Oakes, J. E. 1975. Role for cell-mediated immunity in the resistance of mice to subcutaneous herpes simplex virus infection. Infect Immun 12:166-172.
52. Pereira, L., M. Ali, K. Kousoulas, B. Huo, and T. Banks. 1989. Domain structure of herpes simplex virus 1 glycoprotein B: neutralizing epitopes map in regions of continuous and discontinuous residues. Virology 172:11-24.
53. Pereira, L., T. Klassen, and J. R. Baringer. 1980. Type-common and type-specific monoclonal antibody to herpes simplex virus type 1. Infect Immun 29:724-732.
54. Posner, M. R., T. Hideshima, T. Cannon, M. Mukherjee, K. H. Mayer, and R. A. Byrn. 1991. An IgG human monoclonal antibody that reacts with HIV-1/GP120, inhibits virus binding to cells, and neutralizes infection. J Immunol 146:4325-4332.
55. Qadri, I., C. Gimeno, D. Navarro, and L. Pereira. 1991. Mutations in conformation-dependent domains of herpes simplex virus 1 glycoprotein B affect the antigenic properties, dimerization, and transport of the molecule. Virology 180:135-152.
56. Rager-Zisman, B., and A. C. Allison. 1976. Mechanism of immunologic resistance to herpes simplex virus 1 (HSV-1) infection. J Immunol 116:35-40.
57. Reed, J. L., and H. Muench. 1938. A simple method of estimating fifty percent endpoints. Am J Hyg 27:493-497.
58. Sanna, P. P., A. De Logu, R. A. Williamson, Y. L. Hom, S. E. Straus, F. E. Bloom, and D. R. Burton. 1996. Protection of nude mice by passive immunization with a type-common human recombinant monoclonal antibody against HSV. Virology 215:101-106.
59. Sanna, P. P., T. J. Deerinck, and M. H. Ellisman. 1999. Localization of a passively transferred human recombinant monoclonal antibody to herpes simplex virus glycoprotein D to infected nerve fibers and sensory neurons in vivo. J Virol 73:8817-8823.
60. Satoh, T., J. Arii, T. Suenaga, J. Wang, A. Kogure, J. Uehori, N. Arase, I. Shiratori, S. Tanaka, Y. Kawaguchi, P. G. Spear, L. L. Lanier, and H. Arase. 2008. PILRalpha is a herpes simplex virus-1 entry coreceptor that associates with glycoprotein B. Cell 132:935-944.
61. Silverman, J. L., S. Sharma, T. M. Cairns, and E. E. Heldwein. 2010. Fusion-deficient insertion mutants of herpes simplex virus type 1 glycoprotein B adopt the trimeric postfusion conformation. J Virol 84:2001-2012.
62. Smith, P. M., R. M. Wolcott, R. Chervenak, and S. R. Jennings. 1994. Control of acute cutaneous herpes simplex virus infection: T cell-mediated viral clearance is dependent upon interferon-gamma (IFN-gamma). Virology 202: 76-88.
63. Spear, P. G., and R. Longnecker. 2003. Herpesvirus entry: an update. J Virol 77:10179-10185.
64. Staats, H. F., J. E. Oakes, and R. N. Lausch. 1991. Anti-glycoprotein D monoclonal antibody protects against herpes simplex virus type 1-induced diseases in mice functionally depleted of selected T-cell subsets or asialo GM1+ cells. J Virol 65:6008-6014.
65. Subramanian, R. P., and R. J. Geraghty. 2007. Herpes simplex virus type 1 mediates fusion through a hemifusion intermediate by sequential activity of glycoproteins D, H, L, and B. Proc Natl Acad Sci USA 104:2903-2908.
66. Yokota, T., D. E. Milenic, M. Whitlow, and J. Schlom. 1992. Rapid tumor penetration of a single-chain Fv and comparison with other immunoglobulin forms. Cancer Res 52:3402-3408.
67. Zeitlin, L., P. E. Castle, K. J. Whaley, T. R. Moench, and R. A. Cone. 1998. Comparison of an anti-HSV-2 monoclonal IgG and its IgA switch variant for topical immunoprotection of the mouse vagina. J Reprod Immunol 40:93-101.
68. Zeitlin, L., S. S. Olmsted, T. R. Moench, M. S. Co, B. J. Martinell, V. M. Paradkar, D. R. Russell, C. Queen, R. A. Cone, and K. J. Whaley. 1998. A humanized monoclonal antibody produced in transgenic plants for immunoprotection of the vagina against genital herpes. Nat Biotechnol 16:1361-1364.
69. Zeitlin, L., K. J. Whaley, P. P. Sanna, T. R. Moench, R. Bastidas, A. De Logu, R. A. Williamson, D. R. Burton, and R. A. Cone. 1996. Topically applied human recombinant monoclonal IgG1 antibody and its Fab and F(ab')$_2$ fragments protect mice from vaginal transmission of HSV-2. Virology 225:213-215.

Example 4

Virus Neutralisation Assay

Neutralisation assays were performed in microtiter plates on Vero cells either as plaque reduction assay with an excess amount of antibodies to determine the virus' neutralisation sensitivity or as endpoint dilution method to determine the neutralisation titer of an antibody solution. Plaque reduction assays were performed by incubation of 250 plaque forming units with 20 µg MAb 2c. After two hours 50 µL/well of Vero cell suspension ($1.5 \times 10^5$ cells/mL) were added. After 3 days cells were stained with crystal violet. For endpoint titration, diluted antibody solutions (0.025 mL) were incubated with 100 $TCID_{50}$ of HSV-1 in 0.025 mL, and 0.025 mL guinea pig complement, diluted 1:10. Titers were expressed as reciprocals of the highest serum dilution preventing virus-induced cytopathic effect in 50% of the cultures.

Construction of gB Deletion Mutants and Expression in COS-1 Cells

Construction of the plasmids coding for full length HSV-1 gB (gB(1-904)=pMT$_2$gB), gB(1-720), gB(1-630), gB(1-505), gB(1-503), gB(1-487), and gB(1-470) has been described elsewhere [30, 31]. Plasmids were kindly provided by Leonore Pereira, University of California, San Francisco. Plasmids coding for gB(1-130), gB(1-223), gB(183-488), and gB(436-642) were constructed by cloning PCR amplicons, flanked by the restriction enzyme sites Bam HI and Xho I, into the eukaryotic expression vector pSVL (Amersham Pharmacia, Freiburg, Germany). A subgenomic plasmid clone of HSV-1 strain 17$^{+}$[33; GenBank X14112] containing gB nucleotides 52588 to 60362 was used as template in PCR. For expression of N-terminally truncated gB constructs, the gB signal sequence-coding DNA was amplified by PCR with a primer containing a XhoI site at its 5' end and inserted 5' to the gB-coding DNA of the subfragment plasmids gB(183-488), and gB(436-642). The correct integration of the insert and its sequence were confirmed by nucleotide sequencing. COS-1 cells were grown on coverslips (diameter 10 mm) placed into 24-well plates and transfected with plasmids by the DEAE-dextran method [34]. Expression of gB and its truncated derivatives was verified by indirect immunofluorescence microscopy with a mixture of the well characterized anti-HSV-1 gB mouse monoclonal antibodies H1396 and H1781. Transfected and fixed COS-1 cells were reacted with MAb 2c and analysed by immunofluorescence microscopy.

Site-Directed Mutagenesis of gB and Construction of Recombinant Virus

Single amino acid mutations were introduced in HSV-1 gB by oligonucleotide-directed mutagenesis using the Altered Sites™ in vitro Mutagenesis System (Promega, Mannheim, Germany). In brief, the gB-encoding sequence within pMT$_2$gB [31] was transferred into the *E. coli* phagemid mutagenesis vector pAlter-1. Single stranded pALTER-1gB DNA molecules were prepared by infection of pALTER-1gB transformed *E. coli* JM109 cells with the phage R408. Site directed mutagenesis was performed according to the manufacturer's protocol with the mismatch primers (mutated position underlined) as follows:

Y296N (N = mutation), 5'-GGGACATGTTCACAAAGTC-3'; (SEQ ID NO: 24)

Y296F, 5'-GGG (i.e., shifting along the gB sequence by 3 amino acids), corresponding to gB residues from amino acid 31 to 505 (HSV-1 strain 17+ [33] GenBank X14112), and as 13-mers with an overlap of 12 amino acids (i.e., shifting along the gB sequence by one amino acid) corresponding to gB residues 296 to 315.

To identify the minimal binding motif within the MAb 2c binding site B, a key motif scan was done using 14-mers, composed of a central, gB-derived hexamer embraced by four randomized residues at each, N- and C-terminus $(x_1x_2x_3x_4B_1B_2B_3B_4B_5B_6x_{11}x_{12}x_{13}x_{14}$; x, randomized position, B, fixed gB-derived position) [40]. With each peptide the hexameric sequence was shifted by one amino acid starting at gB position V295 and spanning the sequence up to gB position A315.

The relevance of single amino acids for binding of MAb 2c within gB binding site A was analysed by a substitutional analysis of peptide $_{178}$RYSQFMGIFEDRAPV$_{192}$, (SEQ ID NO: 43) performed by successively exchanging each amino acids by all other 19 natural amino acids as described previously [40-42].

Mice and Mouse Protection Experiments

Female C57BL/6J (H-2$^b$) mice were obtained from Charles River Wiga (Charles River Laboratories, Sulzfeld, Germany), and used when 33 to 37 days old. Experiments were carried out as previously described [1, 2]. In brief, mice were inoculated intravaginally with 2×10$^6$ TCID$_{50}$ of HSV-1 in 0.1 mL EMEM with 10% fetal calf serum. Twenty-four hours before viral inoculation, mice were given by intraperitoneal injection 0.5 mL either of MAb 2c, polyclonal immune serum or precipitated culture medium. The human standard immune serum preparation used (Beriglobin S™, CSL Behring, Germany) had a complement-independent neutralising titre of 1:1280 to HSV-1 in 0.025 mL and was diluted for application fourfold in Iscove's medium. The stock preparation of MAb 2c had a complement-independent neutralising titer of 1:640 and was diluted twofold to contain the same neutralising activity as the polyclonal immune serum. The ELISA titer of the applied antibody dilutions was between 10$^{4.5}$ and 10$^{5.5}$ when determined according to the method of Kahlon & Whitley [43] using peroxidase-conjugated rabbit to mouse and human IgG. For controls, equivalent volumes of Iscove's medium were treated in the same manner. Control mice administered culture medium were equivalent to controls given a non-HSV-specific MAb [1]. Vaginal swabs were taken every second day after viral inoculation and assayed for virus on Vero cell monolayers. Infectious virus titers were determined in microtiter plates by TCID$_{50}$ per 0.05 mL according to the method of Reed & Muench [44].

Results

The First 487 Amino Acids of gB are Necessary for Binding of MAb 2c

To gain first insight into the glycoprotein B region necessary for proper folding of the MAb 2c epitope, a full length HSV-1 gB construct and a set of carboxy-terminally truncated gB constructs were expressed in COS-1 cells as given in the Methods section. Expression of gB was verified by indirect immunofluorescence microscopy using a mixture of the murine HSV gB-specific MAbs H1396 and H1781. Binding of MAb 2c was also visualised by indirect immunofluorescence assay. As shown in Table 7, the full length protein and the truncated derivatives gB(1-720), gB(1-630), gB(1-505), gB(1-503), and gB(1-487) were recognised by MAb 2c. In contrast, MAb 2c failed to bind gB(1-470), gB(1-223), and gB(1-130). Furthermore, no reaction was observed with two constructs with both N- and C-terminal truncation (gB(183-488), gB(436-642)). These results indicated that the epitope of MAb 2c is located within the first 487 amino-terminal residues.

TABLE 7

Binding of MAb 2c to truncated HSV-1 glycoprotein B (gB) expressed in COS-1 cells.

| gB constructs* | Reactivity** |
| --- | --- |
| gB(1-904) (full length gB) | + |
| gB(1-720) | + |
| gB(1-630) | + |
| gB(1-505) | + |
| gB(1-503) | + |
| gB(1-487) | + |
| gB(1-470) | − |
| gB(1-223) | − |
| gB(1-130) | − |
| gB(183-488) | − |
| gB(436-642) | − |
| pSVL*** | − |

*Expression of all gB constructs was confirmed by indirect immuno-fluorescence with the HSV gB-specific monoclonal antibodies H1396 and H1781 [30-32].
**Binding of MAb 2c was detected by indirect immunofluorescence. +, indicates MAb 2c binding, −, indicates failure of MAb 2c binding.
***pSVL, expression vector, used as negative control.

MAb 2c Recognises Sequences of Two Different gB Regions

Since fine-mapping of the epitope recognised by MAb 2c was not possible using gB deletion constructs expressed in COS-1 cells, a gB-derived scan of overlapping peptides (peptide scan) was synthesized on continuous cellulose membrane supports by SPOT™ synthesis. The peptides, spanning the gB region from amino acid 31 to 505, were synthesized as 15-mers, with an overlap of 12 amino acids (i.e., shifting along the gB sequence by 3 amino acids) resulting in a total of 155 peptides. Binding of MAb 2c was shown by simultaneous incubation with primary (MAb 2c) and secondary (POD-conjugated anti-mouse IgG Fab) antibodies and detection by chemiluminescence. As shown in FIG. 22, MAb 2c was found to bind to five peptides within two distinct gB regions, termed sites A and B. Site A comprises three consecutive peptides corresponding to gB residues $_{175}$FGHRYSQFMGIFE-DRAPVPFE$_{195}$ (SEQ ID NO: 44) (common sequence $_{181}$QFMGIFEDR$_{189}$ (SEQ ID NO: 45), and site B two consecutive peptides encompassing residues $_{298}$SPFYGYREGSHTEHTSYA$_{315}$ (SEQ ID NO: 46) (common sequence $_{301}$YGYREGSHTEHT$_{312}$ (SEQ ID NO: 47).

Identification of the Minimal Length of Binding Site B for MAb 2c

Because peptide 90 (FIG. 22; $_{298}$SPFYGYREGSH-TEHT$_{312}$ (SEQ ID NO: 48) exhibited the strongest signal intensity we hypothesized that binding site B is the dominant determinant for MAb 2c binding. Thus, we identified the minimal length of site B required for MAb 2c binding using a higher resolution cellulose-bound peptide scan. 13-mer peptides spanning the gB-derived residues 296 to 315 with an overlap of 12 amino acids (i.e., shifting along the gB sequence by only one amino acid) were synthesized in duplicate. Reactivity of MAb 2c with five consecutive peptides was observed following an incubation and detection procedure as described above. An alignment of the sequences of the five reactive peptides is shown in FIG. 23. The common sequence to all five peptides was $_{300}$FYGYREGSH$_{308}$ (SEQ ID NO: 49).

In a second approach, a key motif scanning method, using 14-mers each consisting of six gB-derived amino acids flanked on both ends by four randomized positions, was applied. In this assay, the four terminal positions of each peptide molecule represented a random sequence in which the amino acids were incorporated statistically. Each spot thus contained a vast mixture of peptides with a multitude of sequences at the outer peptide positions but all with the same gB-derived sequence at the peptide positions five to ten. The gB-derived central hexamers spanned the gB region from residue V295 to A315 and shifted along by one amino acid. A hexameric gB-sequence was chosen because it is known that more than 75% of non-linear epitopes comprise a sequential stretch of a maximum length of 4 to 7 residues [45]. Reactivity of MAb 2c was seen with the two consecutive peptides xxxx$_{300}$FYGYRE$_{305}$xxxx (SEQ ID NO: 21).and xxxx$_{301}$YGYREG$_{306}$xxxx (SEQ ID NO: 50) (FIG. 24). Thus the sequence $_{300}$FYGYREG$_{306}$ (SEQ ID NO: 51) was considered to be the minimal binding motif of site B peptides required for interaction with MAb 2c.

Identification of Individual Residues Critical for MAb 2c Binding at Site B by Mutated gB To confirm the binding site B for MAb 2c in the context of the entire and natively folded protein, we altered the amino acid sequence of the full length gB, cloned in pMT$_2$gB, by single amino acid exchanges within the binding site B. By using a phagemid-based system for site-directed mutagenesis a number of gB constructs with single amino acid exchanges was generated. After expression of the mutated gB in COS-1 cells binding of MAb 2c was analysed by immunofluorescence assay. As shown in Table 8, a series of gB residues was identified that proved to be critical for MAb 2c binding. In detail, substitution of residue P at gB position 299 for S, F300 by Y and I, respectively, Y301 by N, G302 by R and V, respectively, Y303 by N, R304 by G and L, respectively, and E305 by K, resulted in complete loss of MAb 2c binding, thus indicating that each of the residues at positions 299 to 305 are crucially involved in epitope formation, either by representing key residues interacting via their side chains with the antibody or by influencing the proper overall or local folding of the gB protein necessary for forming the conformation of the epitope recognised by the antibody. Expression of the mutated gB in COS-1 cells was verified by co-incubation of the cells with the murine MAb 2c and a polyclonal rabbit anti-HSV IgG immune serum followed by identification via co-incubation with DTAF conjugated anti-mouse IgG (green fluorescence if MAb 2c was bound) and TexasRed or Cy3 conjugated anti-rabbit antibodies (red fluorescence of the same cells). On the contrary, exchange of the single gB residue Y296 for N and F, respectively, M297 for L, T and V, respectively, and S298 for A, as well as G306 for A and V, respectively, and S307 for A did not affect binding of MAb 2c.

TABLE 8

Binding of MAb 2c to HSV-1 full length glycoprotein B (gB) variants containing single amino acid exchanges, expressed in COS-1 cells.

| gB variants | Reactivity** |
| --- | --- |
| Y296N* | + |
| Y296F | + |
| M297L | + |
| M297T | + |
| M297V | + |
| S298A | + |
| P299S | −*** |
| F300Y | − |
| F300I | − |
| Y301N | − |
| G302R | − |
| G302V | − |
| Y303N | − |
| R304G | − |
| R304L | − |
| E305K | − |

TABLE 8-continued

Binding of MAb 2c to HSV-1 full length glycoprotein B (gB) variants containing single amino acid exchanges, expressed in COS-1 cells.

| gB variants | Reactivity** |
| --- | --- |
| G306A | + |
| G306V | + |
| S307A | + |

*The wild-type amino acid is given before the gB position number while the introduced residue is given behind the position number. Expression of all gB variants was confirmed by immunofluorescence obtained by co-incubation of the cells with a polyclonal rabbit anti-HSV-1 IgG serum.
**Binding of MAb 2c was tested by indirect immunofluorescence. +, indicates MAb 2c binding, −, indicates failure of MAb 2c binding.
***For assessment of this particular result, see Discussion section.

Identification of Individual Residues Critical for MAb 2c Binding at Site B by Mutant Viruses To approximate most closely the situations in vivo, the impact of individual amino acids of site B was further analysed by using five well-characterized HSV-1 variants (R126, R1375, B4.1, R1435, R233), each containing an amino acid mutation in gB [27-29] and by mutant viruses (vY301N [Y at position 301 substituted by N], vG302R, vG302V) generated in the present study, as given in the Methods section. Vero cells on cover slides were infected with 200-300 plaque forming units of either these mutants or the parental wild-type viruses HSV-1 F and KOS 321. Indirect immunofluorescence assays demonstrated that MAb 2c failed to bind to cells infected by the viruses vY301N, vG302R, vG302V, R126 (Y303 substituted by N), R1375 (R304Q), and B4.1 (E305K) while MAb 2c was reactive to cells infected with the mutants R1435 (H308Y), R233 (R328H) as well as with the wild-type viruses (Table 9).

TABLE 9

Sensitivity of HSV-1 wild-type viruses and viral gB mutants to binding of and neutralisation by MAb 2c.

| Virus [Ref.] | Binding* | Neutralisation** |
| --- | --- | --- |
| Wild-type strain F [25] | + | + |
| Wild-type strain KOS 321 [26] | + | + |
| Mutant F vY301N*** [this study] | − | − |
| Mutant F vG302R [this study] | − | − |
| Mutant F vG302V [this study] | − | − |
| Mutant F R126 (Y303N) [27, 28] | − | − |
| Mutant F R1375 (R304Q) [27, 28] | − | − |
| Mutant KOS B4.1 (E305K) [29] | − | − |
| Mutant F R1435 (H308Y) [27, 28] | + | + |
| Mutant F R233 (R328H) [27, 28] | + | + |

*Expression of gB was confirmed for all viruses by immunofluorescence obtained with a polyclonal rabbit anti-HSV-1 IgG serum. +, indicates MAb 2c binding to infected Vero cells detected by indirect immunofluorescence, −, indicates failure of MAb 2c binding.
**+, indicates virus neutralisation by MAb 2c, −, indicates failure of virus neutralisation.
***The wild-type amino acid is given before the gB position number while the introduced residue is given behind the position number.

To determine whether the residues identified as critical for binding of MAb 2c to gB were also crucial for the neutralising activity of the antibody, neutralisation assays were performed using 250 plaque forming units of the viral mutants or wild-type viruses. As shown in Table 9, the wild-type strains F and KOS 321 as well as the mutants R1435 (H308Y) and R233 (R328H) were completely neutralised by MAb 2c. In contrast, MAb 2c completely failed to neutralise mutant viruses vY301N, vG302R, vG302V, R126 (Y303N), R1375 (R304Q), and B4.1 (E305K) indicating that each of these residues is an essential target for forming the epitope required for the neutralising capacity of MAb 2c. Taken together, the results obtained by peptide analyses and mutated proteins showed that the residues 299 to 305 are important for epitope formation as well as for the in vitro bioactivity of MAb 2c.

Epitope Mapping by Mouse Protection Experiments

Figure 25:
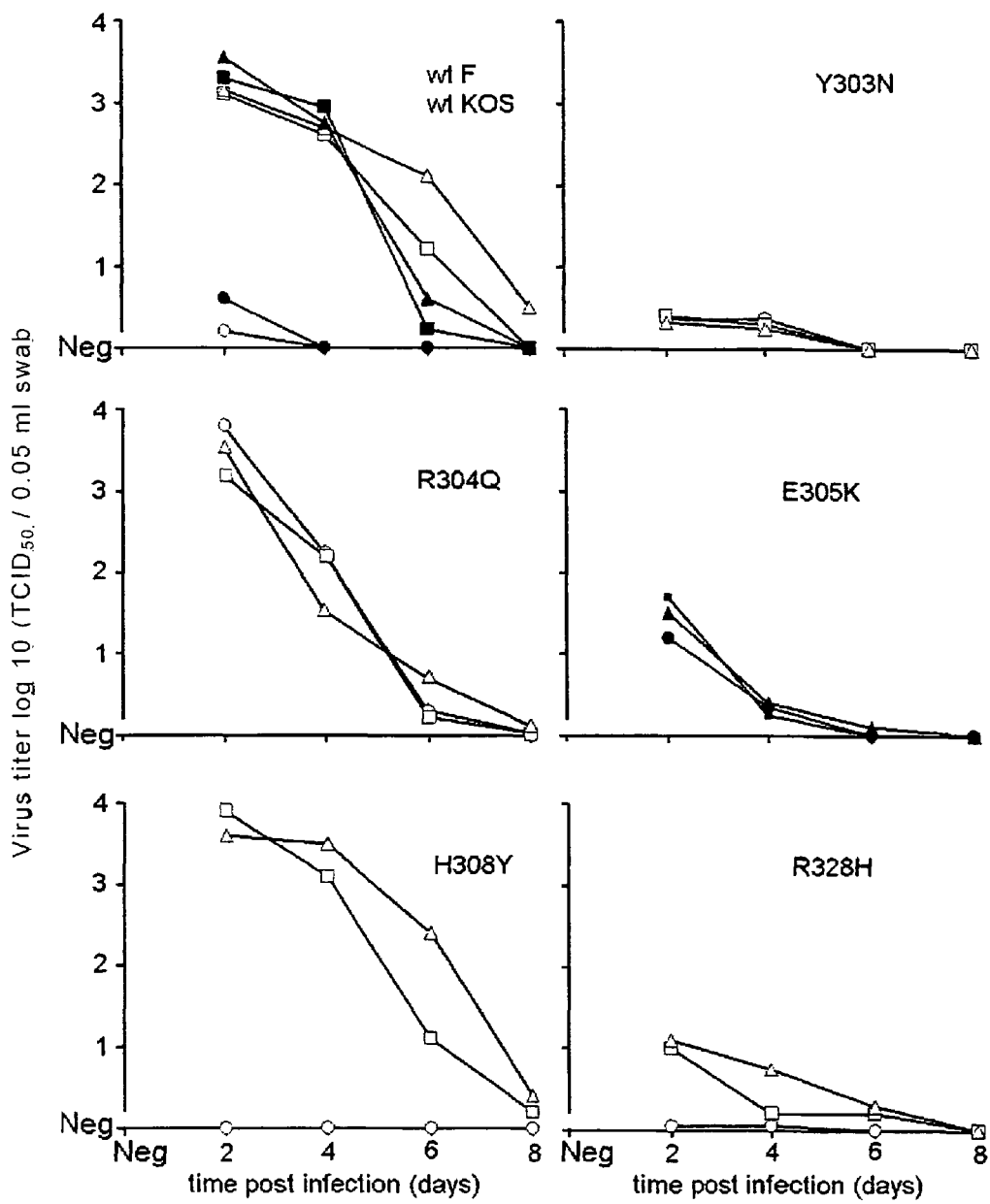
FIG. 25 shows the elimination kinetics of HSV-1 in the genital mucous membranes of C57BL/6 mice receiving passively transferred polyclonal immune serum (open square, filled square), MAb 2c (open circle, filled circle), or precipitated culture medium as control (open triangle, filed triangle) 24 hours before virus inoculation. Data from mice inoculated with wild-type (wt) strain F and its mutant derivatives R126 (Y303N), R1375 (R304Q), R1435 (H308Y), and R233 (R328H) are given by open symbols, data from mice inoculated with wild-type strain KOS 321 and its mutant derivative B4.1 (E305K) are given by closed symbols. Range of S.E. ($log_{10}$) and no. of mice inoculated: wt strain F, open square, ±1.5 to 0, 12 mice; opne circle, ±0.4 to 0, 7 mice; open triangle, ±1.3 to 0, 9 mice; wt strain KOS, filled square, ±1.4 to 0, 8 mice; filed circle, ±0.6 to 0, 8 mice; filed triangle, ±1.4 to 0, 8 mice; F mutant strain R126 (Y303N), open square, ±0.6 to 0, 5 mice; open circle, ±0.6 to 0, 6 mice; opetriangle, ±0.5 to 0, 6 mice; F mutant strain R1375 (R304Q), open square, ±1.2 to 0, 11 mice; open circle, ±1.3 to 0, 10 mice; open triangle, ±1.2 to 0, 11 mice; KOS mutant strain B4.1 (E305K), filled square, ±0.9 to 0, 12 mice; filled circle, ±0.7 to 0, 12 mice; filed triangle, ±0.9 to 0, 10 mice; F mutant strain R1435 (H308Y), open square, ±1.4 to 0.6, 6 mice; open circle, 0, 5 mice; open triangle, ±1.0 to 0.6, 6 mice; F mutant strain R233 (R328H), open square, ±1.0 to 0, 5 mice; open circle, ±0.1 to 0, 5 mice; open triangle, ±1.1 to 0, 6 mice.

To analyse whether the protective effect of MAb 2c in vivo is also dependent on particular amino acids at site B, a total of 168 C57BL/6 mice were inoculated intravaginally with either the mutant viruses or the parental wild-type strains 24 hours after intraperitoneal injection of MAb 2c. For comparison, a polyclonal immune serum adjusted to the same neutralising potency was given. The experiments were carried out as described previously [1, 2]. As shown in FIG. 25, MAb 2c was ineffective in mice inoculated with mutants R126 (Y303N), R1375 (R304Q), and B4.1 (E305K) whilst being effective in mice inoculated with the mutants R1435 (H308Y) or R233 (R328H) or wild-type viruses. Yet the experiments with viral mutants R126, B4.1 and 8233 were slightly hampered by the fact that viral replication of these mutants in the mucous membranes of the mice was inefficient. In particular mutant R126 exhibited a very low replicative capacity. Hence, the course of infection did not differ between R126 infected mice treated with MAb 2c, polyclonal immune serum or the control fluid. Taken together, the results of the mouse protection experiments clearly demonstrated that the gB residues Y303, R304, and E305 are essential for MAb 2c to exhibit its protective effect in vivo.

Characterization of Site A for MAb 2c Binding

The results from the MAb 2c epitope mapping by the peptide scan approach (FIG. 22) initially suggested that binding site A with the common sequence $_{181}$QFMGIFEDR$_{189}$ is a constituent of a discontinuous epitope formed together with site B and potentially other regions which might not be detectable by segmented peptides but part of the functional epitope in the natively folded protein. However, site A was surprisingly not located on the surface of the three-dimensional gB trimer structure [21]. Furthermore, sites A and B are not in close proximity on the gB surface and could not be simultaneously covered by the average area of an antibody paratope.

To investigate the relevance of site A, we started to generate gB constructs and viral mutants with single amino acid exchanges. Yet, efforts to demonstrate the significance of these amino acids in the biological system were unrewarding because substitution of any of these residues in gB constructs and in viral mutants was not followed by the loss of antibody binding, most probably due to presence of the site B motif in the molecule (data and mutagenesis primers not shown).

In order to study the relative importance of each amino acid of peptide 50, $_{178}$RYSQFMGIFEDRAPV$_{192}$ (SEQ ID NO: 43), identified by the peptide scan approach, we carried out a complete substitutional analysis. Therefore, all possible single site substitution analogues (i.e., each position substituted by all other 19 proteinogenic amino acids) were synthesized by SPOT™ synthesis and tested for MAb 2c binding. Most positions of the peptide could be exchanged by several physicochemically different amino acids without loss of binding. The motif $_{186}$FED$_{188}$, however, was conserved, i.e., alteration of these amino acids was associated with loss of antibody binding (data not shown). We therefore hypothesized that site A or predominantly the motif $_{186}$FED$_{188}$ mimics a part of the discontinuous MAb 2c epitope.

To test this assumption, we computationally designed a 12-mer peptide, PFYGYRE-G-FEDF (SEQ ID NO: 52), composed of the residues located in MAb 2c binding site B ($_{299}$PFYGYRE$_{305}$ (SEQ ID NO: 53)) which were found to be biologically important (Table 8), a glycine linker and a C-terminal FEDF motif derived from the most critical sequence of site A. Binding of MAb 2c to this peptide was measured in comparison to the peptide $_{298}$SPFYGYREGSHTEHT$_{312}$ (SEQ ID NO: 48) which exhibited the strongest reactivity in the 15-mer peptide scan (FIG. 22). Both peptides were synthesized on a cellulose membrane and probed with MAb 2c as described in Methods. As shown in FIG. 26, the signal of the combination peptide PFYGYRE-G-FEDF (SEQ ID NO: 52) was by far more intense compared to the site B peptide alone yet the exposure time of the X-ray film was only one fourth of that of the 15-mer peptide scan. This finding strongly supports the assumption that MAb 2c recognises a discontinuous epitope comprised of i) site B from residue 299 to residue 305 (PFYGYRE) (SEQ ID NO: 53), and ii) one or more additional discontinuous regions that can be mimicked by the sequence FEDF (SEQ ID NO: 54).

Discussion

The aim of the current work was to map the binding site for MAb 2c on herpes simplex virus glycoprotein B and to identify key residues of the epitope. With a set of C-terminally truncated versions of recombinantly expressed gB protein, the 487 N-terminal residues were found to be necessary for binding of MAb2c. Additional deletion of 17 or more amino acids from the C-terminus led to a loss of antibody binding, although the synthesis in transiently transfected cells of all deleted versions of gB could readily be ascertained. In order to narrow down the epitope location, two further deletion mutants were constructed, gB(183-488) and gB(436-642), each fused to the signal peptide sequence (amino acids 1-30). As MAb2c failed to bind to any of these latter truncated gB proteins thus contradicting our initial assumption that the epitope of MAb 2c might be localised between residues 470 and 487, we decided to switch to an alternative epitope mapping strategy utilizing synthetic peptides.

Many B-cell epitopes are discontinuous in nature [46]. The mapping of these discontinuous epitopes using fragments of proteins, i.e., peptides, generated either chemically or biologically, suffers from the drawback that peptides derived from single binding regions generally have very low affinities to the binding partner which are usually not measurable in ELISA or surface plasmon resonance assays. Within the last two decades, several examples of investigations into discontinuous epitope mapping studies using peptides synthesized on continuous surfaces have been described [47-50]. In terms of sensitivity, the SPOT™ method is especially suitable [37] due to the high peptide density on the cellulose membranes (approx. 50 nmol/cm$^2$). This leads to avidity and rebinding effects and, therefore, enables the identification of even low affinity peptide-antibody interactions. A comprehensive review covering over 600 citations until 2006 extensively summarizes studies about mapping of linear and discontinuous epitopes using the SPOT™ technology for peptide synthesis [51].

After the localisation of the MAb 2c epitope within the N-terminal 487 gB residues, fine-mapping of the amino acids critical for antibody binding was achieved using the peptide scan approach combined with the SPOT™ synthesis method. As shown in FIG. 20, MAb 2c reacted strongest to the 15-mer peptide $_{298}$SPFYGYREGSHTEHT$_{312}$ (SEQ ID NO: 48), localised in binding site B, leading to the assumption that this sequence is predominantly involved in MAb 2c recognition. Subsequently, the recognition sequence at site B could be refined by higher resolution peptide scanning to the gB amino acids 300 to 308. Final confirmation of the key residues of the epitope was then achieved by a biological approach studying MAb 2c binding to cells transfected with full length gB constructs bearing single point mutations, resulting in the sequence $_{300}$FYGYRE$_{305}$ (SEQ ID NO: 21). In addition the proline residue 299 was found to be important in vivo despite its very limited surface exposure in the three-dimensional gB structure [21]. However, due to the conformational restrictions by the proline side chain—as a result of its cyclic nature proline often stabilises a protein sequence in a fixed structure—this residue is also assumed to be essential for the gB local folding at the antibody binding site. The impact of the key residues identified was corroborated by mouse protection experiments demonstrating that the protective effect of MAb 2c in vivo is abolished when key residues are mutated. Altogether, these data prove that the amino acids 300 to 305 form the essential part of the energetic MAb 2c epitope.

As expected, HSV mutants with single point mutations of the key residues within site B were resistant to MAb 2c binding and neutralisation. Yet, most of the viral mutants were found heavily disabled, exhibiting poor growth in cell culture or mucous membranes. Especially the residue phenylalanine at position 300 appears to be crucial for biological function of gB, since attempts to generate viable virus mutants with an amino acid exchange at that position have been unsuccessful so far. This fact may indicate an important role of this gB motif in the lytic cycle of the virus. Thus, it is intriguing to speculate that the epitope of MAb2c may represent somewhat of an Achilles' heel of gB.

Initial epitope mapping by peptide scanning indicated that MAb 2c recognises an additional gB region, termed site A. Determination of the key residues at that site was performed by substitutional analysis on the peptide $_{178}$RYSQFMGIFEDRAPV$_{192}$ demonstrating that the residues F186, E187, and D188 were highly replacement-sensitive. The relevance of these amino acids in the biological system could not be demonstrated because substitution of these residues in gB constructs and in viral mutants did not affect antibody binding, most probably due to presence of the site B motif in the molecule.

Based on the recently determined crystal structure of the external gB domain [21], the gB monomer was divided into six distinct structural domains. Domain I comprises the amino acids 154 to 363. According to the results presented here, the residues of the most important energetic epitope of MAb 2c (site B) resides in structural domain 1. By superimposing the key residues of site B onto the gB crystal structure it is evident that these residues are situated at the surface of gB within a 22 amino acid loop-like stretch between two β-strands (β13, β14) in the upper third of the structural domain I. The site A residues $_{186}$FED$_{188}$ are also localized in structural domain I but at the base of gB domain 1 in a barely exposed small cavity implying that the two sites are not in spatial proximity. Yet due to structural similarities of gB to other viral glycoproteins and according to results from linker-insertion mutagenesis it is suggested that the crystal structure represents a postfusion form of gB [52-54]. The virion, however, contains the prefusion form of gB and it is suggested that neutralising antibodies should recognise the prefusion conformation of gB [21]. Nonetheless, recent studies have indicated recognition of both pre- and postfusion gB by all gB-specific MAbs tested [55].

An alternative, more attractive explanation, based on the experimental data in combination with the localisation of site A within the three-dimensional gB structure [21] and relative to site B, would be that site A is not a constituent of the discontinuous MAb 2c epitope. The results from the peptide scan and the substitutional analysis suggest the mimicry of one or more regions of the discontinuous epitope which are obviously undetectable by the methodologies applied. The entire functional epitope, i.e., all amino acids being in contact with MAb 2c, in contrast to the energetic epitope mainly residing in the residues 300 to 305 of site B, can only be detected by X-ray or NMR techniques of the antibody-antigen complex [56, 57].

Figure 26:
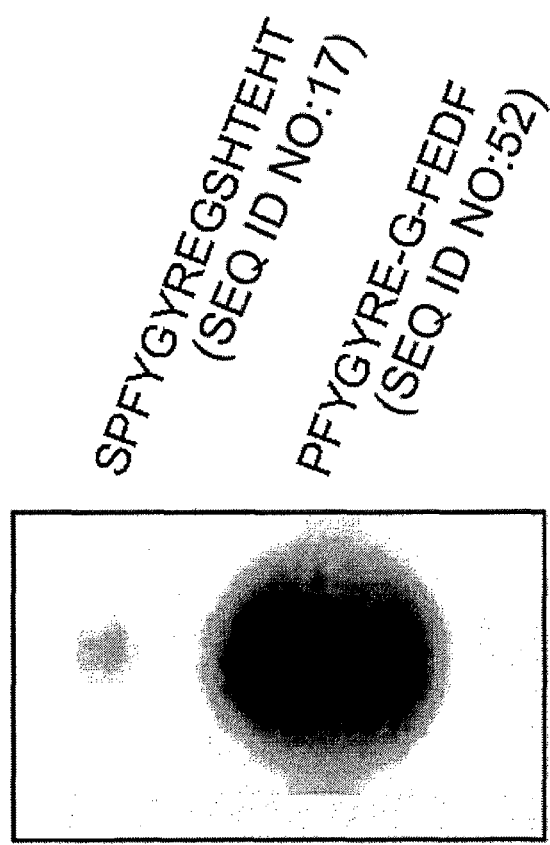
FIG. 26 shows the comparison of the reactivity of MAb 2c to peptide 90 (see FIG. 22, gB sequence $_{298}$SPFYGYREG-SHTEHT$_{312}$; left), and a peptide designed to comprise the critical residues of site B, a glycine linker, and the motif FEDF derived from site A (PFYGYRE-G-FEDF; right).

The hypothesis that site A and especially the FED motif mimics another part of the discontinuous epitope was clearly supported by the attempt to combine the critical residues of site B with the sequence FEDF derived from site A via a glycine residue as a flexible spacer element within one covalently linked molecule (FIG. 26). This engineered peptide resulted in an immense increase in signal intensity when compared to peptide 90 from site B (see FIG. 22) which correlates with an increase in affinity. The mimicry of discontinuous binding sites by peptides covering single binding regions brought together in one synthetic molecule has been described in several publications, e.g., an interleukin-10 mimic for an antibody recognising a discontinuous epitope [49].

Several investigators have used over years monoclonal antibodies to identify functional domains of HSV gB [30, 32, 58-60]. A recent study suggested the existence of at least four functional regions, dispersed on the whole gB structure as defined by the binding pattern of neutralising MAbs to gB [55]. According to these results, the epitope of MAb 2c is located within functional region (FR) 1 which is formed by the structural domain I and the sequence from residue 697 to 725 of structural domain V, the latter extending from residues 670 to 727. Interestingly, three of the most potent neutralising MAbs generated by Bender et al. [55] also have been mapped to structural domain I within FR1 as determined by the reactivity with a gB proteolytic cleavage fragment encomprising residues 98 to 472. MAb 2c, elicited by HSV type 1, is cross-reactive with HSV type 2 [1, 2]. We therefore compared the amino acid sequences of sites A and B of HSV-1 with that of HSV-2 gB. In all 53 full length HSV-2 gBs found in the NCBI protein database (status Jul. 30, 2010), the HSV-1 gB sequences $_{178}$RYSQFMGIFEDRAPV$_{192}$ (SEQ ID NO: 43) and $_{298}$SPFYGYREGSHTEHT$_{312}$ (SEQ ID NO: 48) were present.

Since the main goal of anti-HSV therapy is to rapidly clear viral replication, MAb 2c might provide a potential tool for treating HSV type 1 and 2 infections. In principle, two strategies are pursuable. Firstly, if it could be demonstrated that antibodies of the specificity and the bioactivity of MAb 2c can be induced by peptides derived from site B or the mimicked epitope PFYGYRE-G-FEDF (SEQ ID NO: 52), active immunisation might be conceivable. An alternative approach to exploit the prophylactic and therapeutic potential of MAb 2c would be to convert the mouse antibody into a humanized molecule for passive immunisation, in addition to well established antiviral chemotherapy.

REFERENCES FOR EXAMPLE 4

1. Eis-Hübinger A M, Mohr K, Schneweis K E (1992) Different mechanisms of protection by monoclonal and polyclonal antibodies during the course of herpes simplex virus infection. Intervirology 32:351-360
2. Eis-Hübinger A M, Schmidt D S, Schneweis K E (1993) Anti-glycoprotein B monoclonal antibody protects T cell-depleted mice against herpes simplex virus infection by inhibition of virus replication at the inoculated mucous membranes. J Gen Virol. 74:379-385
3. Whitley R J, Roizman B (2001) Herpes simplex virus infections. Lancet 357:1513-1518
4. Roizman B, Knipe D M, Whitley R J (2007) Herpes simplex viruses. In: Knipe D M, Howley (eds) Fields Virology, 5th edition Lippincott, pp 2501-2601
5. Gupta R, Warren T, Wald A (2007) Genital herpes. Lancet 370:2127-2137

6. Corey L, Wald A (2009) Maternal and neonatal herpes simplex virus infections. N Engl J Med 361:1376-1385
7. Pass R F, Whitley R J, Whelchel J D, Diethelm A G, Reynolds D W, Alford C A (1979) Identification of patients with increased risk of infection with herpes simplex virus after renal transplantation. J Infect Dis 140:487-492
8. Siegal F C, Lopez C, Hammer G S, Brown A E, Kornfeld S J, Gold J, Hassett J, Hirschman S Z, Cunningham-Rundles C, Adelsberg B R, Parham D M, Siegal M, Cunningham-Rundles S, Armstrong D (1981) Severe acquired immunodeficiency in male homosexuals, manifested by chronic perianal ulcerative herpes simplex lesions. N Engl J Med 305:1439-1444
9. Bartlett J G (2004) Recent developments in the management of herpes simplex virus infection in HIV-infected persons. Clin Infect Dis 39 Suppl 5:S237-239
10. Cunningham A L, Diefenbach R J, Miranda-Saksena M, Bosnjak L, Kim M, Jones C, Douglas M W (2006) The cycle of human herpes simplex virus infection: virus transport and immune control. J Infect Dis 194:S11-18
11. Cernik C, Gallina K, Brodell R T (2008) The treatment of herpes simplex infections: an evidence-based review. Arch Intern Med 168:1137-1144
12. Wilson S S, Fakioglu E, Herold B C (2009) Novel approaches in fighting herpes simplex virus infections. Expert Rev Anti Infect Ther 7:559-568
13. Dasgupta G, Chentoufi A A, Nesburn A B, Wechsler S L, BenMohamed L (2009) New concepts in herpes simplex virus vaccine development: notes from the battlefield. Expert Rev Vaccines. 8:1023-1035
14. Pellett P E, Kousoulas K G, Pereira L, Roizman B (1985) Anatomy of the herpes simplex virus 1 strain F glycoprotein B gene: primary sequence and predicted protein structure of the wild type and of monoclonal antibody-resistant mutants. J Virol 53:243-253
15. Pereira L (1994) Function of glycoprotein B homologues of the family herpesviridae. Infect Agents Dis 3:9-28
16. Reske A, Pollara G, Krummenacher C, Chain B M, Katz D R (2007) Understanding HSV-1 entry glycoproteins. Rev Med Virol 17:205-215
17. Bzik D J, Fox B A, DeLuca N A, Person S (1984) Nucleotide sequence of a region of the herpes simplex virus type 1 gB glycoprotein gene: mutations affecting rate of virus entry and cell fusion. Virology 137:185-190
18. Cai W H, Gu B, Person S (1988) Role of glycoprotein B of herpes simplex virus type 1 in viral entry and cell fusion. J Virol 62:2596-2604
19. Butcher M, Raviprakash K, Ghosh H P (1990) Acid pH-induced fusion of cells by herpes simplex virus glycoproteins gB an gD. J Biol Chem 265:5862-5868
20. Bender F C, Whitbeck J C, Ponce de Leon M, Lou H, Eisenberg R J, Cohen G H (2003) Specific association of glycoprotein B with lipid rafts during herpes simplex virus entry. J Virol. 77:9542-9552
21. Heldwein E E, Lou H, Bender F C, Cohen G H, Eisenberg R J, Harrison S C (2006) Crystal structure of glycoprotein B from herpes simplex virus 1. Science 313:217-220
22. Hannah B P, Cairns T M, Bender F C, Whitbeck J C, Lou H, Eisenberg R J, Cohen G H (2009) Herpes simplex virus glycoprotein B associates with target membranes via its fusion loops. J Virol. 83:6825-6836
23. Wright C C, Wisner T W, Hannah B P, Eisenberg R J, Cohen G H, Johnson D C (2009) Fusion between perinuclear virions and the outer nuclear membrane requires the fusogenic activity of herpes simplex virus gB. J Virol 83:11847-11856
24. Atanasiu D, Whitbeck J C, de Leon M P, Lou H, Hannah B P, Cohen G H, Eisenberg R J (2010) Bimolecular complementation defines functional regions of herpes simplex virus gB that are involved with gH/gL as a necessary step leading to cell fusion. J Virol 84:3825-3834
25. Ejercito P M, Kieff E D, Roizman B (1968) Characterization of herpes simplex virus strains differing in their effects on social behaviour of infected cells. J Gen Virol 2:357-364
26. Holland T C, Marlin S D, Levine M, Glorioso J (1983) Antigenic variants of herpes simplex virus selected with glycoprotein-specific monoclonal antibodies. J Virol 45:672-682
27. Kousoulas K G, Pellett P E, Pereira L, Roizman B (1984) Mutations affecting conformation or sequence of neutralizing epitopes identified by reactivity of viable plaques segregate from syn and is domains of HSV-1(F) gB gene. Virology 135:379-394
28. Kousoulas K G, Huo B, Pereira L (1988) Antibody-resistant mutations in cross-reactive and type-specific epitopes of herpes simplex virus 1 glycoprotein B map in separate domains. Virology 166:423-431
29. Highlander S L, Dorney D J, Gage P J, Holland T C, Cai W, Person S, Levine M, Glorioso J C (1989) Identification of mar mutations in herpes simplex virus type 1 glycoprotein B which alter antigenic structure and function in virus penetration. J Virol 63:730-738
30. Pereira L, Ali M, Kousoulas K, Huo B, Banks T (1989) Domain structure of herpes simplex virus 1 glycoprotein B: neutralizing epitopes map in regions of continuous and discontinuous residues. Virology 172:11-24
31. Qadri I, Gimeno C, Navarro D, Pereira L (1991) Mutations in conformation-dependent domains of herpes simplex virus 1 glycoprotein B affect the antigenic properties, dimerization, and transport of the molecule. Virology 180: 135-152
32. Navarro D, Paz P, Pereira L (1992) Domains of herpes simplex virus I glycoprotein B that function in virus penetration, cell-to-cell spread, and cell fusion. Virology 186: 99-112
33. McGeoch D J, Dalrymple M A, Davison A J, Dolan A, Frame M C, McNab D, Perry L J, Scott J E, Taylor P (1988) The complete DNA sequence of the long unique region in the genome of herpes simplex virus type 1. J Gen Virol 69:1531-1574
34. Sambrook J, Fritsch E F, Maniatis T (eds) (1989) Molecular Cloning: A Laboratory Manual. 2nd edition, Cold Spring Harbor Laboratory Press, NY
35. Graham F L, van der Eb A J (1973) A new technique for the assay of infectivity of human adenovirus 5 DNA. Virology 52:456-467
36. Stow N D, Wilkie N M (1976) An improved technique for obtaining enhanced infectivity with herpes simplex virus type 1 DNA. J Gen Virol 33:447-458
37. Frank R (1992) Spot synthesis: an easy technique for the positionally addressable, parallel chemical synthesis on a membrane support. Tetrahedron 48:9217-9232.
38. Kramer A and Schneider-Mergener J (1998) Synthesis and screening of peptide libraries on continuous cellulose membrane supports. Methods Mol Biol 87:25-39
39. Geysen H M, Rodda S J, Mason T J, Tribbick G, Schofs P G (1987) Strategies for epitope analysis using peptide synthesis. J Immunol Methods 102:259-274
40. Reineke U (2009) Antibody epitope mapping using de novo generated synthetic peptide libraries. Methods Mol Biol 524:203-211

41. Pinilla C, Appel J R, Houghten R A (1993) Functional importance of amino acid residues making up peptide antigenic determinants. Mol Immunol 30:577-585
42. Reineke U, Ivascu C, Schlief M, Landgraf C, Gericke S, Zahn G, Herzel H, Volkmer-Engert R, Schneider-Mergener J (2002) Identification of distinct antibody epitopes and mimotopes from a peptide array of 5520 randomly generated sequences. J Immunol Methods 267:37-51
43. Kahlon J, Whitley R J (1988) Antibody response of the newborn after herpes simplex virus infection. J Infect Dis 158:925-933
44. Reed, L J, Muench H. (1938) A simple method of estimating fifty percent endpoints. Am J Hyg 27:493-497
45. Haste Andersen P, Nielsen M, Lund O (2006) Prediction of residues in discontinuous B-cell epitopes using protein 3D structures. Protein Sci 15:2558-2567
46. Van Regenmortel M H V (2009) What is a B-cell epitope? Methods Mol Biol 524 9; 3-20
47. Korth C, Stierli B, Streit P, Moser M, Schaller O, Fischer R, Schulz-Schaeffer W, Kretzschmar H, Raeber A, Braun U, Ehrensperger F, Hornemann S, Glockshuber R, Riek R, Billeter M, Wüthrich K, Oesch B (1997) Prion (PrPSc)-specific epitope defined by a monoclonal antibody. Nature 390:74-77
48. Prodinger W M, Schwendinger M G, Schoch J, Köchle M, Larcher C, Dierich M P (1998) Characterization of C3dg binding to a recess formed between short consensus repeats 1 and 2 of complement receptor type 2 (CR2; CD21). J Immunol 161:4604-4610
49. Reineke U, Sabat R, Misselwitz R, Welfle H, Volk H D, Schneider-Mergener J (1999) A synthetic mimic of a discontinuous binding site on interleukin-10. Nat Biotechnol 3:271-275
50. Bian C, Zhang X, Cai X, Zhang L, Chen Z, Zha Y, Xu Y, Xu K, Lu W, Yan L, Yuan J, Feng J, Hao P, Wang Q, Zhao G, Liu G, Zhu X, Shen H, Zheng B, Shen B, Sun B (2009) Conserved amino acids W423 and N424 in receptor-binding domain of SARS-CoV are potential targets for therapeutic monoclonal antibody. Virology 383:39-46
51. Reineke U, Schneider-Mergener J, Schutkowski M (2006) Peptide arrays in proteomics and drug discovery. In: Ozkan M and Heller M J (eds) BioMEMS and biomedical nanotechnology, volume II, micro/nano technology for genomics and proteomics, Springer, Berlin, pp 161-282
52. Roche S, Bressanelli S. Rey F A, Gaudin (2006) Crystal structure of the low-pH form of the vesicular stomatitis virus glycoprotein G. Science 313:187-191
53. Roche S, Rey F A, Gaudin Y, Bressanelli S (2007) Structure of the prefusion form of the vesicular stomatitis virus glycoprotein G. Science 315: 843-848
54. Lin E, Spear P G (2007) Random linker-insertion mutagenesis to identify functional domains of herpes simplex virus type 1 glycoprotein B. Proc Natl Acad Sci USA 104:13140-13145
55. Bender F C, Samanta M, Heldwein E E, de Leon M P, Bilman E, Lou H, Whitbeck J C, Eisenberg R J, Cohen G H (2007) Antigenic and mutational analyses of herpes simplex virus glycoprotein B reveal four functional regions. J Virol 81:3827-3841
56. Sundberg E J (2009) Structural basis of antibody-antigen interactions. Methods Mol Biol 524:23-36
57. Rosen O, Anglister J (2009) Epitope mapping of antibody-antigen complexes by nuclear magnetic resonance spectroscopy. Methods Mol Biol: 524: 37-57
58. Highlander S L, Cai W H, Person S, Levine M, Glorioso J C (1988) Monoclonal antibodies define a domain on herpes simplex virus glycoprotein B involved in virus penetration. J Virol 62:1881-1888
59. Sanchez-Pescador L, Pereira L, Charlebois E D, Kohl S (1993) Antibodies to epitopes of herpes simplex virus type 1 glycoprotein B (gB) in human sera: analysis of functional gB epitopes defined by inhibition of murine monoclonal antibodies. J Infect Dis 168:844-853
60. Li W, Minova-Foster T J, Norton D D, Muggeridge M I (2006) Identification of functional domains in herpes simplex virus 2 glycoprotein B. J Virol 80:3792-3800

References

DK 187286
JP6135854
U.S. Pat. No. 4,950,595
U.S. Pat. No. 6,180,370
WO 2003/105782
WO 1997/26329

Eis-Hübinger, A. M., K. Mohr, and K. E. Schneweis, *Different mechanisms of protection by monoclonal and polyclonal antibodies during the course of herpes simplex virus infection*. Intervirology, 1991. 32(6): p. 351-360.

Eis-Hübinger, A. M., D. S. Schmidt, and K. E. Schneweis, *Anti-glycoprotein B monoclonal antibody protects T cell-depleted mice against herpes simplex virus infection by inhibition of virus replication at the inoculated mucous membranes*. J. Gen. Virol., 1993. 74 (Pt 3): p. 379-385.

Highlander, S. L., et al., *Monoclonal antibodies define a domain on herpes simplex virus glycoprotein B involved in virus penetration*. J Virol, 1988. 62(6): p. 1881-8.

Queen, C., et al., *A humanized antibody that binds to the interleukin 2 receptor*. Proc Natl Acad Sci USA, 1989. 86(24): p. 10029-33.

Krauss, J., et al., *Specificity grafting of human antibody frameworks selected from a phage display library: generation of a highly stable humanized anti-CD22 single-chain Fv fragment*. Protein Eng, 2003. 16(10): p. 753-9.

Koga, J., S. Chatterjee, and R. J. Whitley, *Studies on herpes simplex virus type I glycoproteins using monoclonal antibodies*. Virology, 1986. 151(2): p. 385-9.

Co, M. S., et al., *Humanized antibodies for antiviral therapy*. Proc Natl Acad Sci USA, 1991. 88(7): p. 2869-73.

Zeitlin, L., et al., *A humanized monoclonal antibody produced in transgenic plants for immunoprotection of the vagina against genital herpes*. Nat Biotechnol, 1998. 16(13): p. 1361-4.

Navarro, D., P. Paz, and L. Pereira, *Domains of herpes simplex virus I glycoprotein B that function in virus penetration, cell-to-cell spread, and cell fusion*. Virology, 1992. 186(1): p. 99-112.

Kabat, E A, Wu T T, Perry H, Gottesman K, Foeller C. *Sequences of Proteins of Immunological Interest* (ed 5). Bethesda: NIH Publication No. 91-3242; 1991.

The invention claimed is:

1. An antibody or fragment thereof, comprising the complementarity determining regions $V_H$CDR1 comprising SEQ ID NO: 1, $V_H$CDR2 comprising SEQ ID NO: 2, $V_H$CDR3 comprising SEQ ID NO: 3, $V_L$CDR1 comprising SEQ ID NO: 4, $V_L$ CDR2comprising SEQ ID NO: 5, and $V_L$CDR3 comprising SEQ ID NO: 6.

2. An antibody which recognises the same epitope as the antibody according to claim 1, wherein said epitope is located at the amino acids 172-195 and 295-313 of glycoprotein B of HSV1 and HSV2.

3. The antibody of claim 2, wherein the antibody is capable of inhibiting the spreading of HSV from an infected cell to an adjacent second non-infected cell (cell-to-cell spread).

4. The antibody of claim 2, wherein the antibody has a dissociation constant $K_D$ of at most 40 nM.

5. The antibody of claim 2, wherein the antibody is in a concentration of at most 20 nM, and is capable of neutralising a defined amount of HSV of 100 $TCID_{50}$.

6. The antibody of claim 2, wherein the antibody comprises an amino acid sequence with at least 70% sequence identity to the amino acid residues shown in positions 1 to 30, 38 to 51, 68 to 99, and 112 to 122 of SEQ ID NO: 9 and in positions 1 to 23, 40 to 54, 62 to 93, and 103 to 113 of SEQ ID NO: 10.

7. The antibody of claim 2, wherein the antibody comprises an amino acid sequence with at least 80% sequence identity to the amino acid residues shown in positions 1 to 30, 38 to 51, 68 to 99, and 112 to 122 of SEQ ID NO: 7 and in positions 1 to 23, 41 to 55, 63 to 94, and 104 to 114 of SEQ ID NO: 8.

8. The antibody of claim 1, wherein the antibody is a bivalent or multivalent antibody.

9. The antibody of claim 1, wherein the antibody is conjugated to an effector moiety, a therapeutic moiety, or a detectable label.

10. A pharmaceutical composition, comprising of an effective amount of the antibody according claim 1 and at least one pharmaceutically acceptable excipient.

11. The antibody of claim 2, wherein the antibody has a dissociation constant $K_D$ of at most 7 nM.

12. The antibody of claim 2, wherein the antibody is in a concentration of at most 16 nM and is capable of neutralising a defined amount of HSV of 100 $TCID_{50}$.

13. The antibody of claim 2, wherein the antibody is in a concentration of at most 12 nM and is capable of neutralising a defined amount of HSV of 100 $TCID_{50}$.

14. The antibody of claim 2, wherein the antibody is in a concentration of at most 10 nM and is capable of neutralising a defined amount of HSV of 100 $TCID_{50}$.

15. The antibody of claim 2, wherein the antibody is in a concentration of at most 8 nM and is capable of neutralising a defined amount of HSV of 100 $TCID_{50}$.

16. The antibody of claim 2, wherein the antibody is in a concentration of at most 4 nM and is capable of neutralising a defined amount of HSV of 100 $TCID_{50}$.

17. The antibody of claim 2, wherein the antibody comprises an amino acid sequence with 100% sequence identity to the amino acid residues shown in positions 1 to 30, 38 to 51, 68 to 99, and 112 to 122 of SEQ ID NO: 7 and in positions 1 to 23, 41 to 55, 63 to 94, and 104 to 114 of SEQ ID NO: 8.

18. The antibody of claim 2, wherein the antibody is a bivalent or multivalent antibody.

19. The antibody of claim 2, wherein the antibody is conjugated to an effector moiety, a therapeutic moiety, or a detectable label.

20. A pharmaceutical composition, comprising of an effective amount of the antibody according to claim 2 and at least one pharmaceutically acceptable excipient.

21. The antibody of claim 1, wherein the antibody is capable of inhibiting the spreading of HSV from an infected cell to an adjacent second non-infected cell (cell-to-cell spread).

22. The antibody of claim 1, wherein the antibody has a dissociation constant $K_D$ of at most 40 nM.

23. The antibody of claim 1, wherein the antibody is in a concentration of at most 20 nM, and is capable of neutralising a defined amount of HSV of 100 $TCID_{50}$.

24. The antibody of claim 1, wherein the antibody comprises an amino acid sequence with at least 70% sequence identity to the amino acid residues shown in positions 1 to 30, 38 to 51, 68 to 99, and 112 to 122 of SEQ ID NO: 9 and in positions 1 to 23, 40 to 54, 62to 93, and 103 to 113 of SEQ ID NO: 10.

25. The antibody of claim 1, wherein the antibody comprises an amino acid sequence with at least 80% sequence identity to the amino acid residues shown in positions 1 to 30, 38 to 51, 68 to 99, and 112 to 122 of SEQ ID NO: 7 and in positions 1 to 23, 41 to 55, 63 to 94, and 104 to 114 of SEQ ID NO: 8.

26. The antibody of claim 1, wherein the antibody comprises an amino acid sequence with 100% sequence identity to the amino acid residues shown in positions 1 to 30, 38 to 51, 68 to 99, and 112 to 122 of SEQ ID NO: 7 and in positions 1 to 23, 41 to 55, 63 to 94, and 104 to 114 of SEQ ID NO: 8.

27. The antibody of claim 1, wherein the antibody has a dissociation constant $K_D$ of at most 7 nM.

28. The antibody of claim 1, wherein the antibody is in a concentration of at most 16 nM and is capable of neutralising a defined amount of HSV of 100 $TCID_{50}$.

29. The antibody of claim 1, wherein the antibody is in a concentration of at most 12 nM and is capable of neutralising a defined amount of HSV of 100 $TCID_{50}$.

30. The antibody of claim 1, wherein the antibody is in a concentration of at most 10 nM and is capable of neutralising a defined amount of HSV of 100 $TCID_{50}$.

31. The antibody of claim 1, wherein the antibody is in a concentration of at most 8 nM and is capable of neutralising a defined amount of HSV of 100 $TCID_{50}$.

32. The antibody of claim 1, wherein the antibody is in a concentration of at most 4 nM and is capable of neutralising a defined amount of HSV of 100 $TCID_{50}$.

* * * * *

SEQUENCE LISTING

<160> NUMBER OF SEQ ID NOS: 105

<210> SEQ ID NO 1

<211> LENGTH: 7
<212> TYPE: PRT
<213> ORGANISM: Artificial Sequence
<220> FEATURE:
<223> OTHER INFORMATION: 2cVH CDR1

<400> SEQUENCE: 1

Thr Ser Gly Met Ser Val Gly
1               5

<210> SEQ ID NO 2
<211> LENGTH: 16
<212> TYPE: PRT
<213> ORGANISM: Artificial Sequence
<220> FEATURE:
<223> OTHER INFORMATION: 2cVH CDR2

<400> SEQUENCE: 2

His Ile Trp Trp Asn Asn Asp Lys Tyr Tyr Lys Pro Ala Leu Lys Ser
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: 2cVH CDR3

<400> SEQUENCE: 3

Ile Tyr Tyr Gly Tyr Arg Pro Tyr Ala Met Asp Tyr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: 2cVL CDR1

<400> SEQUENCE: 4

Arg Ser Ser Gln Ser Ile Val His Ser Asn Gly Asn Thr Tyr Leu Glu
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: 2cVL CDR2

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: 2cVL CDR3

<400> SEQUENCE: 6

Phe Gln Gly Ser His Val Pro Trp Ser
1               5

<210> SEQ ID NO 7
<211> LENGTH: 122

```
<212> TYPE: PRT
<213> ORGANISM: Artificial Sequence
<220> FEATURE:
<223> OTHER INFORMATION: human germline VH framework
<220> FEATURE:
<221> NAME/KEY: misc_feature
<222> LOCATION: (100)..(107)
<223> OTHER INFORMATION: Xaa can be any naturally occurring amino acid

<400> SEQUENCE: 7

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Leu Ala Arg Ile Asp Trp Asp Asp Lys Phe Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Xaa Xaa Xaa Xaa Xaa Xaa Xaa Tyr Phe Asp Tyr Trp
            100                 105                 110

Gly Gln Gly Thr Leu Val Thr Val Ser Ser
        115                 120

<210> SEQ ID NO 8
<211> LENGTH: 114
<212> TYPE: PRT
<213> ORGANISM: Artificial Sequence
<220> FEATURE:
<223> OTHER INFORMATION: human germline VL framework

<400> SEQUENCE: 8

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Glu Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Trp Thr Phe Gly Gln Gly Thr Lys Val Glu Ile
            100                 105                 110

Lys Arg

<210> SEQ ID NO 9
<211> LENGTH: 122
<212> TYPE: PRT
<213> ORGANISM: Artificial Sequence
<220> FEATURE:
<223> OTHER INFORMATION: VH of 2c antibody

<400> SEQUENCE: 9

Gln Val Thr Leu Lys Glu Ser Gly Pro Gly Ile Leu Leu Pro Ser Gln
```

```
1               5                   10                  15
Thr Leu Ser Leu Thr Cys Ser Phe Ser Gly Phe Ser Leu Ser Thr Ser
            20                  25                  30

Gly Met Ser Val Gly Trp Ile Arg Gln Pro Ser Gly Lys Gly Leu Glu
        35                  40                  45

Trp Leu Gly His Ile Trp Trp Asn Asn Asp Lys Tyr Tyr Lys Pro Ala
    50                  55                  60

Leu Lys Ser Arg Leu Thr Ile Ser Lys Asp Thr Ser Asn Lys Gln Val
65                  70                  75                  80

Phe Leu Lys Ile Ala Ser Val Val Thr Ala Asp Thr Ala Thr Tyr Tyr
                85                  90                  95

Cys Ala Arg Ile Tyr Tyr Gly Tyr Arg Pro Tyr Ala Met Asp Tyr Trp
                100                 105                 110

Gly Gln Gly Thr Ser Val Thr Val Ser Ser
            115                 120

<210> SEQ ID NO 10
<211> LENGTH: 113
<212> TYPE: PRT
<213> ORGANISM: Artificial Sequence
<220> FEATURE:
<223> OTHER INFORMATION: VL of 2c antibody

<400> SEQUENCE: 10

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Ser Phe Gly Gly Gly Thr Lys Leu Glu Ile Lys
                100                 105                 110

Arg

<210> SEQ ID NO 11
<211> LENGTH: 903
<212> TYPE: PRT
<213> ORGANISM: HSV1 strain F

<400> SEQUENCE: 11

Met Arg Gln Gly Ala Ala Arg Gly Cys Arg Trp Phe Val Val Trp Ala
1               5                   10                  15

Leu Leu Gly Leu Thr Leu Gly Val Leu Val Ala Ser Ala Ala Pro Ser
            20                  25                  30

Ser Pro Gly Thr Pro Gly Val Ala Ala Ala Thr Gln Ala Ala Asn Gly
        35                  40                  45

Gly Pro Ala Thr Pro Ala Pro Pro Ala Pro Gly Pro Ala Pro Thr Gly
    50                  55                  60

Asp Thr Lys Pro Lys Lys Asn Lys Lys Pro Lys Asn Pro Pro Pro Pro
65                  70                  75                  80
```

```
Arg Pro Ala Gly Asp Asn Ala Thr Val Ala Gly His Ala Thr Leu
                85                  90                  95

Arg Glu His Leu Arg Asp Ile Lys Ala Glu Asn Thr Asp Ala Asn Phe
            100                 105                 110

Tyr Val Cys Pro Pro Thr Gly Ala Thr Val Gln Phe Glu Gln
        115                 120                 125

Pro Arg Arg Cys Pro Thr Arg Pro Glu Gly Gln Asn Tyr Thr Glu Gly
            130                 135                 140

Ile Ala Val Val Phe Lys Glu Asn Ile Ala Pro Tyr Lys Phe Lys Ala
145                 150                 155                 160

Thr Met Tyr Tyr Lys Asp Val Thr Val Ser Gln Val Trp Phe Gly His
                165                 170                 175

Arg Tyr Ser Gln Phe Met Gly Ile Phe Glu Asp Arg Ala Pro Val Pro
            180                 185                 190

Phe Glu Glu Val Ile Asp Lys Ile Asn Ala Lys Gly Val Cys Arg Ser
            195                 200                 205

Thr Ala Lys Tyr Val Arg Asn Asn Leu Glu Thr Thr Ala Phe His Arg
        210                 215                 220

Asp Asp His Glu Thr Asp Met Glu Leu Lys Pro Ala Asn Ala Ala Thr
225                 230                 235                 240

Arg Thr Ser Arg Gly Trp His Thr Thr Asp Leu Lys Tyr Asn Pro Ser
                245                 250                 255

Arg Val Glu Ala Phe His Arg Tyr Gly Thr Thr Val Asn Cys Ile Val
            260                 265                 270

Glu Glu Val Asp Ala Arg Ser Val Tyr Pro Tyr Asp Glu Phe Val Leu
        275                 280                 285

Ala Thr Gly Asp Phe Val Tyr Met Ser Pro Phe Tyr Gly Tyr Arg Glu
    290                 295                 300

Gly Ser His Thr Glu His Thr Ser Tyr Ala Ala Asp Arg Phe Lys Gln
305                 310                 315                 320

Val Asp Gly Phe Tyr Ala Arg Asp Leu Thr Thr Lys Ala Arg Ala Thr
                325                 330                 335

Ala Pro Thr Thr Arg Asn Leu Leu Thr Thr Pro Lys Phe Thr Val Ala
            340                 345                 350

Trp Asp Trp Val Pro Lys Arg Pro Ser Val Cys Thr Met Thr Lys Trp
        355                 360                 365

Gln Glu Val Asp Glu Met Leu Arg Ser Glu Tyr Gly Gly Ser Phe Arg
    370                 375                 380

Phe Ser Ser Asp Ala Ile Ser Thr Thr Phe Thr Thr Asn Leu Thr Glu
385                 390                 395                 400

Tyr Pro Leu Ser Arg Val Asp Leu Gly Asp Cys Ile Gly Lys Asp Ala
                405                 410                 415

Arg Asp Ala Met Asp Arg Ile Phe Ala Arg Arg Tyr Asn Ala Thr His
            420                 425                 430

Ile Lys Val Gly Gln Pro Gln Tyr Tyr Leu Ala Asn Gly Gly Phe Leu
        435                 440                 445

Ile Ala Tyr Gln Pro Leu Leu Ser Asn Thr Leu Ala Glu Leu Tyr Val
    450                 455                 460

Arg Glu His Leu Arg Glu Gln Ser Arg Lys Pro Asn Pro Thr Pro
465                 470                 475                 480

Pro Pro Pro Gly Ala Ser Ala Asn Ala Ser Val Glu Arg Ile Lys Thr
                485                 490                 495

Thr Ser Ser Ile Glu Phe Ala Arg Leu Gln Phe Thr Tyr Asn His Ile
```

```
                500             505                 510
    Gln Arg His Val Asn Asp Met Leu Gly Arg Val Ala Ile Ala Trp Cys
                    515                 520                 525
    Glu Leu Gln Asn His Glu Leu Thr Leu Trp Asn Glu Ala Arg Lys Leu
                    530                 535                 540
    Asn Pro Asn Ala Ile Ala Ser Ala Thr Val Gly Arg Arg Val Ser Ala
    545                 550                 555                 560
    Arg Met Leu Gly Asp Val Met Ala Val Ser Thr Cys Val Pro Val Ala
                        565                 570                 575
    Ala Asp Asn Val Ile Val Gln Asn Ser Met Arg Ile Ser Ser Arg Pro
                    580                 585                 590
    Gly Ala Cys Tyr Ser Arg Pro Leu Val Ser Phe Arg Tyr Glu Asp Gln
                    595                 600                 605
    Gly Pro Leu Val Glu Gly Gln Leu Gly Glu Asn Asn Glu Leu Arg Leu
                    610                 615                 620
    Thr Arg Asp Ala Ile Glu Pro Cys Thr Val Gly His Arg Arg Tyr Phe
    625                 630                 635                 640
    Thr Phe Gly Gly Gly Tyr Val Tyr Phe Glu Glu Tyr Ala Tyr Ser His
                        645                 650                 655
    Gln Leu Ser Arg Ala Asp Ile Thr Thr Val Ser Thr Phe Ile Asp Leu
                        660                 665                 670
    Asn Ile Thr Met Leu Glu Asp His Glu Phe Val Pro Leu Glu Val Tyr
                    675                 680                 685
    Thr Arg His Glu Ile Lys Asp Ser Gly Leu Leu Asp Tyr Thr Glu Val
                    690                 695                 700
    Gln Arg Arg Asn Gln Leu His Asp Leu Arg Phe Ala Asp Ile Asp Thr
    705                 710                 715                 720
    Val Ile His Ala Asp Ala Asn Ala Ala Met Phe Ala Gly Leu Gly Ala
                        725                 730                 735
    Phe Phe Glu Gly Met Gly Asp Leu Gly Arg Ala Val Gly Lys Val Val
                    740                 745                 750
    Met Gly Ile Val Gly Gly Val Val Ser Ala Val Ser Gly Val Ser Ser
                        755                 760                 765
    Phe Met Ser Asn Pro Phe Gly Ala Leu Ala Val Gly Leu Leu Val Leu
                    770                 775                 780
    Ala Gly Leu Ala Ala Ala Phe Phe Ala Phe Arg Tyr Val Met Arg Leu
    785                 790                 795                 800
    Gln Ser Asn Pro Met Lys Ala Leu Tyr Pro Leu Thr Thr Lys Glu Leu
                        805                 810                 815
    Lys Asn Pro Thr Asn Pro Asp Ala Ser Gly Glu Gly Glu Glu Gly Gly
                    820                 825                 830
    Asp Phe Asp Glu Ala Lys Leu Ala Glu Ala Arg Glu Met Ile Arg Tyr
                    835                 840                 845
    Met Ala Leu Val Ser Ala Met Glu Arg Thr Glu His Lys Ala Lys Lys
                    850                 855                 860
    Lys Gly Thr Ser Ala Leu Leu Ser Ala Lys Val Thr Asp Met Val Met
    865                 870                 875                 880
    Arg Lys Arg Arg Asn Thr Asn Tyr Thr Gln Val Pro Asn Lys Asp Gly
                        885                 890                 895
    Asp Ala Asp Glu Asp Leu
                    900

<210> SEQ ID NO 12
```

```
<211> LENGTH: 904
<212> TYPE: PRT
<213> ORGANISM: HSV1 strain KOS

<400> SEQUENCE: 12
```

Met His Gln Gly Ala Pro Ser Trp Gly Arg Arg Trp Phe Val Val Trp
1               5                   10                  15

Ala Leu Leu Gly Leu Thr Leu Gly Val Leu Ala Ser Ala Ala Pro
            20                  25                  30

Thr Ser Pro Gly Thr Pro Gly Val Ala Ala Thr Gln Ala Ala Asn
        35                  40                  45

Gly Gly Pro Ala Thr Pro Ala Pro Pro Leu Gly Ala Ala Pro Thr
    50                  55                  60

Gly Asp Pro Lys Pro Lys Lys Asn Lys Lys Pro Lys Asn Pro Thr Pro
65                  70                  75                  80

Pro Arg Pro Ala Gly Asp Asn Ala Thr Val Ala Ala Gly His Ala Thr
                85                  90                  95

Leu Arg Glu His Leu Arg Asp Ile Lys Ala Glu Asn Thr Asp Ala Asn
            100                 105                 110

Phe Tyr Val Cys Pro Pro Thr Gly Ala Thr Val Val Gln Phe Glu
        115                 120                 125

Gln Pro Arg Arg Cys Pro Thr Arg Pro Glu Gly Gln Asn Tyr Thr Glu
    130                 135                 140

Gly Ile Ala Val Val Phe Lys Glu Asn Ile Ala Pro Tyr Lys Phe Lys
145                 150                 155                 160

Ala Thr Met Tyr Tyr Lys Asp Val Thr Val Ser Gln Val Trp Phe Gly
                165                 170                 175

His Arg Tyr Ser Gln Phe Met Gly Ile Phe Glu Asp Arg Ala Pro Val
            180                 185                 190

Pro Phe Glu Glu Val Ile Asp Lys Ile Asn Ala Lys Gly Val Cys Arg
        195                 200                 205

Ser Thr Ala Lys Tyr Val Arg Asn Asn Leu Glu Thr Thr Ala Phe His
    210                 215                 220

Arg Asp Asp His Glu Thr Asp Met Glu Leu Lys Pro Ala Asn Ala Ala
225                 230                 235                 240

Thr Arg Thr Ser Arg Gly Trp His Thr Thr Asp Leu Lys Tyr Asn Pro
                245                 250                 255

Ser Arg Val Glu Ala Phe His Arg Tyr Gly Thr Thr Val Asn Cys Ile
            260                 265                 270

Val Glu Glu Val Asp Ala Arg Ser Val Tyr Pro Tyr Asp Glu Phe Val
        275                 280                 285

Leu Ala Thr Gly Asp Phe Val Tyr Met Ser Pro Phe Tyr Gly Tyr Arg
    290                 295                 300

Glu Gly Ser His Thr Glu His Thr Thr Tyr Ala Ala Asp Arg Phe Lys
305                 310                 315                 320

Gln Val Asp Gly Phe Tyr Ala Arg Asp Leu Thr Thr Lys Ala Arg Ala
                325                 330                 335

Thr Ala Pro Thr Thr Arg Asn Leu Leu Thr Thr Pro Lys Phe Thr Val
            340                 345                 350

Ala Trp Asp Trp Val Pro Lys Arg Pro Ser Val Cys Thr Met Thr Lys
        355                 360                 365

Trp Gln Glu Val Asp Glu Met Leu Arg Ser Glu Tyr Gly Gly Ser Phe
    370                 375                 380

Arg Phe Ser Ser Asp Ala Ile Ser Thr Thr Phe Thr Thr Asn Leu Thr

```
385                 390                 395                 400
Glu Tyr Pro Leu Ser Arg Val Asp Leu Gly Asp Cys Ile Gly Lys Asp
                405                 410                 415

Ala Arg Asp Ala Met Asp Arg Ile Phe Ala Arg Arg Tyr Asn Ala Thr
            420                 425                 430

His Ile Lys Val Gly Gln Pro Gln Tyr Tyr Gln Ala Asn Gly Gly Phe
            435                 440                 445

Leu Ile Ala Tyr Gln Pro Leu Leu Ser Asn Thr Leu Ala Glu Leu Tyr
        450                 455                 460

Val Arg Glu His Leu Arg Glu Gln Ser Arg Lys Pro Pro Asn Pro Thr
465                 470                 475                 480

Pro Pro Pro Gly Ala Ser Ala Asn Ala Ser Val Glu Arg Ile Lys
                485                 490                 495

Thr Thr Ser Ser Ile Glu Phe Ala Arg Leu Gln Phe Thr Tyr Asn His
                500                 505                 510

Ile Gln Arg His Val Asn Asp Met Leu Gly Arg Val Ala Ile Ala Trp
            515                 520                 525

Cys Glu Leu Gln Asn His Glu Leu Thr Leu Trp Asn Glu Ala Arg Lys
        530                 535                 540

Leu Asn Pro Asn Ala Ile Ala Ser Val Thr Val Gly Arg Arg Val Ser
545                 550                 555                 560

Ala Arg Met Leu Gly Asp Val Met Ala Val Ser Thr Cys Val Pro Val
                565                 570                 575

Ala Ala Asp Asn Val Ile Val Gln Asn Ser Met Arg Ile Ser Ser Arg
                580                 585                 590

Pro Gly Ala Cys Tyr Ser Arg Pro Leu Val Ser Phe Arg Tyr Glu Asp
            595                 600                 605

Gln Gly Pro Leu Val Glu Gly Gln Leu Gly Glu Asn Asn Glu Leu Arg
        610                 615                 620

Leu Thr Arg Asp Ala Ile Glu Pro Cys Thr Val Gly His Arg Arg Tyr
625                 630                 635                 640

Phe Thr Phe Gly Gly Gly Tyr Val Tyr Phe Glu Glu Tyr Ala Tyr Ser
                645                 650                 655

His Gln Leu Ser Arg Ala Asp Ile Thr Thr Val Ser Thr Phe Ile Asp
            660                 665                 670

Leu Asn Ile Thr Met Leu Glu Asp His Glu Phe Val Pro Leu Glu Val
        675                 680                 685

Tyr Thr Arg His Glu Ile Lys Asp Ser Gly Leu Leu Asp Tyr Thr Glu
        690                 695                 700

Val Gln Arg Arg Asn Gln Leu His Asp Leu Arg Phe Ala Asp Ile Asp
705                 710                 715                 720

Thr Val Ile His Ala Asp Ala Asn Ala Ala Met Phe Ala Gly Leu Gly
                725                 730                 735

Ala Phe Phe Glu Gly Met Gly Asp Leu Gly Arg Ala Val Gly Lys Val
            740                 745                 750

Val Met Gly Ile Val Gly Gly Val Ser Ala Val Ser Gly Val Ser
            755                 760                 765

Ser Phe Met Ser Asn Pro Phe Gly Ala Leu Ala Val Gly Leu Leu Val
        770                 775                 780

Leu Ala Gly Leu Ala Ala Ala Phe Phe Ala Phe Arg Tyr Val Met Arg
785                 790                 795                 800

Leu Gln Ser Asn Pro Met Lys Ala Leu Tyr Pro Leu Thr Thr Lys Glu
                805                 810                 815
```

-continued

```
Leu Lys Asn Pro Thr Asn Pro Asp Ala Ser Gly Glu Gly Glu Gly
            820                 825                 830

Gly Asp Phe Asp Glu Ala Lys Leu Ala Glu Ala Arg Glu Met Ile Arg
        835                 840                 845

Tyr Met Ala Leu Val Ser Ala Met Glu Arg Thr Glu His Lys Ala Lys
    850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
                885                 890                 895

Gly Asp Ala Asp Glu Asp Leu
                900

<210> SEQ ID NO 13
<211> LENGTH: 904
<212> TYPE: PRT
<213> ORGANISM: HSV1 strain gC-39-R6

<400> SEQUENCE: 13

Met His Gln Gly Ala Pro Ser Trp Gly Arg Arg Trp Phe Val Val Trp
1               5                   10                  15

Ala Leu Leu Gly Leu Thr Leu Gly Val Leu Val Ala Ser Ala Ala Pro
            20                  25                  30

Ser Ser Pro Gly Thr Pro Gly Val Ala Ala Thr Gln Ala Ala Asn
        35                  40                  45

Gly Gly Pro Ala Thr Pro Ala Pro Pro Ala Leu Gly Ala Ala Pro Thr
50                  55                  60

Gly Asp Pro Lys Pro Lys Lys Asn Lys Lys Pro Lys Asn Pro Thr Pro
65                  70                  75                  80

Pro Arg Pro Ala Gly Asp Asn Ala Thr Val Ala Ala Gly His Ala Thr
                85                  90                  95

Leu Arg Glu His Leu Arg Asp Ile Lys Ala Glu Asn Thr Asp Ala Asn
            100                 105                 110

Phe Tyr Val Cys Pro Pro Pro Thr Gly Ala Thr Val Val Gln Phe Glu
        115                 120                 125

Gln Pro Arg Arg Cys Pro Thr Arg Pro Glu Gly Gln Asn Tyr Thr Glu
    130                 135                 140

Gly Ile Ala Val Val Phe Lys Glu Asn Ile Ala Pro Tyr Lys Phe Lys
145                 150                 155                 160

Ala Thr Met Tyr Tyr Lys Asp Val Thr Val Ser Gln Val Trp Phe Gly
                165                 170                 175

His Arg Tyr Ser Gln Phe Met Gly Ile Phe Glu Asp Arg Ala Pro Val
            180                 185                 190

Pro Phe Glu Glu Val Ile Asp Lys Ile Asn Ala Lys Gly Val Cys Arg
        195                 200                 205

Ser Thr Ala Lys Tyr Val Arg Asn Asn Leu Glu Thr Thr Ala Phe His
    210                 215                 220

Arg Asp Asp His Glu Thr Asp Met Glu Leu Lys Pro Ala Asn Ala Ala
225                 230                 235                 240

Thr Arg Thr Ser Arg Gly Trp His Thr Thr Asp Leu Lys Tyr Asn Pro
                245                 250                 255

Ser Arg Val Glu Ala Phe His Arg Tyr Gly Thr Thr Val Asn Cys Ile
            260                 265                 270

Val Glu Glu Val Asp Ala Arg Ser Val Tyr Pro Tyr Asp Glu Phe Val
```

-continued

```
            275                 280                 285
Leu Ala Thr Gly Asp Phe Val Tyr Met Ser Pro Phe Tyr Gly Tyr Arg
            290                 295                 300
Glu Gly Ser His Thr Glu His Thr Ser Tyr Ala Ala Asp Arg Phe Lys
305                 310                 315                 320
Gln Val Asp Gly Phe Tyr Ala Arg Asp Leu Thr Thr Lys Ala Arg Ala
                325                 330                 335
Thr Ala Pro Thr Thr Arg Asn Leu Leu Thr Thr Pro Lys Phe Thr Val
                340                 345                 350
Ala Trp Asp Trp Val Pro Lys Arg Pro Ser Val Cys Thr Met Thr Lys
                355                 360                 365
Trp Gln Glu Val Asp Glu Met Leu Arg Ser Glu Tyr Gly Gly Ser Phe
370                 375                 380
Arg Phe Ser Ser Asp Ala Ile Ser Thr Thr Phe Thr Thr Asn Leu Thr
385                 390                 395                 400
Glu Tyr Pro Leu Ser Arg Val Asp Leu Gly Asp Cys Ile Gly Lys Asp
                405                 410                 415
Ala Arg Asp Ala Met Asp Arg Ile Phe Ala Arg Arg Tyr Asn Ala Thr
                420                 425                 430
His Ile Lys Val Gly Gln Pro Gln Tyr Tyr Leu Ala Asn Gly Gly Phe
                435                 440                 445
Leu Ile Ala Tyr Gln Pro Leu Leu Ser Asn Thr Leu Ala Glu Leu Tyr
            450                 455                 460
Val Arg Glu His Leu Arg Glu Gln Ser Arg Lys Pro Pro Asn Pro Thr
465                 470                 475                 480
Pro Pro Pro Gly Ala Ser Ala Asn Ala Ser Val Glu Arg Ile Lys
                485                 490                 495
Thr Thr Ser Ser Ile Glu Phe Ala Arg Leu Gln Phe Thr Tyr Asn His
                500                 505                 510
Ile Gln His His Val Asn Asp Met Leu Gly Arg Val Ala Ile Ala Trp
            515                 520                 525
Cys Glu Leu Gln Asn His Glu Leu Thr Leu Trp Asn Glu Ala Arg Lys
            530                 535                 540
Leu Asn Pro Asn Ala Ile Ala Ser Val Thr Val Gly Arg Arg Val Ser
545                 550                 555                 560
Ala Arg Met Leu Gly Asp Val Met Ala Val Ser Thr Cys Val Pro Val
                565                 570                 575
Ala Ala Asp Asn Val Ile Val Gln Asn Ser Met Arg Ile Ser Ser Arg
                580                 585                 590
Pro Gly Ala Cys Tyr Ser Arg Pro Leu Val Ser Phe Arg Tyr Glu Asp
                595                 600                 605
Gln Gly Pro Leu Val Glu Gly Gln Leu Gly Glu Asn Asn Glu Leu Arg
            610                 615                 620
Leu Thr Arg Asp Ala Ile Glu Pro Cys Thr Val Gly His Arg Arg Tyr
625                 630                 635                 640
Phe Thr Phe Gly Gly Gly Tyr Val Tyr Phe Glu Glu Tyr Ala Tyr Ser
                645                 650                 655
His Gln Leu Ser Arg Ala Asp Ile Thr Thr Val Ser Thr Phe Ile Asp
                660                 665                 670
Leu Asn Ile Thr Met Leu Glu Asp His Glu Phe Val Pro Leu Glu Val
            675                 680                 685
Tyr Thr Arg His Glu Ile Lys Asp Ser Gly Leu Leu Asp Tyr Thr Glu
            690                 695                 700
```

```
Val Gln Arg Arg Asn Gln Leu His Asp Leu Arg Phe Ala Asp Ile Asp
705                 710                 715                 720

Thr Val Ile His Ala Asp Ala Asn Ala Ala Met Phe Ala Gly Leu Gly
                725                 730                 735

Ala Phe Phe Glu Gly Met Gly Asp Leu Gly Arg Ala Val Gly Lys Val
            740                 745                 750

Val Met Gly Ile Val Gly Gly Val Ser Ala Val Ser Gly Val Ser
        755                 760                 765

Ser Phe Met Ser Asn Pro Phe Gly Ala Leu Ala Val Gly Leu Leu Val
    770                 775                 780

Leu Ala Gly Leu Ala Ala Ala Phe Phe Ala Phe Arg Tyr Val Met Arg
785                 790                 795                 800

Leu Gln Ser Asn Pro Met Lys Ala Leu Tyr Pro Leu Thr Thr Lys Glu
                805                 810                 815

Leu Lys Asn Pro Thr Asn Pro Asp Ala Ser Gly Glu Gly Glu Glu Gly
            820                 825                 830

Gly Asp Phe Asp Glu Ala Lys Leu Ala Glu Ala Arg Glu Met Ile Arg
        835                 840                 845

Tyr Met Ala Leu Val Ser Ala Met Glu Arg Thr Glu His Lys Ala Lys
850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
                885                 890                 895

Gly Asp Ala Asp Glu Asp Leu
            900

<210> SEQ ID NO 14
<211> LENGTH: 904
<212> TYPE: PRT
<213> ORGANISM: HSV2 strain HG52

<400> SEQUENCE: 14

Met Arg Gly Gly Gly Leu Ile Cys Ala Leu Val Val Gly Ala Leu Val
1               5                   10                  15

Ala Ala Val Ala Ser Ala Ala Pro Ala Ala Pro Ala Ala Pro Arg Ala
                20                  25                  30

Ser Gly Gly Val Ala Ala Thr Val Ala Ala Asn Gly Gly Pro Ala Ser
            35                  40                  45

Arg Pro Pro Val Pro Ser Pro Ala Thr Thr Lys Ala Arg Lys Arg
50                  55                  60

Lys Thr Lys Lys Pro Pro Lys Arg Pro Glu Ala Thr Pro Pro Asp
65                  70                  75                  80

Ala Asn Ala Thr Val Ala Ala Gly His Ala Thr Leu Arg Ala His Leu
                85                  90                  95

Arg Glu Ile Lys Val Glu Asn Ala Asp Ala Gln Phe Tyr Val Cys Pro
            100                 105                 110

Pro Pro Thr Gly Ala Thr Val Val Gln Phe Glu Gln Pro Arg Arg Cys
        115                 120                 125

Pro Thr Arg Pro Glu Gly Gln Asn Tyr Thr Glu Gly Ile Ala Val Val
    130                 135                 140

Phe Lys Glu Asn Ile Ala Pro Tyr Lys Phe Lys Ala Thr Met Tyr Tyr
145                 150                 155                 160

Lys Asp Val Thr Val Ser Gln Val Trp Phe Gly His Arg Tyr Ser Gln
```

```
                    165                 170                 175
Phe Met Gly Ile Phe Glu Asp Arg Ala Pro Val Pro Phe Glu Glu Val
                180                 185                 190
Ile Asp Lys Ile Asn Thr Lys Gly Val Cys Arg Ser Thr Ala Lys Tyr
            195                 200                 205
Val Arg Asn Asn Met Glu Thr Thr Ala Phe His Arg Asp Asp His Glu
        210                 215                 220
Thr Asp Met Glu Leu Lys Pro Ala Lys Val Ala Thr Arg Thr Ser Arg
225                 230                 235                 240
Gly Trp His Thr Thr Asp Leu Lys Tyr Asn Pro Ser Arg Val Glu Ala
                245                 250                 255
Phe His Arg Tyr Gly Thr Val Asn Cys Ile Val Glu Glu Val Asp
            260                 265                 270
Ala Arg Ser Val Tyr Pro Tyr Asp Glu Phe Val Leu Ala Thr Gly Asp
        275                 280                 285
Phe Val Tyr Met Ser Pro Phe Tyr Gly Tyr Arg Glu Gly Ser His Thr
    290                 295                 300
Glu His Thr Ser Tyr Ala Ala Asp Arg Phe Lys Gln Val Asp Gly Phe
305                 310                 315                 320
Tyr Ala Arg Asp Leu Thr Thr Lys Ala Arg Ala Thr Ser Pro Thr Thr
                325                 330                 335
Arg Asn Leu Leu Thr Thr Pro Lys Phe Thr Val Ala Trp Asp Trp Val
            340                 345                 350
Pro Lys Arg Pro Ala Val Cys Thr Met Thr Lys Trp Gln Glu Val Asp
        355                 360                 365
Glu Met Leu Arg Ala Glu Tyr Gly Gly Ser Phe Arg Phe Ser Ser Asp
    370                 375                 380
Ala Ile Ser Thr Thr Phe Thr Thr Asn Leu Thr Glu Tyr Ser Leu Ser
385                 390                 395                 400
Arg Val Asp Leu Gly Asp Cys Ile Gly Arg Asp Ala Arg Glu Ala Ile
                405                 410                 415
Asp Arg Met Phe Ala Arg Lys Tyr Asn Ala Thr His Ile Lys Val Gly
            420                 425                 430
Gln Pro Gln Tyr Tyr Leu Ala Thr Gly Gly Phe Leu Ile Ala Tyr Gln
        435                 440                 445
Pro Leu Leu Ser Asn Thr Leu Ala Glu Leu Tyr Val Arg Glu Tyr Met
    450                 455                 460
Arg Glu Gln Asp Arg Lys Pro Arg Asn Ala Thr Pro Ala Pro Leu Arg
465                 470                 475                 480
Glu Ala Pro Ser Ala Asn Ala Ser Val Glu Arg Ile Lys Thr Thr Ser
                485                 490                 495
Ser Ile Glu Phe Ala Arg Leu Gln Phe Thr Tyr Asn His Ile Gln Arg
            500                 505                 510
His Val Asn Asp Met Leu Gly Arg Ile Ala Val Ala Trp Cys Glu Leu
        515                 520                 525
Gln Asn His Glu Leu Thr Leu Trp Asn Glu Ala Arg Lys Leu Asn Pro
    530                 535                 540
Asn Ala Ile Ala Ser Ala Thr Val Gly Arg Arg Val Ser Ala Arg Met
545                 550                 555                 560
Leu Gly Asp Val Met Ala Val Ser Thr Cys Val Pro Val Ala Pro Asp
                565                 570                 575
Asn Val Ile Val Gln Asn Ser Met Arg Val Ser Ser Arg Pro Gly Thr
            580                 585                 590
```

```
Cys Tyr Ser Arg Pro Leu Val Ser Phe Arg Tyr Glu Asp Gln Gly Pro
            595                 600                 605

Leu Ile Glu Gly Gln Leu Gly Glu Asn Asn Glu Leu Arg Leu Thr Arg
    610                 615                 620

Asp Ala Leu Glu Pro Cys Thr Val Gly His Arg Arg Tyr Phe Ile Phe
625                 630                 635                 640

Gly Gly Gly Tyr Val Tyr Phe Glu Glu Tyr Ala Tyr Ser His Gln Leu
                645                 650                 655

Ser Arg Ala Asp Val Thr Thr Val Ser Thr Phe Ile Asp Leu Asn Ile
            660                 665                 670

Thr Met Leu Glu Asp His Glu Phe Val Pro Leu Glu Val Tyr Thr Arg
        675                 680                 685

His Glu Ile Lys Asp Ser Gly Leu Leu Asp Tyr Thr Glu Val Gln Arg
    690                 695                 700

Arg Asn Gln Leu His Asp Leu Arg Phe Ala Asp Ile Asp Thr Val Ile
705                 710                 715                 720

Arg Ala Asp Ala Asn Ala Ala Met Phe Ala Gly Leu Cys Ala Phe Phe
                725                 730                 735

Glu Gly Met Gly Asp Leu Gly Arg Ala Val Gly Lys Val Val Met Gly
            740                 745                 750

Val Val Gly Gly Val Val Ser Ala Val Ser Gly Val Ser Ser Phe Met
        755                 760                 765

Ser Asn Pro Phe Gly Ala Leu Ala Val Gly Leu Leu Val Leu Ala Gly
    770                 775                 780

Leu Val Ala Ala Phe Phe Ala Phe Arg Tyr Val Leu Gln Leu Gln Arg
785                 790                 795                 800

Asn Pro Met Lys Ala Leu Tyr Pro Leu Thr Thr Lys Glu Leu Lys Thr
                805                 810                 815

Ser Asp Pro Gly Gly Val Gly Gly Glu Gly Glu Glu Gly Ala Glu Gly
            820                 825                 830

Gly Gly Phe Asp Glu Ala Lys Leu Ala Glu Ala Arg Glu Met Ile Arg
        835                 840                 845

Tyr Met Ala Leu Val Ser Ala Met Glu Arg Thr Glu His Lys Ala Arg
    850                 855                 860

Lys Lys Gly Thr Ser Ala Leu Leu Ser Ser Lys Val Thr Asn Met Val
865                 870                 875                 880

Leu Arg Lys Arg Asn Lys Ala Arg Tyr Ser Pro Leu His Asn Glu Asp
                885                 890                 895

Glu Ala Gly Asp Glu Asp Glu Leu
            900

<210> SEQ ID NO 15
<211> LENGTH: 904
<212> TYPE: PRT
<213> ORGANISM: HSV2 strain 333

<400> SEQUENCE: 15

Met Arg Gly Gly Gly Leu Ile Cys Ala Leu Val Val Gly Ala Leu Val
1               5                   10                  15

Ala Ala Val Ala Ser Ala Ala Pro Ala Ala Pro Ala Pro Arg Ala
                20                  25                  30

Ser Gly Gly Val Ala Ala Thr Val Ala Ala Asn Gly Gly Pro Ala Ser
            35                  40                  45

Arg Pro Pro Pro Val Pro Ser Pro Ala Thr Thr Lys Ala Arg Lys Arg
```

```
            50                  55                  60
Lys Thr Lys Lys Pro Pro Lys Arg Pro Glu Ala Thr Pro Pro Asp
65                  70                  75                  80

Ala Asn Ala Thr Val Ala Ala Gly His Ala Thr Leu Arg Ala His Leu
                85                  90                  95

Arg Glu Ile Lys Val Glu Asn Ala Asp Ala Gln Phe Tyr Val Cys Pro
                100                 105                 110

Pro Pro Thr Gly Ala Thr Val Val Gln Phe Glu Gln Pro Arg Arg Cys
            115                 120                 125

Pro Thr Arg Pro Glu Gly Gln Asn Tyr Thr Glu Gly Ile Ala Val Val
        130                 135                 140

Phe Lys Glu Asn Ile Ala Pro Tyr Lys Phe Lys Ala Thr Met Tyr Tyr
145                 150                 155                 160

Lys Asp Val Thr Val Ser Gln Val Trp Phe Gly His Arg Tyr Ser Gln
                165                 170                 175

Phe Met Gly Ile Phe Glu Asp Arg Ala Pro Val Pro Phe Glu Glu Val
            180                 185                 190

Ile Asp Lys Ile Asn Ala Lys Gly Val Cys Arg Ser Thr Ala Lys Tyr
        195                 200                 205

Val Arg Asn Asn Met Glu Thr Thr Ala Phe His Arg Asp Asp His Glu
210                 215                 220

Thr Asp Met Glu Leu Lys Pro Ala Lys Val Ala Thr Arg Thr Ser Arg
225                 230                 235                 240

Gly Trp His Thr Thr Asp Leu Lys Tyr Asn Pro Ser Arg Val Glu Ala
                245                 250                 255

Phe His Arg Tyr Gly Thr Thr Val Thr Cys Ile Val Glu Glu Val Asp
            260                 265                 270

Ala Arg Ser Val Tyr Pro Tyr Asp Glu Phe Val Leu Ala Thr Gly Asp
        275                 280                 285

Phe Val Tyr Met Ser Pro Phe Tyr Gly Tyr Arg Glu Gly Ser His Thr
        290                 295                 300

Glu His Thr Ser Tyr Ala Ala Asp Arg Phe Lys Gln Val Asp Gly Phe
305                 310                 315                 320

Tyr Ala Arg Asp Leu Thr Thr Lys Ala Arg Ala Thr Ser Pro Thr Thr
                325                 330                 335

Arg Asn Leu Leu Thr Thr Pro Lys Phe Thr Val Ala Trp Asp Trp Val
            340                 345                 350

Pro Lys Arg Pro Ala Val Cys Thr Met Thr Lys Trp Gln Glu Val Asp
        355                 360                 365

Glu Met Leu Arg Ala Glu Tyr Gly Gly Ser Phe Arg Phe Ser Ser Asp
370                 375                 380

Ala Ile Ser Thr Thr Phe Thr Thr Asn Leu Thr Gln Tyr Ser Leu Ser
385                 390                 395                 400

Arg Val Asp Leu Gly Asp Cys Ile Gly Arg Asp Ala Arg Glu Ala Ile
                405                 410                 415

Asp Arg Met Phe Ala Arg Lys Tyr Asn Ala Thr His Ile Lys Val Gly
            420                 425                 430

Gln Pro Gln Tyr Tyr Leu Ala Thr Gly Gly Phe Leu Ile Ala Tyr Gln
        435                 440                 445

Pro Leu Leu Ser Asn Thr Leu Ala Glu Leu Tyr Val Arg Glu Tyr Met
    450                 455                 460

Arg Glu Gln Asp Arg Lys Pro Arg Asn Ala Thr Pro Ala Pro Leu Arg
465                 470                 475                 480
```

-continued

```
Glu Ala Pro Ser Ala Asn Ala Ser Val Glu Arg Ile Lys Thr Thr Ser
                485                 490                 495
Ser Ile Glu Phe Ala Arg Leu Gln Phe Thr Tyr Asn His Ile Gln Arg
            500                 505                 510
His Val Asn Asp Met Leu Gly Arg Ile Ala Val Ala Trp Cys Glu Leu
        515                 520                 525
Gln Asn His Glu Leu Thr Leu Trp Asn Glu Ala Arg Lys Leu Asn Pro
    530                 535                 540
Asn Ala Ile Ala Ser Ala Thr Val Gly Arg Arg Val Ser Ala Arg Met
545                 550                 555                 560
Leu Gly Asp Val Met Ala Val Ser Thr Cys Val Pro Val Ala Pro Asp
                565                 570                 575
Asn Val Ile Val Gln Asn Ser Met Arg Val Ser Ser Arg Pro Gly Thr
            580                 585                 590
Cys Tyr Ser Arg Pro Leu Val Ser Phe Arg Tyr Glu Asp Gln Gly Pro
        595                 600                 605
Leu Ile Glu Gly Gln Leu Gly Glu Asn Asn Glu Leu Arg Leu Thr Arg
    610                 615                 620
Asp Ala Leu Glu Pro Cys Thr Val Gly His Arg Arg Tyr Phe Ile Phe
625                 630                 635                 640
Gly Gly Gly Tyr Val Tyr Phe Glu Glu Tyr Ala Tyr Ser His Gln Leu
                645                 650                 655
Ser Arg Ala Asp Val Thr Thr Val Ser Thr Phe Ile Asp Leu Asn Ile
            660                 665                 670
Thr Met Leu Glu Asp His Glu Phe Val Pro Leu Gly Val Tyr Thr Arg
        675                 680                 685
His Glu Ile Lys Asp Ser Gly Leu Leu Asp Tyr Thr Glu Val Gln Arg
    690                 695                 700
Arg Asn Gln Leu His Asp Leu Arg Phe Ala Asp Ile Asp Thr Val Ile
705                 710                 715                 720
Arg Ala Asp Ala Asn Ala Ala Met Phe Ala Gly Leu Cys Ala Phe Phe
                725                 730                 735
Glu Gly Met Gly Asp Leu Gly Arg Ala Val Gly Lys Val Val Met Gly
            740                 745                 750
Val Val Gly Gly Val Val Ser Ala Val Ser Gly Val Ser Ser Phe Met
        755                 760                 765
Ser Asn Pro Phe Gly Ala Leu Ala Val Gly Leu Leu Val Leu Ala Gly
    770                 775                 780
Leu Val Ala Ala Phe Phe Ala Phe Arg Tyr Val Leu Gln Leu Gln Arg
785                 790                 795                 800
Asn Pro Met Lys Ala Leu Tyr Pro Leu Thr Thr Lys Glu Leu Lys Thr
                805                 810                 815
Ser Asp Pro Gly Gly Val Gly Gly Glu Gly Glu Glu Gly Ala Glu Gly
            820                 825                 830
Gly Gly Phe Asp Glu Ala Lys Leu Ala Glu Ala Arg Glu Met Ile Arg
        835                 840                 845
Tyr Met Ala Leu Val Ser Ala Met Glu Arg Thr Glu His Lys Ala Arg
    850                 855                 860
Lys Lys Gly Thr Ser Ala Leu Leu Ser Ser Lys Val Thr Asn Met Val
865                 870                 875                 880
Leu Arg Lys Arg Asn Lys Ala Arg Tyr Ser Pro Leu His Asn Glu Asp
                885                 890                 895
```

Glu Ala Gly Asp Glu Asp Glu Leu
            900

<210> SEQ ID NO 16
<211> LENGTH: 901
<212> TYPE: PRT
<213> ORGANISM: HSV2 strain MMA

<400> SEQUENCE: 16

Met Arg Gly Gly Gly Leu Ile Cys Ala Leu Val Val Gly Ala Leu Val
1               5                   10                  15

Ala Ala Val Ala Ser Ala Ala Pro Ala Ala Pro Arg Ala Ser Gly Gly
            20                  25                  30

Val Ala Ala Thr Val Ala Ala Asn Gly Gly Pro Ala Ser Arg Pro Pro
        35                  40                  45

Pro Val Pro Ser Pro Ala Thr Thr Arg Ala Arg Lys Arg Lys Thr Lys
    50                  55                  60

Lys Pro Pro Glu Arg Pro Glu Ala Thr Pro Pro Asp Ala Asn Ala
65                  70                  75                  80

Thr Val Ala Ala Gly His Ala Thr Leu Arg Ala His Leu Arg Glu Ile
                85                  90                  95

Lys Val Glu Asn Ala Asp Ala Gln Phe Tyr Val Cys Pro Pro Pro Thr
            100                 105                 110

Gly Ala Thr Val Val Gln Phe Glu Gln Pro Arg Arg Cys Pro Thr Arg
        115                 120                 125

Pro Glu Gly Gln Asn Tyr Thr Glu Gly Ile Ala Val Val Phe Lys Glu
    130                 135                 140

Asn Ile Ala Pro Tyr Lys Phe Lys Ala Thr Met Tyr Tyr Lys Asp Val
145                 150                 155                 160

Thr Val Ser Gln Val Trp Phe Gly His Arg Tyr Ser Gln Phe Met Gly
                165                 170                 175

Ile Phe Glu Asp Arg Ala Pro Val Pro Phe Glu Glu Val Ile Asp Lys
            180                 185                 190

Ile Asn Ala Lys Gly Val Cys Arg Ser Thr Ala Lys Tyr Val Arg Asn
        195                 200                 205

Asn Met Glu Thr Thr Ala Phe His Arg Asp Asp His Glu Thr Asp Met
    210                 215                 220

Glu Leu Lys Pro Ala Lys Val Ala Thr Arg Thr Ser Arg Gly Trp His
225                 230                 235                 240

Thr Thr Asp Leu Lys Tyr Asn Pro Ser Arg Val Glu Ala Phe His Arg
                245                 250                 255

Tyr Gly Thr Thr Val Asn Cys Ile Val Glu Glu Val Asp Ala Arg Ser
            260                 265                 270

Val Tyr Pro Tyr Asp Glu Phe Val Leu Ala Thr Gly Asp Phe Val Tyr
        275                 280                 285

Met Ser Pro Phe Tyr Gly Tyr Arg Glu Gly Ser His Thr Glu His Thr
    290                 295                 300

Ser Tyr Ala Ala Asp Arg Phe Lys Gln Val Asp Gly Phe Tyr Ala Arg
305                 310                 315                 320

Asp Leu Thr Thr Lys Ala Gln Ala Thr Ser Pro Thr Thr Arg Asn Leu
                325                 330                 335

Leu Thr Thr Pro Lys Phe Thr Val Ala Trp Asp Trp Val Pro Lys Arg
            340                 345                 350

Pro Ala Val Cys Thr Met Thr Lys Trp Gln Glu Val Asp Glu Met Leu
        355                 360                 365

```
Arg Ala Glu Tyr Gly Gly Ser Phe Arg Phe Ser Ser Asp Ala Ile Ser
        370                 375                 380

Thr Thr Phe Thr Thr Asn Leu Thr Glu Tyr Ser Leu Ser Arg Val Asp
385                 390                 395                 400

Leu Gly Asp Cys Ile Gly Arg Asp Ala Arg Glu Ala Ile Asp Arg Met
                405                 410                 415

Phe Ala Arg Lys Tyr Asn Ala Thr His Ile Lys Val Gly Gln Pro Gln
                420                 425                 430

Tyr Tyr Leu Ala Thr Gly Gly Phe Leu Ile Ala Tyr Gln Pro Leu Leu
                435                 440                 445

Ser Asn Thr Leu Ala Glu Leu Tyr Val Arg Glu Tyr Met Arg Glu Gln
450                 455                 460

Asp Arg Lys Pro Arg Asn Ala Thr Pro Ala Pro Leu Arg Glu Ala Pro
465                 470                 475                 480

Ser Ala Asn Ala Ser Val Glu Arg Ile Lys Thr Thr Ser Ser Ile Glu
                485                 490                 495

Phe Ala Arg Leu Gln Phe Thr Tyr Asn His Ile Gln Arg His Val Asn
                500                 505                 510

Asp Met Leu Gly Arg Ile Ala Val Ala Trp Cys Glu Leu Gln Asn His
                515                 520                 525

Glu Leu Thr Leu Trp Asn Glu Ala Arg Lys Leu Asn Pro Asn Ala Ile
530                 535                 540

Ala Ser Ala Thr Val Gly Arg Arg Val Ser Ala Arg Met Leu Gly Asp
545                 550                 555                 560

Val Met Ala Val Ser Thr Cys Val Pro Val Ala Pro Asp Asn Val Ile
                565                 570                 575

Val Gln Asn Ser Met Arg Val Ser Ser Arg Pro Gly Thr Cys Tyr Ser
                580                 585                 590

Arg Pro Leu Val Ser Phe Arg Tyr Glu Asp Gln Gly Pro Leu Ile Glu
                595                 600                 605

Gly Gln Leu Gly Glu Asn Asn Glu Leu Arg Leu Thr Arg Asp Ala Leu
                610                 615                 620

Glu Pro Cys Thr Val Gly His Arg Arg Tyr Phe Ile Phe Gly Gly Gly
625                 630                 635                 640

Tyr Val Tyr Phe Glu Glu Tyr Ala Tyr Ser His Gln Leu Ser Arg Ala
                645                 650                 655

Asp Val Thr Thr Val Ser Thr Phe Ile Asp Leu Asn Ile Thr Met Leu
                660                 665                 670

Glu Asp His Glu Phe Val Pro Leu Glu Val Tyr Thr Arg His Glu Ile
                675                 680                 685

Lys Asp Ser Gly Leu Leu Asp Tyr Thr Glu Val Gln Arg Arg Asn Gln
690                 695                 700

Leu His Asp Leu Arg Phe Ala Asp Ile Asp Thr Val Ile Arg Ala Asp
705                 710                 715                 720

Ala Asn Ala Ala Met Phe Ala Gly Leu Cys Ala Phe Glu Gly Met
                725                 730                 735

Gly Asp Leu Gly Arg Ala Val Gly Lys Val Val Met Gly Val Val Gly
                740                 745                 750

Gly Val Val Ser Ala Val Ser Gly Val Ser Ser Phe Met Ser Asn Pro
                755                 760                 765

Phe Gly Ala Leu Ala Val Gly Leu Leu Val Leu Ala Gly Leu Val Ala
                770                 775                 780
```

```
Ala Phe Phe Ala Phe Arg Tyr Val Leu Gln Leu Gln Arg Asn Pro Met
785                 790                 795                 800

Lys Ala Leu Tyr Pro Leu Thr Thr Lys Glu Leu Lys Thr Ser Asp Pro
                805                 810                 815

Gly Gly Val Gly Gly Glu Gly Glu Gly Ala Glu Gly Gly Phe
            820                 825                 830

Asp Glu Ala Lys Leu Ala Glu Ala Arg Glu Met Ile Arg Tyr Met Ala
                835                 840                 845

Leu Val Ser Ala Met Glu Arg Thr Glu His Lys Ala Arg Lys Lys Gly
            850                 855                 860

Thr Ser Ala Leu Leu Ser Ser Lys Val Thr Asn Met Val Leu Arg Lys
865                 870                 875                 880

Arg Asn Lys Ala Arg Tyr Ser Pro Leu His Asn Glu Asp Gly Ala Gly
                885                 890                 895

Asp Glu Asp Glu Leu
            900

<210> SEQ ID NO 17
<211> LENGTH: 15
<212> TYPE: PRT
<213> ORGANISM: Artificial Sequence
<220> FEATURE:
<223> OTHER INFORMATION: Mab 2c binding epitope

<400> SEQUENCE: 17

Ser Pro Phe Tyr Gly Tyr Arg Glu Gly Ser His Thr Glu His Thr
1               5                   10                  15

<210> SEQ ID NO 18
<211> LENGTH: 13
<212> TYPE: PRT
<213> ORGANISM: HSV

<400> SEQUENCE: 18

Gln Val Trp Phe Gly His Arg Tyr Ser Gln Phe Met Gly
1               5                   10

<210> SEQ ID NO 19
<211> LENGTH: 7
<212> TYPE: PRT
<213> ORGANISM: HSV

<400> SEQUENCE: 19

Val Trp Phe Gly His Arg Tyr
1               5

<210> SEQ ID NO 20
<211> LENGTH: 6
<212> TYPE: PRT
<213> ORGANISM: HSV

<400> SEQUENCE: 20

Tyr Ser Gln Phe Met Gly
1               5

<210> SEQ ID NO 21
<211> LENGTH: 6
<212> TYPE: PRT
<213> ORGANISM: HSV

<400> SEQUENCE: 21

Phe Tyr Gly Tyr Arg Glu
```

```
<210> SEQ ID NO 22
<211> LENGTH: 13
<212> TYPE: PRT
<213> ORGANISM: HSV
<220> FEATURE:
<221> NAME/KEY: VARIANT
<222> LOCATION: (7)..(7)

<400> SEQUENCE: 22

Tyr Ser Gln Phe Met Gly Asx Phe Tyr Gly Tyr Arg Glu
1               5                   10

<210> SEQ ID NO 23
<211> LENGTH: 11
<212> TYPE: PRT
<213> ORGANISM: HSV
<220> FEATURE:
<221> NAME/KEY: VARIANT
<222> LOCATION: (4)..(5)

<400> SEQUENCE: 23

Phe Glu Asp Asx Asx Phe Tyr Gly Tyr Arg Glu
1               5                   10

<210> SEQ ID NO 24
<211> LENGTH: 19
<212> TYPE: DNA
<213> ORGANISM: Artificial Sequence
<220> FEATURE:
<223> OTHER INFORMATION: Y296N

<400> SEQUENCE: 24
gggacatgtt cacaaagtc                                               19

<210> SEQ ID NO 25
<211> LENGTH: 19
<212> TYPE: DNA
<213> ORGANISM: Artificial Sequence
<220> FEATURE:
<223> OTHER INFORMATION: M296F

<400> SEQUENCE: 25
gggacatgaa cacaaagtc                                               19

<210> SEQ ID NO 26
<211> LENGTH: 19
<212> TYPE: DNA
<213> ORGANISM: Artificial Sequence
<220> FEATURE:
<223> OTHER INFORMATION: M297L

<400> SEQUENCE: 26
acggggacag gtacacaaa                                               19

<210> SEQ ID NO 27
<211> LENGTH: 19
<212> TYPE: DNA
<213> ORGANISM: Artificial Sequence
<220> FEATURE:
<223> OTHER INFORMATION: M297T

<400> SEQUENCE: 27
aacggggacg tgtacacaa                                               19
```

```
<210> SEQ ID NO 28
<211> LENGTH: 19
<212> TYPE: DNA
<213> ORGANISM: Artificial Sequence
<220> FEATURE:
<223> OTHER INFORMATION: M297V

<400> SEQUENCE: 28
acggggacac gtacacaaa                                              19

<210> SEQ ID NO 29
<211> LENGTH: 19
<212> TYPE: DNA
<213> ORGANISM: Artificial Sequence
<220> FEATURE:
<223> OTHER INFORMATION: S268A

<400> SEQUENCE: 29
aaaacggggc catgtacac                                              19

<210> SEQ ID NO 30
<211> LENGTH: 19
<212> TYPE: DNA
<213> ORGANISM: Artificial Sequence
<220> FEATURE:
<223> OTHER INFORMATION: P299S

<400> SEQUENCE: 30
cgtaaaacga ggacatgta                                              19

<210> SEQ ID NO 31
<211> LENGTH: 19
<212> TYPE: DNA
<213> ORGANISM: Artificial Sequence
<220> FEATURE:
<223> OTHER INFORMATION: F300Y

<400> SEQUENCE: 31
tagccgtaat acggggaca                                              19

<210> SEQ ID NO 32
<211> LENGTH: 19
<212> TYPE: DNA
<213> ORGANISM: Artificial Sequence
<220> FEATURE:
<223> OTHER INFORMATION: F300I

<400> SEQUENCE: 32
tagccgtaaa tcggggaca                                              19

<210> SEQ ID NO 33
<211> LENGTH: 17
<212> TYPE: DNA
<213> ORGANISM: Artificial Sequence
<220> FEATURE:
<223> OTHER INFORMATION: Y301N

<400> SEQUENCE: 33
gtagccgtta aacgggg                                                17

<210> SEQ ID NO 34
<211> LENGTH: 19
<212> TYPE: DNA
<213> ORGANISM: Artificial Sequence
<220> FEATURE:
<223> OTHER INFORMATION: G302R
```

-continued

```
<400> SEQUENCE: 34
cccggtagcg gtaaaacgg                                                  19

<210> SEQ ID NO 35
<211> LENGTH: 19
<212> TYPE: DNA
<213> ORGANISM: Artificial Sequence
<220> FEATURE:
<223> OTHER INFORMATION: G302V

<400> SEQUENCE: 35
tcccggtaga cgtaaaacg                                                  19

<210> SEQ ID NO 36
<211> LENGTH: 24
<212> TYPE: DNA
<213> ORGANISM: Artificial Sequence
<220> FEATURE:
<223> OTHER INFORMATION: Y303N

<400> SEQUENCE: 36
acccctcccg gttgccgtaa aacg                                            24

<210> SEQ ID NO 37
<211> LENGTH: 19
<212> TYPE: DNA
<213> ORGANISM: Artificial Sequence
<220> FEATURE:
<223> OTHER INFORMATION: R304G

<400> SEQUENCE: 37 accccctcccc gtagccgta                                                 19

<210> SEQ ID NO 38
<211> LENGTH: 19
<212> TYPE: DNA
<213> ORGANISM: Artificial Sequence
<220> FEATURE:
<223> OTHER INFORMATION: R304L

<400> SEQUENCE: 38 gaccccctcca ggtagccgt                                                 19

<210> SEQ ID NO 39
<211> LENGTH: 23
<212> TYPE: DNA
<213> ORGANISM: Artificial Sequence
<220> FEATURE:
<223> OTHER INFORMATION: E305K

<400> SEQUENCE: 39
gtgcgacccc ttccggtagc cgt                                             23

<210> SEQ ID NO 40
<211> LENGTH: 19
<212> TYPE: DNA
<213> ORGANISM: Artificial Sequence
<220> FEATURE:
<223> OTHER INFORMATION: G306A

<400> SEQUENCE: 40
gtgtgcgacg cctcccggt                                                  19

<210> SEQ ID NO 41
<211> LENGTH: 19
```

```
<212> TYPE: DNA
<213> ORGANISM: Artificial Sequence
<220> FEATURE:
<223> OTHER INFORMATION: G306V

<400> SEQUENCE: 41
gtgtgcgaca cctcccggt                                              19

<210> SEQ ID NO 42
<211> LENGTH: 19
<212> TYPE: DNA
<213> ORGANISM: Artificial Sequence
<220> FEATURE:
<223> OTHER INFORMATION: S307A

<400> SEQUENCE: 42
cggtgtgcgc ccctcccg                                               19

<210> SEQ ID NO 43
<211> LENGTH: 15
<212> TYPE: PRT
<213> ORGANISM: HSV

<400> SEQUENCE: 43

Arg Tyr Ser Gln Phe Met Gly Ile Phe Glu Asp Arg Ala Pro Val
1               5                   10                  15

<210> SEQ ID NO 44
<211> LENGTH: 21
<212> TYPE: PRT
<213> ORGANISM: HSV

<400> SEQUENCE: 44

Phe Gly His Arg Tyr Ser Gln Phe Met Gly Ile Phe Glu Asp Arg Ala
1               5                   10                  15

Pro Val Pro Phe Glu
            20

<210> SEQ ID NO 45
<211> LENGTH: 9
<212> TYPE: PRT
<213> ORGANISM: HSV

<400> SEQUENCE: 45

Gln Phe Met Gly Ile Phe Glu Asp Arg
1               5

<210> SEQ ID NO 46
<211> LENGTH: 18
<212> TYPE: PRT
<213> ORGANISM: HSV

<400> SEQUENCE: 46

Ser Pro Phe Tyr Gly Tyr Arg Glu Gly Ser His Thr Glu His Thr Ser
1               5                   10                  15

Tyr Ala

<210> SEQ ID NO 47
<211> LENGTH: 12
<212> TYPE: PRT
<213> ORGANISM: HSV

<400> SEQUENCE: 47

Tyr Gly Tyr Arg Glu Gly Ser His Thr Glu His Thr
```

<210> SEQ ID NO 48
<211> LENGTH: 15
<212> TYPE: PRT
<213> ORGANISM: HSV

<400> SEQUENCE: 48

Ser Pro Phe Tyr Gly Tyr Arg Glu Gly Ser His Thr Glu His Thr
1               5                   10                  15

<210> SEQ ID NO 49
<211> LENGTH: 9
<212> TYPE: PRT
<213> ORGANISM: HSV

<400> SEQUENCE: 49

Phe Tyr Gly Tyr Arg Glu Gly Ser His
1               5

<210> SEQ ID NO 50
<211> LENGTH: 6
<212> TYPE: PRT
<213> ORGANISM: HSV

<400> SEQUENCE: 50

Tyr Gly Tyr Arg Glu Gly
1               5

<210> SEQ ID NO 51
<211> LENGTH: 7
<212> TYPE: PRT
<213> ORGANISM: HSV

<400> SEQUENCE: 51

Phe Tyr Gly Tyr Arg Glu Gly
1               5

<210> SEQ ID NO 52
<211> LENGTH: 12
<212> TYPE: PRT
<213> ORGANISM: Artificial Sequence
<220> FEATURE:
<223> OTHER INFORMATION: computationally designed binding peptide

<400> SEQUENCE: 52

Pro Phe Tyr Gly Tyr Arg Glu Gly Phe Glu Asp Phe
1               5                   10

<210> SEQ ID NO 53
<211> LENGTH: 7
<212> TYPE: PRT
<213> ORGANISM: HSV

<400> SEQUENCE: 53

Pro Phe Tyr Gly Tyr Arg Glu
1               5

<210> SEQ ID NO 54
<211> LENGTH: 4
<212> TYPE: PRT
<213> ORGANISM: Artificial Sequence
<220> FEATURE:
<223> OTHER INFORMATION: binding motif

<400> SEQUENCE: 54

Phe Glu Asp Phe
1

<210> SEQ ID NO 55
<211> LENGTH: 122
<212> TYPE: PRT
<213> ORGANISM: Artificial Sequence
<220> FEATURE:
<223> OTHER INFORMATION: VHhum2c

<400> SEQUENCE: 55

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala His Ile Trp Trp Asn Asp Lys Tyr Tyr Lys Pro Ala
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Tyr Tyr Gly Tyr Arg Pro Tyr Ala Met Asp Tyr Trp
            100                 105                 110

Gly Gln Gly Thr Leu Val Thr Val Ser Ser
        115                 120

<210> SEQ ID NO 56
<211> LENGTH: 113
<212> TYPE: PRT
<213> ORGANISM: Artificial Sequence
<220> FEATURE:
<223> OTHER INFORMATION: VLhum2c

<400> SEQUENCE: 56

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Ser Phe Gly Gln Gly Thr Lys Val Glu Ile Lys
            100                 105                 110

Arg

<210> SEQ ID NO 57
<211> LENGTH: 13
<212> TYPE: PRT
<213> ORGANISM: HSV

<400> SEQUENCE: 57

```
Phe Gly His Arg Tyr Ser Gln Phe Met Gly Ile Phe Glu
1               5                   10
```

<210> SEQ ID NO 58
<211> LENGTH: 13
<212> TYPE: PRT
<213> ORGANISM: HSV

<400> SEQUENCE: 58

```
Arg Tyr Ser Gln Phe Met Gly Ile Phe Glu Asp Arg Ala
1               5                   10
```

<210> SEQ ID NO 59
<211> LENGTH: 13
<212> TYPE: PRT
<213> ORGANISM: HSV

<400> SEQUENCE: 59

```
Gln Phe Met Gly Ile Phe Glu Asp Arg Ala Pro Val Pro
1               5                   10
```

<210> SEQ ID NO 60
<211> LENGTH: 13
<212> TYPE: PRT
<213> ORGANISM: HSV

<400> SEQUENCE: 60

```
Gly Ile Phe Glu Asp Arg Ala Pro Val Pro Phe Glu Glu
1               5                   10
```

<210> SEQ ID NO 61
<211> LENGTH: 13
<212> TYPE: PRT
<213> ORGANISM: HSV

<400> SEQUENCE: 61

```
Val Tyr Met Ser Pro Phe Tyr Gly Tyr Arg Glu Gly Ser
1               5                   10
```

<210> SEQ ID NO 62
<211> LENGTH: 13
<212> TYPE: PRT
<213> ORGANISM: HSV

<400> SEQUENCE: 62

```
Ser Pro Phe Tyr Gly Tyr Arg Glu Gly Ser His Thr Glu
1               5                   10
```

<210> SEQ ID NO 63
<211> LENGTH: 13
<212> TYPE: PRT
<213> ORGANISM: HSV

<400> SEQUENCE: 63

```
Tyr Gly Tyr Arg Glu Gly Ser His Thr Glu His Thr Ser
1               5                   10
```

<210> SEQ ID NO 64
<211> LENGTH: 13
<212> TYPE: PRT
<213> ORGANISM: HSV

<400> SEQUENCE: 64

```
Arg Tyr Ser Gln Phe Met Gly Ile Phe Glu Asp Arg Ala
1               5                   10
```

<210> SEQ ID NO 65
<211> LENGTH: 13
<212> TYPE: PRT
<213> ORGANISM: HSV

<400> SEQUENCE: 65

Ser Pro Phe Tyr Gly Tyr Arg Glu Gly Ser His Thr Glu
1               5                   10

<210> SEQ ID NO 66
<211> LENGTH: 12
<212> TYPE: PRT
<213> ORGANISM: HSV

<400> SEQUENCE: 66

Tyr Ser Gln Phe Met Gly Phe Tyr Gly Tyr Arg Glu
1               5                   10

<210> SEQ ID NO 67
<211> LENGTH: 13
<212> TYPE: PRT
<213> ORGANISM: Artificial Sequence
<220> FEATURE:
<223> OTHER INFORMATION: modified consensus sequence I
<220> FEATURE:
<221> NAME/KEY: X
<222> LOCATION: (7)..(7)
<223> OTHER INFORMATION: beta alanine spacer

<400> SEQUENCE: 67

Tyr Ser Gln Phe Met Gly Xaa Phe Tyr Gly Tyr Arg Glu
1               5                   10

<210> SEQ ID NO 68
<211> LENGTH: 14
<212> TYPE: PRT
<213> ORGANISM: Artificial Sequence
<220> FEATURE:
<223> OTHER INFORMATION: modified consensus sequence II
<220> FEATURE:
<221> NAME/KEY: X
<222> LOCATION: (7)..(8)
<223> OTHER INFORMATION: betaalanyl-betaalanyl spacer

<400> SEQUENCE: 68

Tyr Ser Gln Phe Met Gly Xaa Xaa Phe Tyr Gly Tyr Arg Glu
1               5                   10

<210> SEQ ID NO 69
<211> LENGTH: 12
<212> TYPE: PRT
<213> ORGANISM: HSV

<400> SEQUENCE: 69

Phe Tyr Gly Tyr Arg Glu Tyr Ser Gln Phe Met Gly
1               5                   10

<210> SEQ ID NO 70
<211> LENGTH: 13
<212> TYPE: PRT
<213> ORGANISM: Artificial Sequence
<220> FEATURE:
<223> OTHER INFORMATION: modified consensus sequence III
<220> FEATURE:
<221> NAME/KEY: X
<222> LOCATION: (7)..(7)
<223> OTHER INFORMATION: betaalanyl spacer

```
<400> SEQUENCE: 70

Phe Tyr Gly Tyr Arg Glu Xaa Tyr Ser Gln Phe Met Gly
1               5                   10

<210> SEQ ID NO 71
<211> LENGTH: 14
<212> TYPE: PRT
<213> ORGANISM: Artificial Sequence
<220> FEATURE:
<223> OTHER INFORMATION: modified consensus sequence IV
<220> FEATURE:
<221> NAME/KEY: X
<222> LOCATION: (7)..(8)
<223> OTHER INFORMATION: betaalanyl-betaalanyl spacer

<400> SEQUENCE: 71

Phe Tyr Gly Tyr Arg Glu Xaa Xaa Tyr Ser Gln Phe Met Gly
1               5                   10

<210> SEQ ID NO 72
<211> LENGTH: 9
<212> TYPE: PRT
<213> ORGANISM: HSV

<400> SEQUENCE: 72

Phe Glu Asp Phe Tyr Gly Tyr Arg Glu
1               5

<210> SEQ ID NO 73
<211> LENGTH: 10
<212> TYPE: PRT
<213> ORGANISM: Artificial Sequence
<220> FEATURE:
<223> OTHER INFORMATION: modified consensus sequence V
<220> FEATURE:
<221> NAME/KEY: X
<222> LOCATION: (4)..(4)
<223> OTHER INFORMATION: betaalanyl spacer

<400> SEQUENCE: 73

Phe Glu Asp Xaa Phe Tyr Gly Tyr Arg Glu
1               5                   10

<210> SEQ ID NO 74
<211> LENGTH: 11
<212> TYPE: PRT
<213> ORGANISM: Artificial Sequence
<220> FEATURE:
<223> OTHER INFORMATION: modified consensus sequence VI
<220> FEATURE:
<221> NAME/KEY: X
<222> LOCATION: (4)..(5)
<223> OTHER INFORMATION: betaalanyl-betaalanyl spacer

<400> SEQUENCE: 74

Phe Glu Asp Xaa Xaa Phe Tyr Gly Tyr Arg Glu
1               5                   10

<210> SEQ ID NO 75
<211> LENGTH: 9
<212> TYPE: PRT
<213> ORGANISM: HSV

<400> SEQUENCE: 75

Phe Tyr Gly Tyr Arg Glu Phe Glu Asp
1               5
```

<210> SEQ ID NO 76
<211> LENGTH: 10
<212> TYPE: PRT
<213> ORGANISM: Artificial Sequence
<220> FEATURE:
<223> OTHER INFORMATION: modified consensus sequence VII
<220> FEATURE:
<221> NAME/KEY: X
<222> LOCATION: (7)..(7)
<223> OTHER INFORMATION: betaalanyl spacer

<400> SEQUENCE: 76

Phe Tyr Gly Tyr Arg Glu Xaa Phe Glu Asp
1               5                   10

<210> SEQ ID NO 77
<211> LENGTH: 11
<212> TYPE: PRT
<213> ORGANISM: Artificial Sequence
<220> FEATURE:
<223> OTHER INFORMATION: modified consensus sequence VIII
<220> FEATURE:
<221> NAME/KEY: X
<222> LOCATION: (7)..(8)
<223> OTHER INFORMATION: betaalanyl-betaalanyl spacer

<400> SEQUENCE: 77

Phe Tyr Gly Tyr Arg Glu Xaa Xaa Phe Glu Asp
1               5                   10

<210> SEQ ID NO 78
<211> LENGTH: 15
<212> TYPE: PRT
<213> ORGANISM: HSV

<400> SEQUENCE: 78

Phe Gly His Arg Tyr Ser Gln Phe Met Gly Ile Phe Glu Asp Arg
1               5                   10                  15

<210> SEQ ID NO 79
<211> LENGTH: 15
<212> TYPE: PRT
<213> ORGANISM: HSV

<400> SEQUENCE: 79

Gln Phe Met Gly Ile Phe Glu Asp Arg Ala Pro Val Pro Phe Glu
1               5                   10                  15

<210> SEQ ID NO 80
<211> LENGTH: 15
<212> TYPE: PRT
<213> ORGANISM: HSV

<400> SEQUENCE: 80

Ser Pro Phe Tyr Gly Tyr Arg Glu Gly Ser His Thr Glu His Thr
1               5                   10                  15

<210> SEQ ID NO 81
<211> LENGTH: 15
<212> TYPE: PRT
<213> ORGANISM: HSV

<400> SEQUENCE: 81

Tyr Gly Tyr Arg Glu Gly Ser His Thr Glu His Thr Ser Tyr Ala
1               5                   10                  15

```
<210> SEQ ID NO 82
<211> LENGTH: 13
<212> TYPE: PRT
<213> ORGANISM: HSV

<400> SEQUENCE: 82

Tyr Met Ser Pro Phe Tyr Gly Tyr Arg Glu Gly Ser His
1               5                   10

<210> SEQ ID NO 83
<211> LENGTH: 13
<212> TYPE: PRT
<213> ORGANISM: HSV

<400> SEQUENCE: 83

Met Ser Pro Phe Tyr Gly Tyr Arg Glu Gly Ser His Thr
1               5                   10

<210> SEQ ID NO 84
<211> LENGTH: 13
<212> TYPE: PRT
<213> ORGANISM: HSV

<400> SEQUENCE: 84

Ser Pro Phe Tyr Gly Tyr Arg Glu Gly Ser His Thr Glu
1               5                   10

<210> SEQ ID NO 85
<211> LENGTH: 13
<212> TYPE: PRT
<213> ORGANISM: HSV

<400> SEQUENCE: 85

Pro Phe Tyr Gly Tyr Arg Glu Gly Ser His Thr Glu His
1               5                   10

<210> SEQ ID NO 86
<211> LENGTH: 13
<212> TYPE: PRT
<213> ORGANISM: HSV

<400> SEQUENCE: 86

Phe Tyr Gly Tyr Arg Glu Gly Ser His Thr Glu His Thr
1               5                   10

<210> SEQ ID NO 87
<211> LENGTH: 13
<212> TYPE: PRT
<213> ORGANISM: HSV

<400> SEQUENCE: 87

Tyr Gly Tyr Arg Glu Gly Ser His Thr Glu His Thr Ser
1               5                   10

<210> SEQ ID NO 88
<211> LENGTH: 13
<212> TYPE: PRT
<213> ORGANISM: HSV

<400> SEQUENCE: 88

Gly Tyr Arg Glu Gly Ser His Thr Glu His Thr Ser Tyr
1               5                   10

<210> SEQ ID NO 89
<211> LENGTH: 13
```

```
<212> TYPE: PRT
<213> ORGANISM: HSV

<400> SEQUENCE: 89

Tyr Arg Glu Gly Ser His Thr Glu His Thr Ser Tyr Ala
1               5                   10

<210> SEQ ID NO 90
<211> LENGTH: 6
<212> TYPE: PRT
<213> ORGANISM: HSV

<400> SEQUENCE: 90

Val Tyr Met Ser Pro Phe
1               5

<210> SEQ ID NO 91
<211> LENGTH: 6
<212> TYPE: PRT
<213> ORGANISM: HSV

<400> SEQUENCE: 91

Tyr Met Ser Pro Phe Tyr
1               5

<210> SEQ ID NO 92
<211> LENGTH: 6
<212> TYPE: PRT
<213> ORGANISM: HSV

<400> SEQUENCE: 92

Met Ser Pro Phe Tyr Gly
1               5

<210> SEQ ID NO 93
<211> LENGTH: 6
<212> TYPE: PRT
<213> ORGANISM: HSV

<400> SEQUENCE: 93

Ser Pro Phe Tyr Gly Tyr
1               5

<210> SEQ ID NO 94
<211> LENGTH: 6
<212> TYPE: PRT
<213> ORGANISM: HSV

<400> SEQUENCE: 94

Pro Phe Tyr Gly Tyr Arg
1               5

<210> SEQ ID NO 95
<211> LENGTH: 6
<212> TYPE: PRT
<213> ORGANISM: HSV

<400> SEQUENCE: 95

Phe Tyr Gly Tyr Arg Glu
1               5

<210> SEQ ID NO 96
<211> LENGTH: 6
<212> TYPE: PRT
<213> ORGANISM: HSV
```

<400> SEQUENCE: 96

Tyr Gly Tyr Arg Glu Gly
1               5

<210> SEQ ID NO 97
<211> LENGTH: 6
<212> TYPE: PRT
<213> ORGANISM: HSV

<400> SEQUENCE: 97

Gly Tyr Arg Glu Gly Ser
1               5

<210> SEQ ID NO 98
<211> LENGTH: 6
<212> TYPE: PRT
<213> ORGANISM: HSV

<400> SEQUENCE: 98

Tyr Arg Glu Gly Ser His
1               5

<210> SEQ ID NO 99
<211> LENGTH: 6
<212> TYPE: PRT
<213> ORGANISM: HSV

<400> SEQUENCE: 99

Arg Glu Gly Ser His Thr
1               5

<210> SEQ ID NO 100
<211> LENGTH: 6
<212> TYPE: PRT
<213> ORGANISM: HSV

<400> SEQUENCE: 100

Glu Gly Ser His Thr Glu
1               5

<210> SEQ ID NO 101
<211> LENGTH: 6
<212> TYPE: PRT
<213> ORGANISM: HSV

<400> SEQUENCE: 101

Gly Ser His Thr Glu His
1               5

<210> SEQ ID NO 102
<211> LENGTH: 6
<212> TYPE: PRT
<213> ORGANISM: HSV

<400> SEQUENCE: 102

Ser His Thr Glu His Thr
1               5

<210> SEQ ID NO 103
<211> LENGTH: 6
<212> TYPE: PRT
<213> ORGANISM: HSV

<400> SEQUENCE: 103

```
His Thr Glu His Thr Ser
1               5

<210> SEQ ID NO 104
<211> LENGTH: 6
<212> TYPE: PRT
<213> ORGANISM: HSV

<400> SEQUENCE: 104

Thr Glu His Thr Ser Tyr
1               5

<210> SEQ ID NO 105
<211> LENGTH: 6
<212> TYPE: PRT
<213> ORGANISM: HSV

<400> SEQUENCE: 105

Glu His Thr Ser Tyr Ala
1               5
```